(12) United States Patent
Webster et al.

(10) Patent No.: US 8,822,875 B2
(45) Date of Patent: Sep. 2, 2014

(54) METHODS AND SYSTEMS FOR COHERENT IMAGING AND FEEDBACK CONTROL FOR MODIFICATION OF MATERIALS

(75) Inventors: Paul J. L. Webster, Kingston (CA); James M. Fraser, Kingston (CA); Victor X. D. Yang, Toronto (CA)

(73) Assignee: Queen's University at Kingston, Kingston (CA)

( * ) Notice: Subject to any disclaimer, the term of this patent is extended or adjusted under 35 U.S.C. 154(b) by 352 days.

(21) Appl. No.: 13/245,334

(22) Filed: Sep. 26, 2011

(65) Prior Publication Data
US 2012/0138586 A1 Jun. 7, 2012

Related U.S. Application Data

(60) Provisional application No. 61/386,496, filed on Sep. 25, 2010, provisional application No. 61/435,076, filed on Jan. 21, 2011.

(51) Int. Cl.
| | |
|---|---|
| *B23K 26/03* | (2006.01) |
| *B23K 26/20* | (2014.01) |
| *G01N 21/84* | (2006.01) |
| *A61B 18/20* | (2006.01) |
| *G01J 3/453* | (2006.01) |
| *A61B 17/00* | (2006.01) |
| *A61B 18/00* | (2006.01) |

(52) U.S. Cl.
CPC ............... *G01N 21/84* (2013.01); *B23K 26/20* (2013.01); *B23K 26/03* (2013.01); *A61B 18/20* (2013.01); *A61B 2017/00057* (2013.01); *A61B 2018/00642* (2013.01); *B23K 26/032* (2013.01); *G01J 3/453* (2013.01); *G01N 2021/8416* (2013.01)
USPC ............ 219/121.11; 219/121.13; 219/121.14; 219/121.62; 219/121.63; 219/121.64; 219/121.83; 219/124.1

(58) Field of Classification Search
CPC .... B23K 26/04; B23K 26/046; B23K 26/048; B23K 26/20; B23K 26/03; B23K 26/032
USPC .......... 219/121.26, 121.13, 121.14, 219/121.61–121.64; 250/396 R, 201.2; 356/498
See application file for complete search history.

(56) References Cited

U.S. PATENT DOCUMENTS

| | | |
|---|---|---|
| 5,387,969 A | 2/1995 | Marantette |
| 5,446,547 A | 8/1995 | Guenther et al. |

(Continued)

FOREIGN PATENT DOCUMENTS

| | | |
|---|---|---|
| DE | 10155203 A1 | 6/2003 |
| WO | 2007038975 A1 | 12/2007 |

OTHER PUBLICATIONS

Oh, W.Y. et al., "Ultrahigh-speed optical frequency domain imaging and application to laser ablation monitoring", Applied Physics Letters 88, 103902 (2006), American Institute of Physics, Mar. 10, 2006.

(Continued)

*Primary Examiner* — Samuel M Heinrich
(74) *Attorney, Agent, or Firm* — Stephen J. Scribner; R. Allan Brett; Carol Miernicki

(57) ABSTRACT

Methods and systems are provided for using optical interferometry in the context of material modification processes such as surgical laser or welding applications. An imaging optical source that produces imaging light. A feedback controller controls at least one processing parameter of the material modification process based on an interferometry output generated using the imaging light. A method of processing interferograms is provided based on homodyne filtering. A method of generating a record of a material modification process using an interferometry output is provided.

24 Claims, 28 Drawing Sheets

(56) References Cited

U.S. PATENT DOCUMENTS

| | | | |
|---|---|---|---|
| 6,485,413 | B1 | 11/2002 | Boppart et al. |
| 6,763,259 | B1 | 7/2004 | Hauger et al. |
| 7,411,682 | B2 | 8/2008 | Moshe |
| 7,688,453 | B2 | 3/2010 | Willby et al. |
| 2002/0153500 | A1 | 10/2002 | Fordahl et al. |
| 2003/0196994 | A1* | 10/2003 | Nikitin et al. ............ 219/121.64 |
| 2005/0027199 | A1 | 2/2005 | Clarke |
| 2006/0179992 | A1 | 8/2006 | Kermani |
| 2010/0142780 | A1 | 6/2010 | Yasuno et al. |
| 2010/0155375 | A1 | 6/2010 | Dietz et al. |
| 2011/0284508 | A1 | 11/2011 | Miura et al. |
| 2012/0285936 | A1 | 11/2012 | Urashima et al. |

OTHER PUBLICATIONS

Patel, Nirlep A. et al., "Guidance of aortic ablation using optical coherence tomography", The International Journal of Cardiovascular Imaging 19: 171-178 (2003).

Boppart, Stephen A. et al., "High-Resolution Optical Coherence Tomography-Guided Laser Ablation of Surgical Tissue", Journal of Surgical Research 82, 275-284 (1999).

Ohmi, Masato et al., "In-situ observation of tissue laser ablation using optical coherence tomography", Optical and Quantum Electronics (2005) 37:1175-1183.

Wiesemann, W.: 2.8 Process monitoring and closed-loop control. Poprawe, R., Weber, H., Herziger, G. (ed.). SpringerMaterials—The Landolt-Börnstein Database (http://www.springermaterials.com). DOI: 10.1007/10877768_10 (2004).

International Search Report and Written Opinion dated Dec. 8, 2011 for PCT International Application No. PCT/CA2011/050599.

Leung, B.Y.C., et al., "Real-time coherent imaging of ultrafast ablation," Optical Society of America, CthG4 (2009).

Ohmi, M., et al., "In-situ observation of tissue laser ablation using optical coherence tomography", Optical and Quantum Electronics, vol. 37, 1175-1183 (2005).

Vakoc, B.J., et al., "Real-time microscopic visualization of tissue response to laser thermal therapy",Journal of Biomedical Optics, vol. 12 (2), 020501-1-020501-3 (Mar./Apr. 2007).

Weisner, M., et al., "Optical coherence tomography for process control of laser micromachining", Review of Scientific Instruments, vol. 81, 033705-1-033705-7 (2010).

Webster, P.J.L., et al., "Inter- and intrapulse dynamics and feedback control for laser machining", Optical Society of America, CF16 (2009).

Webster, P.J.L., et al., "In situ 24 kHz coherent imaging of morphology change in laser percussion drilling" Optics Letters, vol. 35, No. 5, 646-648 (2010).

Webster, P.J.L., et al., "High speed in situ depth profiling of ultrafast micromachining", Optics Express, vol. 15, No. 23, 14967-14972 (2007).

Yu, J.X.Z., et al., "High quality percussion drilling of silicon with a CW fiber laser", Proceedings of SPIE Photonics West: LASE, San Francisco, CA, (2010).

Muller, M.S. et al., "Ultrafast technology applied to optical coherence tomography" La Physique Au Canada, vol. 65, No. 2, 93-96 (2009).

Leung, B.Y.C., et al., "Real-time guidance of thermal and ultrashort pulsed laser ablation in hard tissue using inline coherent imaging", Lasers in Surgery and Medicine vol. 44 No. 3, 249-56 (2012).

Webster, P.J.L., et al., "Automatic real-time guidance of laser machining with inline coherent imaging", J. Laser Appl. vol. 23 No. 2, Feb. 2001 (2011).

Buzug, T.M., et al., "Navigation concept for image-guided laser surgery", Proc Int. IEEE Conf. Mechatronics Robotics 1403-1408 (2004).

Hohlweg-Majert, B., et al., "Bone treatment laser-navigated surgery", Lasers Med. Sci. vol. 25(1), 67-71 (2010).

Stopp, S., et al., "A new concept for navigated laser surgery", Lasers Med. Sci. vol. 23(3) 261-266 (2008).

Stopp, S., et al., "A new approach for creating defined geometries by navigated laser ablation based on volumetric 3-D data", IEEE Trans. Biomed Eng. vol. 55(7) 1872-1880 (2008).

Rupprecht, S., et al., "Sensor-based laser ablation for tissue specific cutting: an experimental study", Lasers Med. Sci. vol. 19(2) 81-88 (2004).

Fercher, A.F., et al., "Optical coherence tomography—principles and applications", Rep. Prog. Phys. vol. 66(2) 239-303 (2003).

Boppart, S.A., et al., "High-resolution optical coherence tomography-guided laser ablation of surgical tissue", J. Surg. Res. vol. 82, 275-284 (1999).

Oh, W.Y., et al., "Ultrahigh-speed optical frequency domain imaging and application to laser ablation monitoring", Appl. Phys. Lett. vol. 88(10) 103902 (2006).

Vakoc, B.J., et al., "Real-time microscopic visualization of tissue response to laser thermal therapy", J. Biomed. Opt., vol. 12(2) 020501 (2007).

Wang, Y., et al., "Low-noise broadband light generation from optical fibers for use in high-resolution optical coherence tomography", J. Opt. Soc. Am. A. vol. 22(8) 1492-1499 (2005).

Bonora, S., et al., "Low-threshold ablation of enamel and dentin using Nd:YAG laser assisted with chromophore with different pulse shapes", Proc. SPIE vol. 5313 23-30 (2004).

Li, Z.Z., et al., "Bone ablation with Er:YAG and CO2 laser: study of thermal and acoustic effects", Las. Surg. Med., vol. 12(1) 79-85 (1992).

Leech, P.W., "Laser ablation of multilayered hot stamping foil", J. Mater. Process. Technol. 209, 4281-4285 (2009).

Lausten, R., et al., "On-the-fly depth profiling during ablation with ultrashort laser pulses: a tool for accurate micromachining and laser surgery", Appl. Phys. Lett. 79(6), 884-886 (2001).

Webster, P.J.L., et al., "In-situ localization of machining dynamics with coherent microscopy", Canadian Laser Application Network (CLAN) Workshop, Mar. 12, 2009.

Webster, P.J.L., et al., "Coaxial real-time metrology and gas assisted laser micromachining: process development, stochastic behavior and feedback control", Proceedings of SPIE Photonics West: MOEMS 759003-759003-10, San Francisco, CA, (2010).

Webster, P.J.L., et al., "Guidance of hard tissue ablation by forward-viewing optical coherence tomography", Proceedings of SPIE vol. 7554, 75540Z-75540Z-6 (2010).

Lindner, M.W., et al., "Spectral Radar: Optical Coherence Tomography in the Fourier Domain", in: Handbook of Optical Coherence Tomography, edited by E. Bouma and G. J. Tearney, Marcel Dekker, New York, pp. 335-357 (2002).

Webster, P.J.L., et al., "High speed observation of ultrafast machining dynamics", in Conference on Lasers and Electro-Optics p. CMF6 Optical Society of America, San Jose, (2008).

Webster, P.J.L., et al., "Inline coherent imaging of laser micromachining", International Symposium on Optomechatronic Technologies, Toronto ON (2010).

Fraser, J.M., "In-situ coherent imaging to monitor and control laser processing", Harvard University Colloquium (2011).

Hofer, B., et al., "Signal post processing in frequency domain OCT and OCM using a filter bank approach", Proc. SPIE 6443, 644300 (2007).

Hofer, B., et al., "Dispersion encoded full range frequency domain optical coherence tomography", Optics Express, vol. 17 (1), 7-24 (2009).

Ben Y.C. Leung et al. "Real time Coherent Imaging of Ultrafast Ablation" Department of Physics, Engineering Physics and Astronomy, Queen's University, Kingston, Ontario, Canada, Jun. 4, 2009.

Paul J.L. Webster et al. "Inter- and Intra-pulse Dynamics & Feedback Control for Laser Machining", Queen's University, Kingston, Ontario, Canada.

Joe X.Z. Yu et al. "High-quality percussion drilling of silicon with a CW fiber laser", Department of Physics, Engineering Physics and Astronomy, Queen's University, Kingston, Ontario, Canada, Jan. 27, 2010.

(56) References Cited

OTHER PUBLICATIONS

Webster, P.J.L., et al., "Coaxial real-time metrology and gas assisted laser micromachining: process development, stochastic behavior and feedback control" Queen's University, Kingston, Ontario, Canada.

Webster, P.J.L., et al., "Guidance of hard tissue ablation by forward-viewing optical coherence tomography", Queen's University, Kingston, Ontario, Canada.

Webster, P.J.L., et al., "High speed observation of ultrafast machining dynamics", Queen's University, Kingston, Ontario, Canada.

International Search Report for PCT/CA2014/000273 filed on International filing date of Mar. 13, 2014.

Written Opinion for PCT/CA2014/000273 filed on International filing date of Mar. 13, 2014.

* cited by examiner

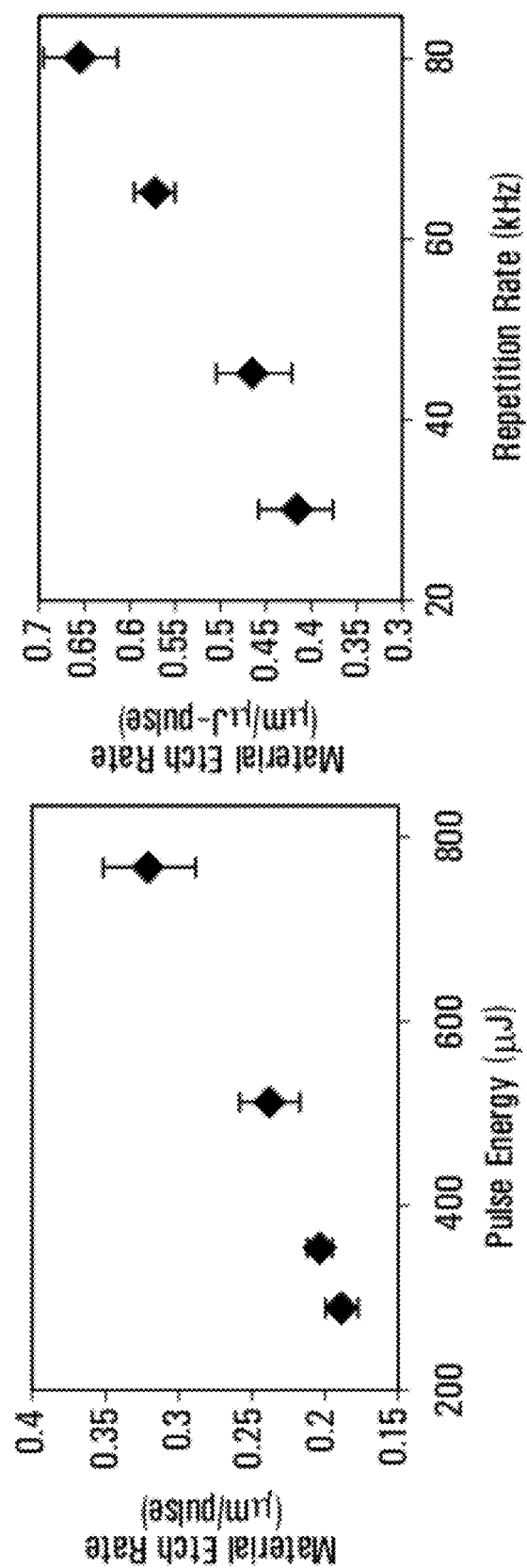

METHODS AND SYSTEMS FOR COHERENT IMAGING AND FEEDBACK CONTROL FOR MODIFICATION OF MATERIALS

RELATED APPLICATIONS

This application claims the benefit of U.S. Provisional Application No. 61/386,496 filed Sep. 25, 2010, and U.S. Provisional Application No. 61/435,076 filed Jan. 21, 2011, both hereby incorporated by reference in its entirety.

FIELD

The application relates to coherent imaging, and to optical modification or measurement of materials, such as through the use of lasers.

BACKGROUND OF THE INVENTION

Lasers are known to be important tools for processing a wide range of materials. Example processes include welding, drilling, cutting, routing, perforating, sintering and surface treatment. Materials can include metals, semiconductors, dielectrics, polymers, as well as hard and soft biological tissue. By focusing a beam, it can be possible to achieve improved precision of the laser's action in a direction transverse to the beam axis. However, localizing the laser's action in the axial direction of the beam can be difficult.

Common to many laser processes, are metrology techniques to guide a processing system and obtain quality assurance data before, during and/or after the laser action. Aspects of the laser interaction and practical limitations can interfere with the standard techniques. Some examples of such aspects include plasma generation/electrical interference, high aspect ratio holes, blinding by the processing laser, fast moving material, unpredictable geometries, material relaxation and potential damage to the metrology instrumentation by the processing laser.

Control of laser cut depth is a major enabler for the use of lasers in a variety of microsurgeries. In particular, there exists an enormous demand for spinal surgeries (one third of neurosurgery cases in some hospitals). Current mechanical tools are archaic and difficult to use safely and efficiently except by experienced surgeons. It would be desirable to use lasers because of their high transverse control, no tool wear and non-contact operation (infection control). There are other benefits from laser use such as flexible coagulation control and a natural aseptic effect. However, lasers have very poor axial control (meaning, the beam continues in the axial direction). This means that if the point of perforation is not controlled with extreme precision, unintended injury to surrounding soft tissue is almost certain. Thus, the use of lasers has so far been precluded in a vast number of cases.

Current laser systems are mainly used on soft tissue and rely on an assumption of constant material removed for a given amount of exposure. However, this assumption is not always a good one and furthermore, one often does not know exactly how much tissue needs to be removed a priori. Precision cutting or ablation at interfaces of tissue with vastly different optical, mechanical, and thermal properties is of particular interest to neurological, orthopedic, ear-nose-throat, and laparoscopic surgeons. Unlike corneal laser surgery, these surgical specialties are mainly concerned with nontransparent, optically turbid tissue types with heterogeneous tissue properties on the microscopic scale, where detailed and precise a priori opto-thermal characterization is not feasible. The resultant nondeterministic tissue cutting/ablation process greatly hinders the use of lasers during such surgeries. For example, several authors have recently highlighted that practical laser osteotomy (surgical procedure to cut bone) is limited by a lack of laser depth control. The potential benefit of precise removal of tissue may provide significant clinical impact in this and other areas of surgical oncology and implantation.

In industrial applications, laser processing has the advantage that a single laser can be used to clean, weld and/or machine different materials without mechanical adjustment or changing chemical treatments. Although laser ablation of heterogeneous or multi-layered samples has been accomplished, these processes require tremendous amounts of development and rely on uniform sample characteristics or models with limited applicability and varied success. Laser welding and cleaning, too, typically require extensive multi-parameter optimization. This problem of achieving a specific set of processing objectives (for example feature aspect ratio, heat affected zone, etc.) within the available parameter space (encompassing feed rate, pulse energy, pulse duration, wavelength, assist gas, spot size and focal position) is compounded by characteristics of the material (for example melt and ablation threshold and polymer molecular weight). Accordingly, industrial laser process development requires significant time and financial investment, and may demand fine tolerance feedstock to ensure reliability. Laser process monitoring and control of welding and drilling has used sensors to measure the metal temperature, reflectivity and plasma temperature near the area being processed. These forms of metrology do not provide an accurate measurement of laser beam penetration depth.

Laser welding is an industrial process that is particularly well suited to automated and high volume manufacturing. The diverse applications for laser welding have in common a process of controlled heating by a laser to create a phase change localized to the bond region. Controlling this phase change region (PCR) is important to control the geometry and quality of the weld and the overall productivity of the welding system. The high spatial coherence of laser light allows superb transverse control of the welding energy. Axial control (depth of the PCR) and subsequent thermal diffusion are problematic in thick materials. In these applications, the depth of the PCR is extended deep into the material (e.g. 50 micrometers and deeper) using a technique widely known as "keyhole welding". Here, the beam intensity is sufficient to melt the surface to open a small vapor channel (also known as a "capillary" or "the keyhole") which allows the optical beam to penetrate deep into the material. Depending on the specific application, the keyhole is narrow (e.g. <mm) but several millimeters deep and sustained with the application of as much as ~$10^5$ W of optical power. As a result, the light-matter interaction region inside the PCR can be turbulent, unstable and highly stochastic. Unfortunately, instability of keyhole formation can lead to internal voids and high weld porosity resulting in weld failure, with potential catastrophic consequences. Weld quality verification is usually required, often using expensive ex situ and destructive testing. Welding imaging solutions are offered but are limited in their capabilities and usually monitor regions either before or after of the PCR, to track the weld joint, or record the top surface of the cooled weld joint.

SUMMARY

According to one aspect of the present invention, there is provided an apparatus comprising: a material processing beam source that produces a material processing beam that is applied to a sample location in a material modification process; an imaging optical source that produces imaging light; an optical interferometer that produces an interferometry output using at least a component of the imaging light that is delivered to the sample, the interferometry output based on at least one optical path length to the sample compared to another optical path length; and a feedback controller that controls at least one processing parameter of the material modification process based on the interferometry output.

According to another aspect of the present invention, there is provided feedback control apparatus for use with a material processing system that implements a material modification process, the material processing system having an optical access port, the apparatus comprising: an imaging optical source that produces imaging light; an input-output port that outputs a first component of the imaging light to the optical access port of the material processing system and that receives a reflection component of the imaging light in return; an optical combiner that combines the reflection component and another component of the imaging light to produce an interferometry output, the interferometry output based on a path length taken by the first component and the reflection component compared to a path length taken by the another component of the imaging light; a feedback controller that generates at least one signal that influences at least one processing parameter of the material modification process based on the interferometry output.

In some embodiments, the feedback controller is further configured to determine if the interferometry output initially comprises substantially only light reflected along a reference path, after which the interferometry output is based on the path length of a sample path compared to the path length of the reference path.

In some embodiments, the feedback controller determines when or if the interferometry output makes a transition from comprising substantially only light reflected along a reference path to being based on the path length of the sample path compared to the path length of the reference path; and the feedback controller generates at least one signal that influences at least one processing parameter of the material modification process based on the interferometry output taking into account the transition.

In some embodiments, the feedback controller processes multiple instances of the interferometry output to identify a change in the interferometry output in respect of a material being processed, and wherein feedback control is a function of such change.

In some embodiments, the feedback controller provides an indication of a modification/sample motion "speed" or another rate of change, based on the change in the interferometry output.

In some embodiments, the feedback processor further generates an indication of optical index of a material based on the interferometry output.

In some embodiments, the apparatus further comprises: a computer readable medium; and a record generator that generates a record of the material modification process based on the interferometry output at a plurality of times and stores the record on the computer readable medium.

In some embodiments, the feedback controller is a real-time controller that controls the at least one processing parameter of the material modification process during said process.

In some embodiments, the material modification processing beam source is a solid state, fiber or gas laser.

In some embodiments, the material processing beam source is at least one of an ion beam and an electron beam.

In some embodiments, the interferometer comprises: a combiner; a reference arm, a first component of the imaging light being applied to an input of the reference arm resulting in an output signal of the reference arm, the reference arm having said another optical path length; and a sample arm, a second component of the imaging light being applied to the sample arm resulting in an output signal of the sample arm, at least a component of the output signal of the sample arm including reflections of the component of the imaging light from a sample location, the sample arm having said at least one optical path length; wherein the combiner combines the output signal of the reference arm and the output signal of the sample arm to produce a combined signal as said interferometry output; the apparatus further comprising a signal detector configured to produce a first interferogram from the interferometry output.

In some embodiments, the apparatus comprises at least one of: multiple sample arms, a respective interferogram being generated for each sample arm, reference arm combination; multiple reference arms, a respective interferogram being generated for each sample arm, reference arm combination; and multiple reference arms and multiple sample arms, a respective interferogram being generated for each sample arm, reference arm combination.

In some embodiments, the interferometer comprises: at least one splitter and/or optical circulator; and at least one sample arm after the splitter and/or optical circulator, the imaging signal being applied to the sample arm resulting in an output signal of the sample arm, at least a component of the output signal of the sample arm including reflections of the component of the imaging signal from at least two locations in the sample arm and/or the material being processed, the sample arm having said at least one optical path length and said another optical path length; wherein the splitter and/or optical circulator receives the output signal from the sample arm and directs it towards a detector; the apparatus further comprising a signal detector configured to produce an interferogram from the interferometry output.

In some embodiments, the apparatus further comprises: an interferogram processor that performs an analysis based on the interferometry output to produce a depth measurement reflecting how deep the material processing beam has penetrated at the sample location.

In some embodiments, the feedback controller performs an analysis based on the interferometry output and generates feedback control that controls depth cutting relative to an interface that is closest to the cutting laser.

In some embodiments, feedback controller performs an analysis based on the interferometry output and generates feedback control that controls depth cutting relative to an interface that is beyond the current cut depth.

In some embodiments, the feedback controller controls at least one processing parameter of the material modification process based on the depth measurement.

In some embodiments, the at least one processing parameter of the material modification process controlled by the feedback controller comprises at least one of: on/off state of the material processing beam; average power of the material processing beam; pulse duration of the material processing beam; peak intensity of the material processing beam; density of the material processing beam; energy of the material processing beam; particle species of the material processing beam; wavelength of the material processing beam; pulse repetition rate of the material processing beam; pulse energy of the material processing beam; pulse shape of the material processing beam scan speed of the material processing beam; focal diameter of the material processing beam; focal position of the material processing beam; spatial pattern of the material processing beam on the sample; material feed rate; cooling media flow rate; cover/assist gas flow rate; cover/assist gas pressure; cover/assist gas blend; arc welding process parameters (such as voltage, current and wire feed rate); and additive material feed rate.

In some embodiments, the feedback controller controls at least one processing parameter of the material modification process based on the depth measurement by controlling the material processing beam to be off when the depth measurement indicates a specified depth.

In some embodiments, the apparatus further comprises: an interferogram processor that performs an analysis based on the interferometry output to produce an indication of at least one of: when the material modification source beam has penetrated to a specified depth; proximity of the region of the material currently being modified to other regions of the material; remaining amount of material to be penetrated; total depth that has been modified; absolute final depth reached; fluctuations of depth; speed of depth change; and remaining distance to a subsurface interface.

In some embodiments, the apparatus is further configured to sense at least one change at a subsurface level based on the interferometry output.

In some embodiments, the at least one change sensed at a subsurface level comprises at least one of: temperature changes, state changes, fluid flow, and pressure waves.

In some embodiments, the feedback controller controls at least one material modification parameter based on change sensed at the subsurface level.

In some embodiments, a change at the subsurface level is sensed by observing changes in a speckle pattern.

In some embodiments, the feedback controller controls the material processing beam source to turn off the material processing beam based on indication from the interferogram processor.

In some embodiments, the feedback controller controls the material processing beam source to turn on the material processing beam based on indication from the interferogram processor.

In some embodiments, the apparatus comprises: a memory for storing a pre-calculated synthesized interferogram for a target result; a signal detector that produces a measured interferogram from the interferometry output; and an interferogram processor that processes the measured interferogram together with the pre-calculated synthesized interferogram to produce a correlation result;

wherein the feedback controller controls at least one processing parameter of the material modification process based on the correlation result.

In some embodiments, the pre-calculated synthesized interferogram for a target result is an estimate of what is expected when reflections return from a specified depth; and the interferogram processor produces the correlation result by multiplying the measured interferogram by the pre-calculated interferogram on a per detected element basis and then summing.

In some embodiments, at least one of the pre-calculated synthesized interferogram and the measured interferogram is shaped to compensate for at least one of: spectrometer alignment; spectrometer grating angle nonlinearity; imaging distortion from imaging optics in the spectrometer; wavelength to wave number/frequency re-sampling; finite size of detector active area; spectral envelope shape; dispersion mismatch; and another non-ideality contained in the interferogram that degrades image quality.

In some embodiments, the apparatus is further configured to process the correlation result to identify approximately when the volume modified by the material processing beam has reached the specified depth.

In some embodiments, the apparatus is further configured to identify approximately when the specified depth has been reached from when the correlation result meets a threshold.

In some embodiments, the at least one path length is to a first reflector at the sample location and the another path length is to a second reflector at the sample location.

In some embodiments, the at least one path length is at least two path lengths to respective reflectors at the sample location, and the another path length is along a reference arm.

In some embodiments, the apparatus further comprises: an interferogram synthesizer that synthesizes the pre-calculated synthesized interferogram.

According to still another aspect of the present invention, there is provided an apparatus for producing and processing an interferometry output, the apparatus comprising: a memory that stores a pre-calculated synthesized interferogram for a target result; an interferometer for producing an interferometry output; a signal detector that produces a measured interferogram from the interferometry output; an interferogram processor that processes the measured interferogram together with the pre-calculated expected interferogram to produce a correlation result; and a thresholder configured to determine when the result meets a threshold.

In some embodiments, for each of a plurality of target results, the memory stores a respective pre-calculated synthesized interferogram; the interferogram processor processes the measured interferogram together with each pre-calculated synthesized interferogram to produce a respective correlation result; and the thresholder determines when each correlation result meets a respective threshold.

In some embodiments, the pre-calculated synthesized interferogram is an interferogram that is an estimate of what is expected when the target result is achieved by a material modification beam at a sample location; the measured interferogram is in respect of a sample location; and the interferogram processor produces the correlation result by multiplying the measured interferogram by the pre-calculated synthesized interferogram on a per detector element basis and then summing.

In some embodiments, at least one of the pre-calculated synthesized interferogram and the measured interferogram is shaped to compensate for at least one of: spectrometer alignment; spectrometer grating angle nonlinearity; imaging distortion from imaging optics in the spectrometer; wavelength to wave number/frequency re-sampling; finite size of active area of detector; spectral envelope shape; dispersion mismatch; and another non-ideality contained in the interferogram that degrades image quality.

In some embodiments, the target result is an estimate of what is expected when reflections return from a specified depth.

In some embodiments, the apparatus further comprises: a feedback controller that controls a material modification beam source to turn off the material modification beam when the correlation result meets a threshold.

In some embodiments, the apparatus further comprises: a feedback controller that controls at least one processing parameter of a material modification process when the correlation result meets a threshold.

In some embodiments, the at least one processing parameter comprises at least one of: on/off state of the material processing beam; average power of the material processing beam; pulse duration of the material processing beam; peak intensity of the material processing beam; density of the material processing beam; energy of the material processing beam; particle species of the material processing beam; wavelength of the material processing beam; pulse repetition rate of the material processing beam; pulse energy of the material processing beam; pulse shape of the material processing beam scan speed of the material processing beam; focal diameter of the material processing beam; focal position of the material processing beam; spatial pattern of the material processing beam on the sample; material feed rate; cooling media flow rate; cover/assist gas flow rate; cover/assist gas pressure; cover/assist gas blend; arc welding process parameters (such as voltage, current and wire feed rate); and additive material feed rate.

In some embodiments, the apparatus further comprises: a feedback controller that controls a material modification beam source to turn on the material modification beam when the correlation result meets a threshold.

In some embodiments, the apparatus further comprises: an interferogram synthesizer that synthesizes the pre-calculated synthesized interferogram.

According to yet another aspect of the present invention, there is provided an apparatus that generates a record of a material modification process, the apparatus comprising: a material processing beam source that produces a material processing beam that is applied to a sample location in the material modification process, wherein the material modification process is a welding process; an imaging optical source that produces imaging light; an optical interferometer that produces an interferometry output using at least a component of the imaging light that is delivered to the sample, the interferometry output based on at least one optical path length to the sample compared to another optical path length; and a record generator that generates a record of the material modification process based on the interferometry output at a plurality of times.

In some embodiments, the apparatus further comprises: a computer readable storage medium; wherein the record generator stores the record on the compute readable storage medium.

In some embodiments, the apparatus is configured to produce the material processing beam and the imaging light substantially co-axially when delivered to the sample.

According to yet a further aspect of the present invention, there is provided an apparatus that generates a record of a material modification process, the apparatus comprising: a material processing beam source that produces a material processing beam that is applied to a sample location in the material modification process, wherein the material modification process is a medical process employing a laser beam as the material processing beam; an imaging optical source that produces imaging light; an optical interferometer that produces an interferometry output using at least a component of the imaging light that is delivered to the sample, the interferometry output based on at least one optical path length to the sample compared to another optical path length; and a record generator that generates a record of the material modification process based on the interferometry output at a plurality of times.

According to yet a further aspect of the present invention, there is provided a method for controlling at least one processing parameter of a material modification process, the method comprising: generating imaging light with an imaging optical source; producing an interferometry output using at least a component of the imaging light that is delivered to a sample, the interferometry output based on at least one optical path length to the sample compared to another optical path length; and automatically controlling at least one processing parameter of a material modification process based on the interferometry output.

In some embodiments, the method further comprises: applying a material processing beam to the sample location in the material modification process.

In some embodiments, the material modification beam is a drilling laser; automatically controlling comprises controlling a perforation by the material modification beam such that immediately after perforation is detected, or after a selected overdrilling period after perforation is detected, the drilling laser is controlled to stop.

In some embodiments, applying a material processing beam comprises fabricating cooling holes in gas turbines.

In some embodiments, the method further comprises: determining if the interferometry output initially comprises substantially only light reflected along a reference path, after which the interferometry output is based on the path length of a sample path compared to the path length of the reference path.

In some embodiments, determining when or if the interferometry output makes a transition from comprising substantially only light reflected along a reference path to being based on the path length of the sample path compared to the path length of the reference path; and generating feedback to influence influences at least one processing parameter of the material modification process based on the interferometry output taking into account the transition.

In some embodiments, the method comprises: processing multiple instances of the interferometry output to identify a change in the interferometry output in respect of a material being processed, and wherein feedback control is a function of such change.

In some embodiments, the method further comprises: generating an indication of a modification/sample motion "speed" or another rate of change, based on the change in the interferometry output.

In some embodiments, the method further comprises: generating an indication of optical index of a material based on the interferometry output.

In some embodiments, the method further comprises: generating a record of the material modification process based on the interferometry output at a plurality of times; and storing the record.

In some embodiments, automatically controlling at least one processing parameter of a material modification process based on the interferometry output comprises controlling the at least one processing parameter of the material modification process in real-time during said process.

In some embodiments, the material modification processing beam is a laser beam.

In some embodiments, applying a material processing beam to the sample location in the material modification process comprising applying a material processing beam to at least one of: metal; semiconductor; dielectric; hard biological tissue; soft biological tissue; polymer; plastic; wood; composite.

In some embodiments, the material processing beam is at least one of an ion beam and an electron beam.

In some embodiments, producing an interferometry output comprises: applying a first component of the imaging light to an input of a reference arm resulting in an output signal of the reference arm, the reference arm having said another optical path length; applying a second component of the imaging light to a sample arm resulting in an output signal of the sample arm, at least a component of the output signal of the sample arm including reflections of the component of the imaging light from the sample location, the sample arm having said at least one optical path length; and combining the output signal of the reference arm and the output signal of the sample arm to produce a combined signal as said interferometry output; the method further comprising performing signal detection to produce a measured interferogram from the interferometry output.

In some embodiments, the method comprises at least one of: generating a respective interferogram for each of a plurality of sample arm, reference arm combinations, wherein there are multiple sample arms; generating a respective interferogram for each of a plurality of sample arm, reference arm combinations, wherein there are multiple reference arms; and generating a respective interferogram for each of a plurality of sample arm, reference arm combinations, wherein there are multiple reference arms and multiple sample arms.

In some embodiments, generating the interferometry output comprises: at a splitter and/or optical circulator, applying at least a component of the image light to a sample arm, resulting in an output signal of the sample arm, at least a component of the output signal of the sample arm including reflections of the component of the imaging signal from at least two locations in the sample arm and/or the material being processed, the sample arm having said at least one optical path length and said another optical path length; at the splitter and/or optical circulator, receiving the output signal from the sample arm and directing it towards a detector; and performing signal detection to produce a measured interferogram from the interferometry output.

In some embodiments, the method further comprises: analyzing the interferometry output to produce a depth measurement reflecting how deep the material processing beam has penetrated at the sample location.

In some embodiments, the method further comprises performing an analysis based on the interferometry output and generating feedback control that controls depth cutting relative to an interface that is closest to the cutting laser.

In some embodiments, the method further comprises performing an analysis based on the interferometry output and generating feedback control that controls depth cutting relative to an interface that is beyond the current cut depth.

In some embodiments, controlling at least one processing parameter of the material modification process is based on the depth measurement.

In some embodiments, the at least one processing parameter of the material modification process that is controlled comprises at least one of: on/off state of the material processing beam; average power of the material processing beam; pulse duration of the material processing beam; peak intensity of the material processing beam; density of the material processing beam; energy of the material processing beam; particle species of the material processing beam; wavelength of the material processing beam; pulse repetition rate of the material processing beam; pulse energy of the material processing beam; pulse shape of the material processing beam scan speed of the material processing beam; focal diameter of the material processing beam; focal position of the material processing beam; spatial pattern of the material processing beam on the sample; material feed rate; cooling media flow rate; cover/assist gas flow rate; cover/assist gas pressure; cover/assist gas blend; arc welding process parameters (such as voltage, current and wire feed rate); and additive material feed rate.

In some embodiments, controlling at least one processing parameter of the material modification process based on the depth measurement comprises controlling the material processing beam to be off when the depth measurement indicates a specified depth.

In some embodiments, the method further comprises: analyzing the interferometry output to produce an indication of at least one of: when the material modification source beam has penetrated to a specified depth; proximity of the region of the material currently being modified to other regions of the material; remaining amount of material to be penetrated; total depth that has been modified; absolute final depth reached; fluctuations of depth; speed of depth change; and remaining distance to a subsurface interface.

In some embodiments, the method further comprises: sensing at least one change at a subsurface level based on the interferometry output.

In some embodiments, the at least one change sensed at a subsurface level comprises at least one of: temperature changes, state changes, fluid flow, and pressure waves.

In some embodiments, the feedback controller controls at least one material modification parameter based on change sensed at the subsurface level.

In some embodiments, a change at the subsurface level is sensed by observing changes in a speckle pattern.

In some embodiments, the method further comprises controlling the material processing beam source to turn off the material processing beam based on the indication.

In some embodiments, the method of further comprises: controlling the material processing beam source to turn on the material processing beam based on the indication.

In some embodiments, the method further comprises: storing a pre-calculated synthesized interferogram for a target result in a memory; producing a measured interferogram from the interferometry output; processing the measured interferogram together with the pre-calculated synthesized interferogram to produce a correlation result; wherein controlling at least one processing parameter of the material modification process is based on the correlation result.

In some embodiments, the pre-calculated synthesized interferogram for a target result is an estimate of what is expected when reflections return from a specified depth; producing the correlation result comprises multiplying the first interferogram by the pre-calculated interferogram on a per detected element basis and then summing.

In some embodiments, the method further comprises: shaping at least one of the pre-calculated synthesized interferogram and the first interferogram to compensate for at least one of: spectrometer alignment; spectrometer grating angle nonlinearity; imaging distortion from imaging optics in the spectrometer; wavelength to wave number/frequency re-sampling; finite size of detector active area; spectral envelope shape; dispersion mismatch; and another non-ideality contained in the interferogram that degrades image quality.

In some embodiments, the method further comprises: processing the correlation result to identify approximately when the volume modified by the material processing beam has reached the specified depth.

In some embodiments, the method further comprises: identifying approximately when the specified depth has been reached when the correlation result meets a threshold.

In some embodiments, the at least one path length is to a first reflector at the sample location and the another path length is to a second reflector at the sample location.

In some embodiments, the at least one path length is at least two path lengths to respective reflectors at the sample location, and the another path length is along a reference arm.

In some embodiments, the method further comprises: synthesizing the pre-calculated synthesized interferogram.

According to still a further aspect of the present invention, there is provided a method for producing and processing an interferometry output, the method comprising: storing a pre-calculated synthesized interferogram for a target result in memory; producing an interferometry output; detecting a measured interferogram from the interferometry output; processing the measured interferogram together with the pre-calculated expected interferogram to produce a correlation result; and determining when the result meets a threshold.

In some embodiments, for each of a plurality of target results, storing a respective pre-calculated synthesized interferogram in the memory; processing the measured interferogram together with each pre-calculated synthesized interferogram to produce a respective correlation result; and determining when each correlation result meets a respective threshold.

In some embodiments, the pre-calculated synthesized interferogram is an interferogram that is an estimate of what is expected when the target result is achieved by a material modification beam at a sample location; the measured interferogram is in respect of a sample location; and producing the correlation result comprises multiplying the measured interferogram by the pre-calculated synthesized interferogram on a per detector element basis and then summing.

In some embodiments, the method further comprises: shaping at least one of the pre-calculated synthesized interferogram and the measured interferogram to compensate for at least one of: spectrometer alignment; spectrometer grating angle nonlinearity; imaging distortion from imaging optics in the spectrometer; wavelength to wave number/frequency re-sampling; finite size of active area of detector; spectral envelope shape; dispersion mismatch; and another non-ideality contained in the interferogram that degrades image quality.

In some embodiments, the target result is an estimate of what is expected when reflections return from a specified depth.

In some embodiments, the method further comprises: controlling a material modification beam source to turn off the material modification beam when the correlation result meets a threshold.

In some embodiments, the method further comprises: controlling at least one processing parameter of a material modification process when the correlation result meets a threshold.

In some embodiments, the at least one processing parameter comprises at least one of: on/off state of the material processing beam; average power of the material processing beam; pulse duration of the material processing beam; peak intensity of the material processing beam; density of the material processing beam; energy of the material processing beam; particle species of the material processing beam; wavelength of the material processing beam; pulse repetition rate of the material processing beam; pulse energy of the material processing beam; pulse shape of the material processing beam scan speed of the material processing beam; focal diameter of the material processing beam; focal position of the material processing beam; spatial pattern of the material processing beam on the sample; material feed rate; cooling media flow rate; cover/assist gas flow rate; cover/assist gas pressure; cover/assist gas blend; arc welding process parameters (such as voltage, current and wire feed rate); and additive material feed rate.

In some embodiments, the method further comprises: controlling a material modification beam source to turn on the material modification beam when the correlation result meets a threshold.

In some embodiments, the method further comprises: synthesizing the pre-calculated synthesized interferogram.

According to another aspect of the present invention, there is provided a method of generating a record of a material modification process, the method comprising: applying a material processing beam to a sample location as part of the material modification process, wherein the material modification process is a welding process; generating imaging light with an imaging optical source; producing an interferometry output using at least a component of the imaging light that is delivered to the sample, the interferometry output based on at least one optical path length to the sample compared to another optical path length; and generating a record of the material modification process based on the interferometry output at a plurality of times.

In some embodiments, the method further comprises: storing the record.

In some embodiments, the material processing beam and the imaging light are substantially co-axial when delivered to the sample.

In some embodiments, the record comprises a quality of the laser weld.

In some embodiments, the record comprises an element of the melt pool in the process of laser welding.

In some embodiments, the record comprises indications of an impending break through.

In some embodiments, a material interface on the interior of the sample is identified and used for controlling the material modification process.

In some embodiments, the record comprises keyhole stability.

In some embodiments, the record comprises penetration depth.

According to another aspect of the present invention, there is provided a method of generating a record of a material modification process, the method comprising: applying a material processing beam to a sample location as part of the material modification process, wherein the material modification process is a medical process employing a laser beam as the material processing beam; generating imaging light with an imaging optical source; producing an interferometry output using at least a component of the imaging light that is delivered to the sample, the interferometry output based on at least one optical path length to the sample compared to another optical path length; and generating a record of the material modification process based on the interferometry output at a plurality of times.

In some embodiments, the method further comprises at least one of: selecting a location of a zero optical path length difference point below an area of interest of the sample.

In some embodiments, the zero optical path length difference point is selected to be in the sample being measured.

In some embodiments, the zero optical path length difference point is selected to be below the sample being measured.

In some embodiments, the method further comprises at least one of: Talbot band techniques to tailor the sensitivity vs. depth curve; nonlinear time gating; and accessing an analog fringe signal before final digitization, and then using direct hardware demodulation and/or filtering to attenuate certain fringe frequencies that correspond to depths where high reflectivity is expected while retaining sensitivity at depths where the signal is weaker.

In some embodiments, the method further comprises: using a single processing beam source to process multiple samples in multiple processing locations.

In some embodiments, the method comprises: using matched sample arm paths to the multiple processing locations and a common reference path.

In some embodiments, the method comprises: using a respective reference arm for each processing location.

In some embodiments, the method further comprises at least one of: dynamically adjusting the path length of the sample arm; dynamically adjusting the path length of the reference arm.

In some embodiments, the method further comprises: switching between a plurality of reference arms.

In some embodiments, a method comprises: using the ICI system to track a location of a point of interest; adjusting (e.g. adaptively) the location of the zero optical path length difference point relative to the location of the point of interest.

In some embodiments, the method further comprises using the ICI system to perform at least one of: a) tracking a bottom of a hole during drilling; b) controlling a speed of perforation; c) observing a point when a material is perforated; d) anticipating a point in time at which the laser will perforate a material; e) adjusting the laser process to avoid damage to surfaces below a new hole; f) confirming that a hole is not refilled after the laser is turned off; g) controlling drilling, cutting or welding to a prescribed depth; and h) controlling drilling, cutting or welding to a selected depth relative to a selected material interface.

In some embodiments, the method further comprises: configuring the ICI system so that the imaging optical source illuminates an area or volume of the sample that encompasses multiple reflective features of the sample that are different axial heights, or different transverse displacements relative to the center axis of the imaging beam, or any combination thereof.

According still another aspect of the present invention, there is provided a computer readable storage medium having stored thereon a record of a laser welding material modification process that is based on an interferometry output at a plurality of times.

Inline coherent imaging observation and/or control approaches have been summarized above, and detailed below. More generally, any one, or any combination of two or more of the described inline coherent imaging observation and/or control approaches may be applied to one of the following applications:

Welding, including hybrid laser arc welding;
Brazing;
Surface texturing, including dimpling, pitting, roughening, smoothing;
Laser driven chemical processes including photopolymerization, metal precipitation;
Annealing, including selective annealing;
Tempering;
Hardening and heat treating;
Sintering;
Laser incubation;
Trench cutting;
Trepan drilling—this is where the laser is rapidly aimed in a circle to drill a round, clean hole;
Single-sided breakthrough detection in laser perforation of hard tissue, or metals polymers, ceramics;
Cutting of biological material, including materials for synthetic organs and their precursors;
drilling of printed circuit board vias and/or trench cutting in printed circuit boards;
Joining or fusing or welding of biological material.

BRIEF DESCRIPTION OF THE DRAWINGS

FIG. 10 shows an example of the material etch rate and removal efficiency in bovine rib bone due to exposure from a ns-duration fiber laser (constant average power 23 W);

DETAILED DESCRIPTION

Figure 1:
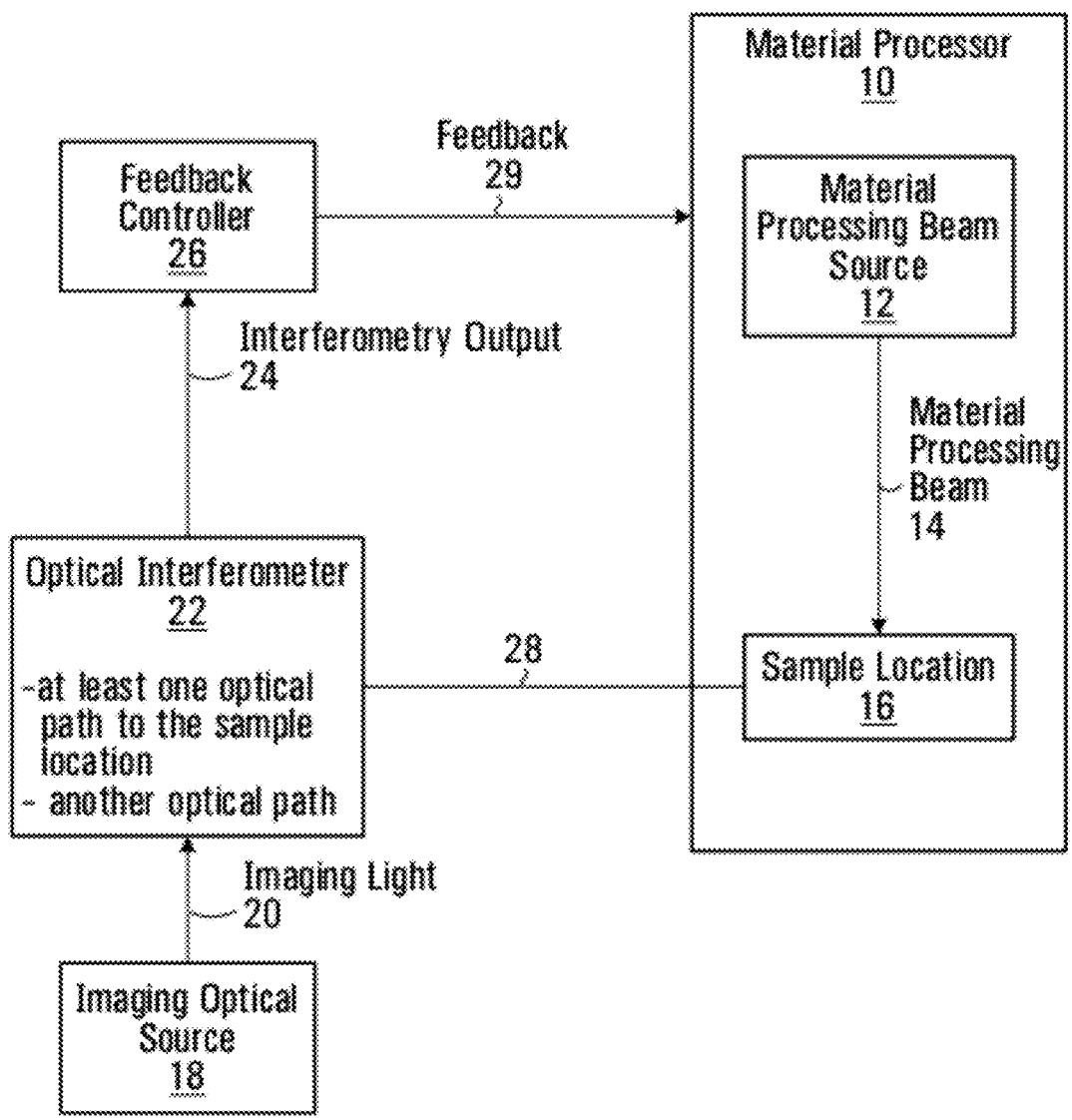
FIG. 1 is a block diagram of a material processing system featuring feedback control from an inline coherent imaging system provided by an embodiment of the invention.

FIG. 1 is a logical block diagram of a material processing system featuring inline coherent imaging (ICI) and feedback control, in accordance with an embodiment of the invention. The system has a material processor 10 that implements a material modification process. The material processor 10 has a material processing beam source 12 that produces a material processing beam 14 that, in turn, modifies a sample located at a sample location 16. Also shown is an imaging optical source 18 that produces imaging light 20, at least a component of which is input to an optical interferometer 22. The interferometer 24 produces an interferometry output 24 that is input to a feedback controller 26. The feedback controller 26 generates feedback 29 that is input to the material processor to control at least one processing parameter of the material modification process.

The optical interferometer 22 produces the interferometry output using at least a component of the imaging light 20 that is delivered to the sample location 16. Line 28 is a logical representation of the interaction between the optical interferometer 22 and the sample location 16. The interferometry output 24 is based on a length of at least one optical path to the sample location compared to a length of another optical path. The optical paths are not depicted in the Figure in the interest of clarity, but various examples are described later. The sample location is the location from which the reflected imaging light is collected. The sample location can be selected from various options to achieve different imaging objectives. For example, in some embodiments, the sample location is at the physical location of a material sample being processed. In some embodiments, the sample location is near the physical location of a material sample being processes. In some embodiments, the sample location is a position chosen to yield meaningful information about the material processing.

In some embodiments, the interferometry output at multiple instances is processed to identify changes in interferometry output in respect of a material being processed. In some embodiments, at least some of the feedback control is a function of such changes. In some embodiments, changes in the interferometry data are used to provide an indication of modification/sample motion "speed" or other rates of change.

In a specific example of processing the interferometry data to identify changes, in some embodiments, the feedback controller is further configured to determine if the interferometry output initially comprises substantially only light reflected along a reference path (this reference path may be along a reference arm if there is one or along the sample arm) after which the interferometry output is based on the path length of a sample path(s) compared to the path length of the reference path. This might occur, for example, when the sample location initially has only one reflective surface/subsurface (in no reference arm case) or no reflective surface/subsurface (in reference arm case), and then after material has been modified and/or moved relative to the imaging optics, at some point there is an additional reflective surface/sub-surface detected.

In some embodiments, the feedback controller is further configured to determine when the interferometry output makes a transition from comprising substantially only light reflected along a reference path (this reference path may be along a reference arm if there is one or along the sample arm) after which the interferometry output is based on the path length of a sample path compared to the path length of the reference path. The feedback controller generates at least one signal that influences at least one processing parameter of the material modification process based on the interferometry output taking into account the transition.

In some embodiments, the feedback controller 26 is a real-time controller that controls the processing parameter of the material modification process during the process. In another embodiment, the feedback controller controls at least one processing parameter during intervals between successive processes.

In some embodiments, the material modification processing beam source is a laser, such as a solid state, fiber or gas laser.

In some embodiments, the material modification processing beam source generates an ion beam and/or an electron beam.

The material being processed by such a system may, for example, be one or more of: metal, semiconductor, dielectric, hard biological tissue, soft biological tissue, plastic, rubber, wood, composite. Other materials are possible.

In some embodiments, the interferometer has a combiner, and two distinct arms, referred to as a reference arm, and a sample arm. A first component of the imaging light is applied to an input of the reference arm resulting in an output signal of the reference arm. A second component of the imaging light is applied to the sample arm resulting in an output signal of the sample arm. At least a component of the output signal of the sample arm includes reflections of the component of the imaging light from the sample location. The combiner combines the output signal of the reference arm and the output signal of the sample arm to produce a combined signal which functions as the interferometry output. Depending on the implementation, the combiner may be a coupler, a circulator, or a splitter; any component that performs the combining function can be used.

In some embodiments, the system also has a signal detector that produces an interferogram from the interferometry output. In some embodiments, the signal detector is in the form of an array of detector elements. A specific example is a line camera. Other examples of such a signal detector are described later in the context of specific detailed example implementations.

Another example of a signal detector that produces an interferogram from the interferometry output is an amplified balanced photodiode pair. Other examples of such a signal detector are described later in the context of specific detailed example implementations.

In some embodiments, there are multiple sample arms, and a respective interferogram is generated for each sample arm, reference arm combination.

In some embodiments, there are multiple reference arms, and a respective interferogram is generated for each sample arm, reference arm combination.

In some embodiments, there are multiple reference arms and multiple sample arms, and a respective interferogram is generated for each sample arm, reference arm combination.

There may be multiple sample arms, for example, where there are multiple reflectors at the sample location. Such sample arms may share common optical components in delivering reflections from the sample to the combiner, but the optical path lengths will be different. Some of the sample arms may be to subsurface reflectors.

For any cases where multiple interferograms are generated, these multiple interferograms are then used by the feedback controller 26 in generating the feedback 28 to control the material processor 10.

Recall that the interferometry output is based on a length of at least one optical path to the sample location compared to a length of another optical path. In some embodiments, the "another optical path" is simply a different optical path to the sample. Effectively, the two paths being compared by the interferometer in this case are two paths to different reflectors of the same sample. In this case, the imaging light will traverse the same optical path but for small differences between the locations of the reflectors at the sample location.

In some embodiments, the at least one path length is at least two path lengths to respective reflectors at the sample location, and the another path length is along a reference arm.

In some embodiments, the feedback controller is further configured to determine if the interferometry output initially comprises substantially only light reflected along a reference path (this reference path may be along a reference arm if there is one or along the sample arm) after which the interferometry output is based on the path length of a sample path compared to the path length of the reference path. This might occur, for example, when the sample location initially has only one reflective surface/subsurface (in no reference arm case) or no reflective surface/subsurface (in reference arm case), and then after material has been removed, at some point there is an additional reflective surface/sub-surface.

In some embodiments, the feedback controller is further configured to determine when the interferometry output makes a transition from comprising substantially only light reflected along a reference path (this reference path may be along a reference arm if there is one or along the sample arm) after which the interferometry output is based on the path length of a sample path compared to the path length of the reference path. The feedback controller generates at least one signal that influences at least one processing parameter of the material modification process based on the interferometry output taking into account the transition.

In some embodiments, the feedback processor performs an analysis based on the interferometry output to produce a depth measurement reflecting how deep the material processing beam has penetrated at the sample location. In some such embodiments, the feedback controller controls at least one processing parameter of the material modification process based on the depth measurement.

In some embodiments, the feedback controller performs an analysis based on the interferometry output and generates feedback control that controls the depth of processing (e.g. cutting) relative to an interface that is closest to the processing location.

In some embodiments, the feedback controller performs an analysis based on the interferometry output and generates feedback control that controls processing depth (e.g. cutting depth) relative to an interface that is beyond the current processing depth.

It is to be understood that any processing parameter of the material modification process may be controlled by the feedback controller. Specific examples include:

- on/off state of the material processing beam;
- the average power of the material processing beam;
- the pulse duration of the material processing beam;
- the peak intensity of the material processing beam;
- the density of the material processing beam;
- the energy of the material processing beam;
- the particle species of the material processing beam;
- the wavelength of the material processing beam;
- the pulse repetition rate of the material processing beam;
- the pulse energy of the material processing beam;
- the pulse shape of the material processing beam
- the scan speed of the material processing beam;
- the focal diameter of the material processing beam;
- the focal position of the material processing beam;
- the spatial pattern of the material processing beam on the sample;
- the material feed rate;
- the cooling media flow rate;
- the cover/assist gas flow rate;
- the cover/assist gas pressure;
- the cover/assist gas blend;
- the arc welding process parameters (such as voltage, current and wire feed rate);

and the additive material feed rate (e.g. in brazing).

In a specific example, the feedback controller controls at least one processing parameter of the material modification process based on the depth measurement by controlling the material modification source beam to be off when the depth measurement indicates a specified depth.

In some embodiments, the feedback controller has an interferogram processor that performs an analysis based on the interferometry output to produce an indication of when the material modification source beam has penetrated to a specified depth that may, for example be absolute, or relative to a surface or interface associated with the material. In some such embodiments, the feedback controller controls the material processing beam source to turn off the material processing beam based on the indication of when the laser has penetrated to the specified depth.

In some embodiments, the feedback controller has an interferogram processor that performs an analysis based on the interferometry output to produce an indication of the proximity of the region of the material currently being modified to other regions of the material.

In some embodiments, the feedback controller has an interferogram processor that performs an analysis based on the interferometry output to produce an indication of the remaining amount of material to be penetrated.

Figure 6:
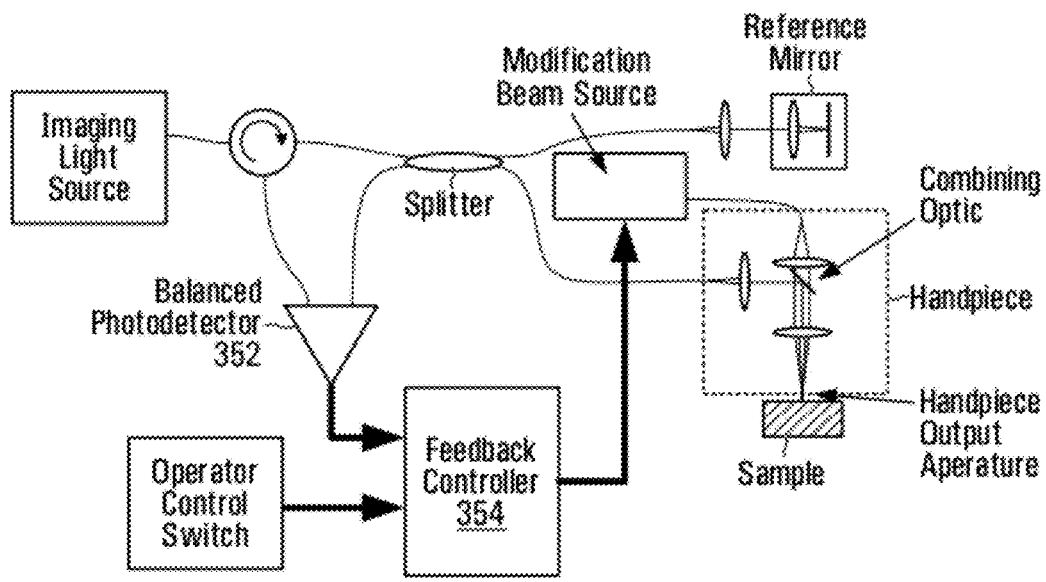
FIGS. 6 and 7 are block diagrams of one and two channel material processing systems featuring feedback control from an inline coherent imaging system and a balanced photodetector.
Figure 7:
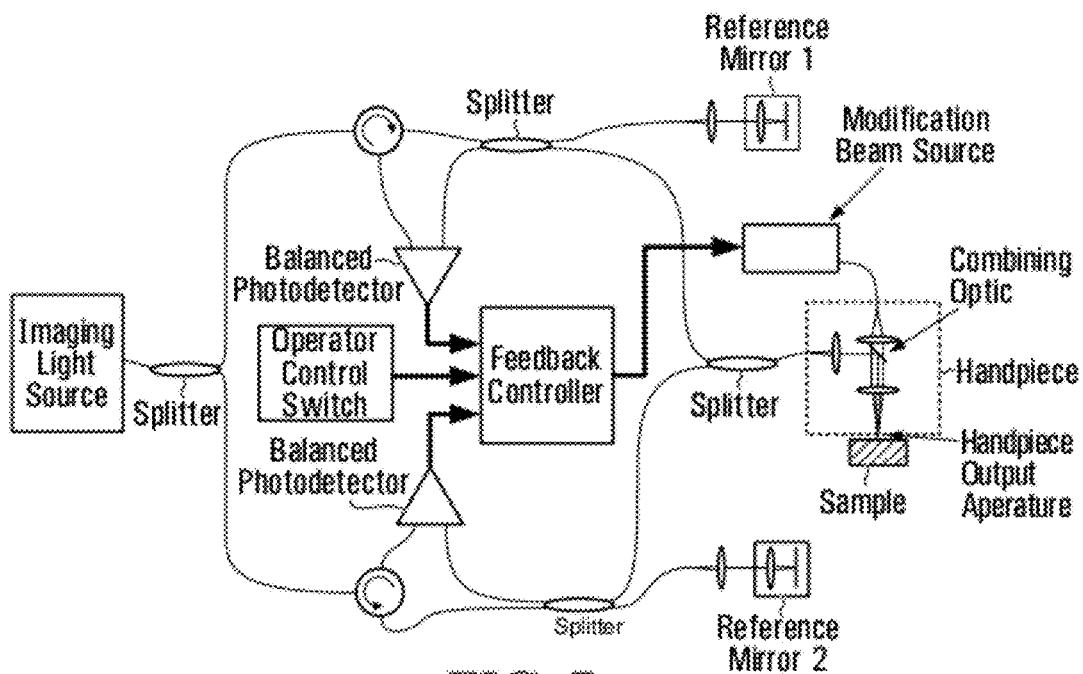

In some embodiments, an interferogram processor performs analysis based on the interferometry output to produce an indication of when material is present at a specified depth, and the feedback controller controls the material processing beam source to turn on the material processing beam based on said indication. FIGS. 6 and 7 are two specific examples of such a system which features an optical circulator and balanced photodetector. These figures are described below.

Figure 2:
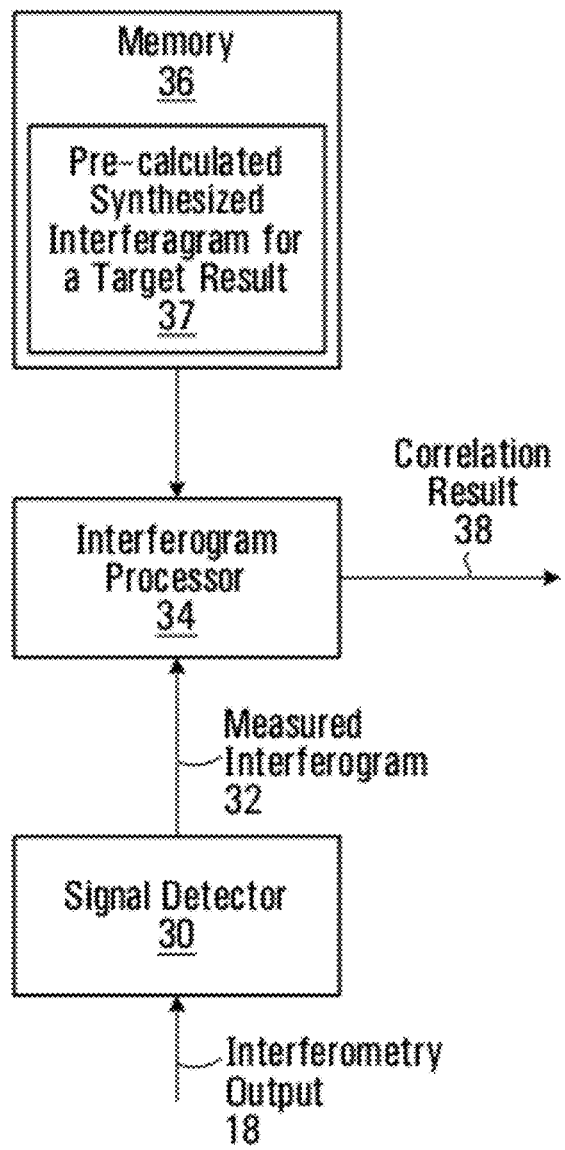
FIG. 2 is a block diagram of an example implementation of the feedback controller of FIG. 1.

FIG. 2 shows a partial example implementation of a feedback controller. Shown is a signal detector 30 that receives the interferometry output 18 and generates a measured interferogram 32. An interferogram processor 34 receives the measured interferogram 32. A memory 36 is provided in which is stored a pre-calculated synthesized interferogram 37 for a target result. The interferogram processor 34 processes the measured interferogram together with the pre-calculated synthesized interferogram 37 to produce a correlation result 38. The feedback controller controls at least one processing parameter of the material modification process based on the correlation result that is a measure of similarity of the measured interferogram 32 and the synthesized interferogram 37.

The pre-calculated synthesized interferogram for a target result is pre-calculated such that it is immediately available for correlation with the measured interferogram. It is synthesized in the sense that it is determined from calculations alone; no optical signals are involved in its generation.

In some embodiments, the pre-calculated synthesized interferogram for a target result is an estimate of what is expected when a specified depth is reached by the material processing beam.

In some embodiments, the interferogram processor produces the correlation result by multiplying the measured interferogram by the pre-calculated interferogram on a detector element basis and then summing.

In some embodiments, at least one of the pre-calculated synthesized interferogram and the measured interferogram is shaped to compensate for at least one of:
spectrometer alignment;
spectrometer grating angle nonlinearity;
imaging distortion from imaging optics in the spectrometer;
wavelength to wave number/frequency re-sampling;
finite size of detector active area;
spectral envelope shape;
dispersion mismatch; and
another non-ideality contained in the interferogram that degrades image quality.

Compensation may, for example, be achieved through a controlled modulation of the complex phase and amplitude of the individual elements of the synthesized interferogram. The amount of modulation can be determined from at least one of experimental calibration of apparatus, mathematical modelling of optical propagation, theoretical analysis of system response, and a combination of the above. The exact method depends on the specific non-ideality to be compensated for.

A specific example is dispersion. For a fixed dispersive element, the relative phase lag/advance of each wavelength arising from the dispersive terms of the material can be added to each element in the synthesized interferogram. Progressive dispersion (i.e., dispersion intrinsic in the sample) can also be compensated for because the synthetic interferogram can be calculated differently for each depth to be measured.

In some embodiments, the correlation result is processed to identify when a specified depth has been reached by the material processing beam. This can, for example, be achieved by determining when the correlation result exceeds a threshold.

In some embodiments, the system further includes an interferogram synthesizer that synthesizes the pre-calculated synthesized interferogram.

Another embodiment provides a feedback control system for use with a material processing system that implements a material modification process, the material processing system having a camera port. Such a feedback control system comprises the functionality of FIG. 1, not including the material processor. In this case, the optical interferometer 22 interacts with the material processor 10 through a camera port, not shown. The feedback 28 is provided from the feedback controller 26 to another input of the material processor 10.

The embodiments described above can, for example, be used to measure the geometry, morphology, optical scattering and/or composition of a material before, during and/or after processing by a material modification beam, such as a laser. In some embodiments, feedback information about the geometry/morphology/composition of the material may be provided (such as, hole, cut, static or dynamic subsurface features, and/or melt pool depth) and such information may be used, either directly or indirectly, to control a material modification process, such as a laser modification process.

In some materials, the systems described herein may sense elements of the geometry of the material being worked on and their position in relation to other material geometry elements that are below the surface with which the modification beam is interacting. In some embodiments this information is used to guide the modification to within prescribed margins of subsurface geometry, even where the precise location of said geometry may have been previously unknown and/or uncharacterized. In some embodiments, the depth of a laser cut into bone is measured such that laser modification may be ceased some distance before it penetrates a subsurface layer of bone of interest. This may be useful for providing safe margins in laser surgery. In some embodiments, such margins/feedback are achieved using analysis of the metrology data, in some embodiments, using techniques that are manual, automatic or some combination of the two.

In some embodiments, apparatus, methods and systems are provided that sense changes at the subsurface level, such as but, not limited to, temperature changes, state changes, fluid flow, and/or pressure waves, that can, in some embodiments, be further used to inform the laser exposure process. In some embodiments, these changes are determined based on a comparison/analysis of multiple measured interferograms. The phase of the interferogram is sensitive to movement in the sample on the order of a few nanometers. Slight temperature, pressure, flow and state changes cause movements of the tissue that change this phase. Also, coherent images have a characteristic "speckle pattern" that is the partial result of the microscopic/nanoscopic components of the sample creating an internal interference pattern. This speckle pattern is also extremely sensitive to the changes mentioned above. In some embodiments, subsurface changes are observed during laser processing of varying rates by analyzing the frequency of the change in speckle pattern.

In some embodiments, the apparatus described is used to track elements of the melt pool in the process of laser welding. Persons of skill in the art will appreciate that melt pool (and/or keyhole) stability and penetration depth can be an indicator of the quality of a laser weld. Some embodiments are used to measure these and/or other indicators and, in some embodiments, for the purposes of disciplining the welding process, aiding welding process development or to produce quality assurance data for the whole or part of the process.

In some embodiments, the imaging light source is a light source with a spectrum centered at a wavelength, $\lambda_o$, that in some embodiments may be between 300 and 15000 nm and may have a width, $\Delta\lambda$, that can provide an axial resolution, $\delta z$, that may be represented by the following relationship:

$$\delta z = \frac{2\ln 2}{\pi} \frac{\lambda^2}{\Delta\lambda}$$

In some embodiments, the imaging light source may be: superluminescent diodes, laser diodes, light emitting diodes, ultrafast optical oscillators, semiconductor optical amplifiers and halogen lamps; however, persons of ordinary skill will understand that other appropriate light sources may be used. In other embodiments, the light source may include a superluminescent diode (SLD), in some embodiments having an emission spectrum ranging from 1100 nm to 1400 nm or, in alternative embodiments a Ti:AlO$_3$ oscillator, in some embodiments having an emission spectrum ranging from 750 nm to 900 nm. In some embodiments, depending on the subsequent detector technology chosen, a light source that has a narrow instantaneous linewidth that is rapidly swept across the spectral band defined by $\lambda_o$ and $\Delta\lambda$ may be used instead of or together with the other sources mentioned.

In other embodiments, additional light sources may be included for material modification. In some embodiments, these sources may have spectra in the region of 200 nm to 15000 nm and can, in some embodiments, be continuous or, in other embodiments, be pulsed in their emission. In embodiments having pulsed emissions, pulse energies ranging from 1 nJ to 1 MJ and pulse durations ranging from 1 fs to 30 minutes may be used.

In some embodiments a signal detector (which may be a single detector or combination of detectors) senses the intensities of the different wavelengths of light of interest. This may involve the use of diffractive elements to disperse the spectrum spatially over a detector array. Alternatively, the signal detector may be a balanced or unbalanced photodetector where the timing of the arrival of components of the spectrum may be known to be simultaneous or dispersed in time.

Electronics may be included that can measure and interpret the detected signal. At this point in the information processing chain, the signal is not optical anymore. In some embodiments, these may include, but are not limited to, on-board camera hardware, frame grabbers, field programmable gate arrays, application-specific integrated circuits, personal computers, data acquisition cards. The electronics hardware may be chosen to complement the feedback schema and methods or algorithms employed.

Some embodiments include software and/or hardware stored on an appropriate computer readable storage medium implementing methods or algorithms capable of identifying the position bottom of the hole and/or subsurface interfaces and/or changes of interest in the imaging data and can calculate metrics and control parameters based on their positions, for example their absolute or relative positions.

Figure 3:
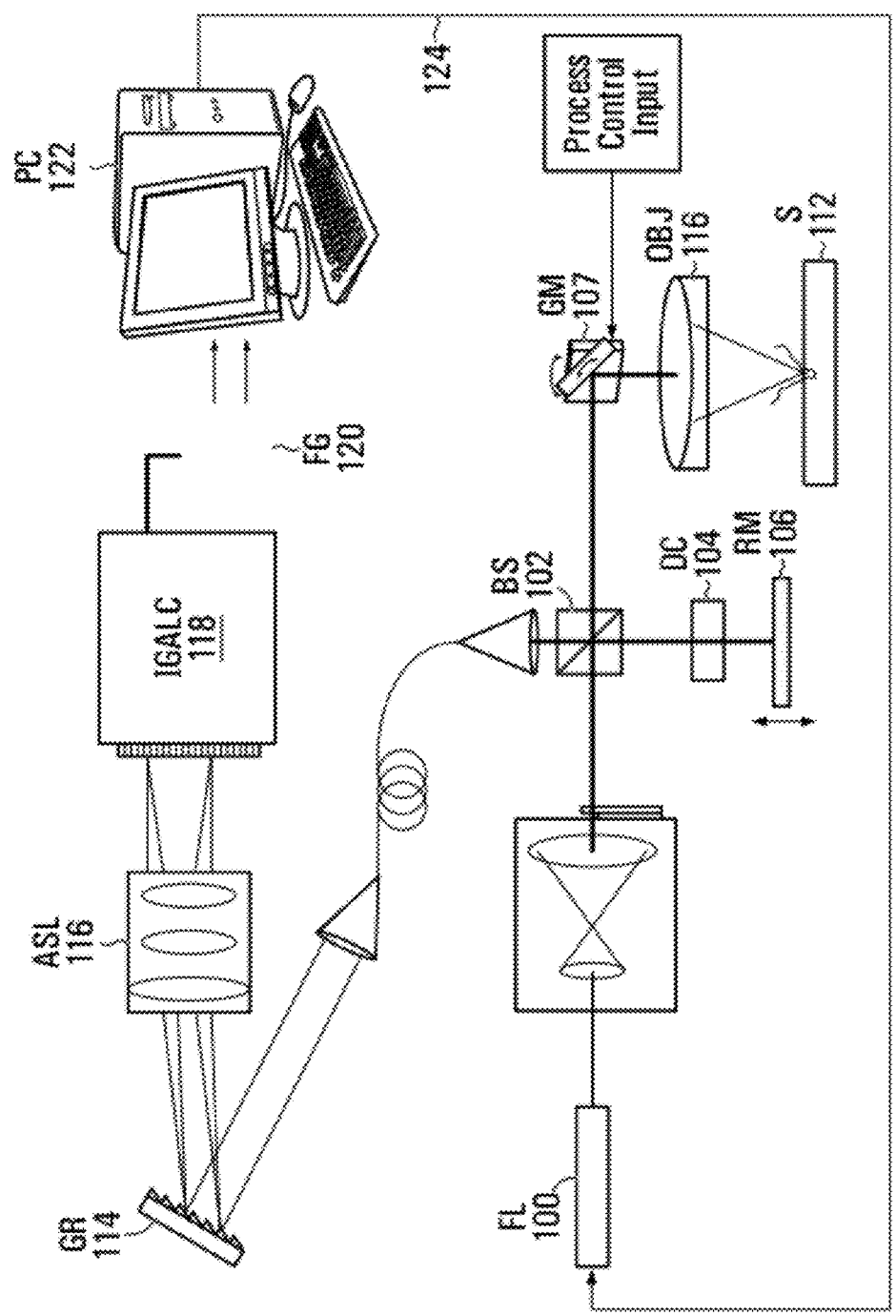
FIG. 3 is a block diagram of a block diagrams of a material processing system featuring feedback control from an imaging system in which the material modification beam source also functions as the imaging light source.

FIG. 3 is a block diagram of an apparatus in which a modification laser (FL) 100 also serves as the imaging light source. This results in the imaging and processing beam alignment being automatic. In contrast, the embodiments of FIGS. 1 and 4,5,6,7,14,17,18,19, feature a material processing beam source and an imaging optical source. A free-space Michelson interferometer is used that includes a beam splitter (BS) 102, dispersion compensator (DC) 104, a reference mirror (RM) 106, galvanometer mirrors (GM) 107 and an objective 116 to focus the light onto the sample 112. Detection is accomplished by a spectrometer comprising a grating (GR) 114, lens (ASL) 116 and photodetector array (IGALC) 118. The PC 122 and frame grabber (FG) 120 implement the electronics and algorithm components of the apparatus, methods and systems described herein. The PC 122 controls the modification laser 100 and/or another aspect of the modification process through feedback path 124, and in this case functions as the feedback controller.

Figure 4:
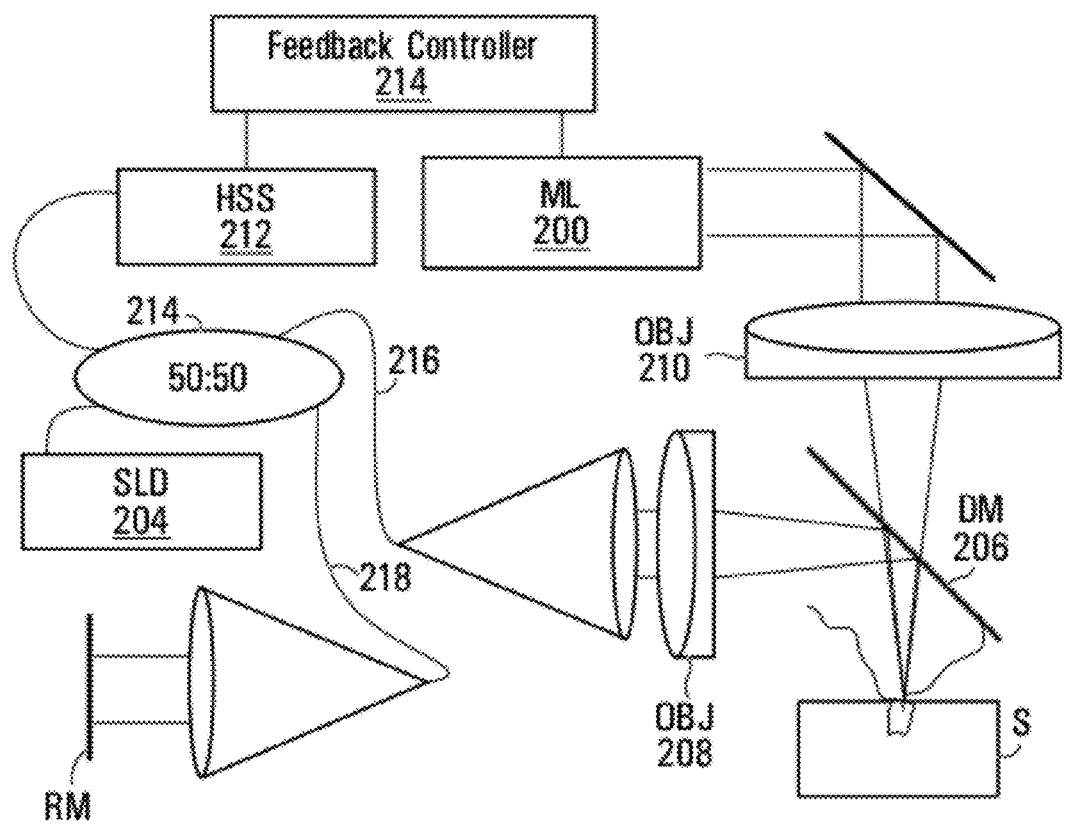
FIGS. 4 and 5 are block diagrams of material processing systems featuring feedback control from an inline coherent imaging system.

FIG. 4 is a block diagram of a first detailed implementation. In this embodiment, separate modification (ML) 200 and imaging (SLD) 204 light sources are shown. In this embodiment, the two light paths are combined by a dichroic or other combining optic (DM) 206 after independent focal objectives 208,210. In this embodiment, the interferometer can be built in single or, in other embodiments, in multi-mode optical fibre. Detection is accomplished by means of a high speed spectral detector (HSS) 212. While the embodiment shown displays a 50:50 power splitting ratio 214 between sample arm 216 and reference arm 218, in other embodiments other splitting ratios in the interferometer are possible and may depend on the availability of optical power and/or the need for detection sensitivity. In some embodiments, other interferometer configurations e.g. Mach-Zehnder, Sagnac, common path, etc. may be possible. While, in this embodiment, DM 206 is shown to reflect the imaging light and transmit the modification light, the reverse can additionally be possible. In some embodiments, the combination of the beams via polarization-sensitive or neutral reflection optics can occur. A skilled person will understand that detection, processing and feedback electronics are omitted from the embodiment shown in this figure and such processing steps may be performed within the feedback controller. Feedback controller 214 receives the output of the HSS 212 and controls the modification laser 206 and/or some other aspect of the material modification process.

Figure 5:
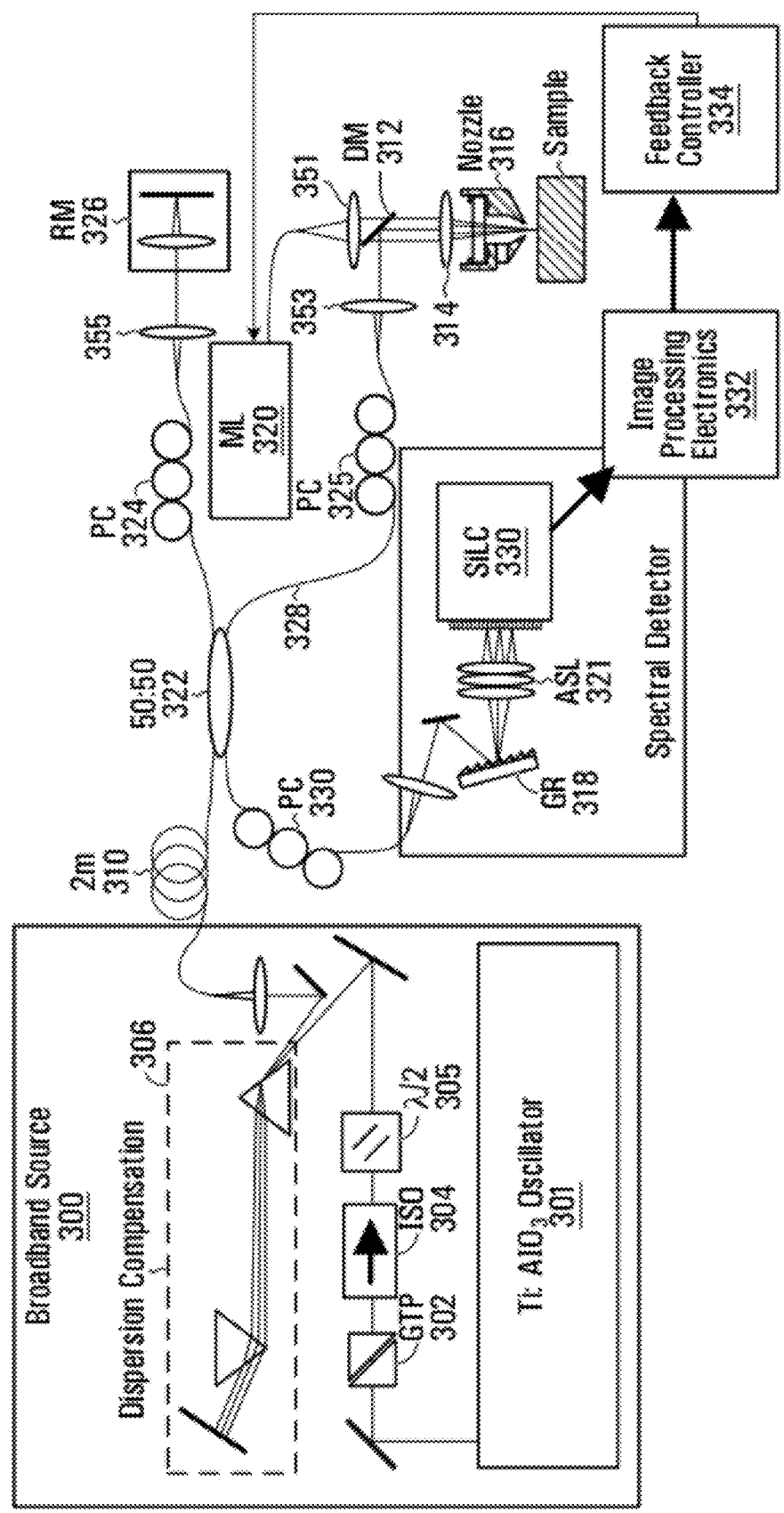

FIG. 5 is a block diagram of a second detailed implementation. In this embodiment, a high power broadband source is created by coupling short, dispersion-optimized pulses output by broadband source 300 into a length of single mode optical fiber 310. This results in an expansion of spectral bandwidth, in some embodiments, on the order of a factor of 6, though in other embodiments, more or less broadening is possible. The embodiment shown here features a $Ti:AlO_3$ laser source 301 that operates in the region of 650 to 1100 nm. In other embodiments, spectral ranges from 300 to 15000 nm from other optical imaging sources are possible. In this embodiment, a Glan-Taylor polarizer (GTP) 302, Faraday optical isolator (ISO) 304, half-lambda waveplate polarization control 305 and Fork prism dispersion compensation 306 are shown. In other embodiments, other broadband sources (such as superluminescent diodes, other lasers and/or other broadening methods) may be substituted for the broadened $Ti:AlO_3$ laser source.

In this embodiment, the modification laser (ML) 320 passes through collimator 351 and the imaging beam passes through sample arm collimator 353 after which the modification laser beam and the imaging beam are combined by an optic component (DM) 312 before they are focused by a common focal objective 314.

In such embodiments, the lens may be achromatic, aspheric and/or conical (i.e. axicon). This beam combination may be focused through an optional nozzle 316 that can be used to apply assisting fluids (e.g. compressed gas, e.g. water spray) to the modification process. The nozzle spray may also be independent from the optical beam; i.e. the two are delivered to the sample from different points. The Michelson interferometer includes the 50:50 splitter 322 (though in other embodiments, other splitting ratios may be used), reference arm collimator 355 and reference mirror 326. Also shown are polarization controllers 324,325,330. The spectral detection in this embodiment involves a fiber-coupled reflective grating spectrometer 318. In some embodiments, an additional mirror in front of the lens (ASL) 321 can allow the beam to approach and leave the reflective grating 318 as close to the Littrow configuration as possible, improving diffraction efficiency. In some embodiments, a transmission grating and/or multi-grating, and/or Fabry-Perot spectrometer may be used. A silicon line camera 330 produces an interferogram that is passed to image processing electronics 332, the output of which is passed to feedback controller 334. Feedback controller 334 produces a feedback 336 to control the modification laser 320 or some other aspect of the modification process.

Proper alignment and beam shaping of the modification and imaging light can be beneficial to the quality and usefulness of the imaging data and feedback control. In some embodiments, it can be desirable to image down into a high aspect ratio feature such as a hole being drilled. In such cases, an alignment method (in some embodiments using a dichroic mirror beam combiner for imaging and modification light) provides that the two beams meet on the reflective surface of the combiner at substantially the same point. In such embodiments, adequate beam control of the two beams (one or more mirrors) is beneficial. With the two beams emanating from the same point of the combining optic, they can then be focused through a suitably achromatic (or other design) lens. In some embodiments, the use of an array detector or a pinhole (in some embodiments made by the modification laser itself) located at the focal plane of the lens can aid the adjustment of the combining optic, so that both beams focus on substantially the same spot. This can, in some embodiments, be used to match the reference arm length of the interferometer to place the center of the focal volume at a desired position in the imaging field of view. This position may be selected on the basis of the modification application at hand and may additionally be adjusted throughout the modification process. In other embodiments, such as those where a common focal lens is not used, it may be beneficial to have the central ray for all beams coincident on the combining optic. It may additionally be desirable to shift the focal positions of the imaging and modification beams independently from one another, to more efficiently image/modify depths of choice. In some embodiments, this may be accomplished by adjusting the divergence of the imaging or modification beams before they reach the common focusing lens. For example, the divergence of the imaging beam may be increased by decreasing the distance between the sample arm collimator lens and the fiber tip.

The focal spot size of the imaging and modification beams can have an impact on the quality of the imaging results. A careful consideration of morphology aspect ratio and imaging beam numerical aperture should be made. In embodiments where an imaging beam is much smaller than the hole transversely, the resulting imaging data may give a clear signature of the bottom of the hole and interfaces below it. However, in such embodiments, the practical imaging range may be limited by the short Raleigh range present in a high numerical aperture beam. In some embodiments, a numerical aperture is employed to reject signals that emanate from the sidewalls of the hole. In such embodiments, if portions of a hole/incision periphery are illuminated in a sample that is (quasi)transparent and captured by the imaging system, the corresponding signals may complicate the imaging data and may make it more difficult for an automatic algorithm to use the data for feedback. However, in embodiments where the sample is nontransparent, it may be beneficial to have some illumination of the sidewalls as such a signal can provide information about cut width, recast deposition and the depth of the bulk material.

In some embodiments, the optical components are matched (in some embodiments the group delay and higher order dispersion terms) in the sample and reference arms to reduce any dispersion mismatch between the two arms. This may improve axial imaging resolution. It may also be beneficial to change this dispersion compensation in the reference arm to match additional dispersion caused by material present in the sample.

Dispersive mismatch may be intentionally added to the interferometer and image processing algorithms modified to increase the effective imaging range of the system using dispersion-encoded full range techniques such as those described by Hofer et al (Bernd Hofer, Boris Povazay, Angelika Unterhuber, Ling Wang, Boris Hermann, Sara Rey, Gerald Matz, and Wolfgang Drexler, Optics Express 18, 4898-919 (2010) hereby incorporated by reference in its entirety).

When imaging into a sample, the degree of carbonization that may be created by the modification laser can be a consideration. Lasers that cause large amounts of charring can reduce the imaging depth (and the advance notice for perforation etc.). Selecting lasers with reduced carbonization (ultrashort pulses, center wavelengths of 3000 nm, 9600 nm etc.) may be beneficial.

Methods and algorithms may be used to process the raw data and/or provide feedback parameters, and may include steps of background spectrum subtraction, resampling/interpolation between the spectrometer pixels, wavelength and/or frequency space, noise floor equalization, fast Fourier transformation, Kasai autocorrelation/Doppler shifting and/or other calculations based on the phase and/or separation of interference fringes. Such methods may be implemented in hardware and/or software running on a processor or processors. In some embodiments an analysis of a speckle pattern and/or changes thereof is employed to indicate tissue differentiation, temporal heating dynamics and/or other characteristics of the sample. These analyses may, for example, be performed by calculating the spatial or temporal variation of the speckle and its amplitude. Such methods and algorithms are in some embodiments used to assess the depth of thermal damage that has occurred, is occurring and/or will occur in the future. Methods of signal extraction that forgo many of the previous steps are also possible. In one embodiment, a set of homodyne or heterodyne waveforms can be pre-calculated based on one or a plurality of simulated optical path length differences, nonlinearities/nonidealities in the spectrometer, wavelength to wavenumber/frequency conversions, single or multi-order dispersion mismatch in the interferometer, Doppler shifts, non-ideal spectral shapes and other adjustments to the imaging data. Sets of such homodyne/heterodyne waveforms can be multiplied against the data collected by the hardware or software to determine imaging information at one or more of the voxels in the imaging space. This result may be obtained due to the orthogonality and/or quasi-orthogonality of the different interference fringe frequencies present in the acquired data. Detailed examples of this approach are described below. In some embodiments, methods and algorithms may provide computational savings when compared to other methods that use, for example, fast Fourier transformation. This may be desirable for real-time feedback applications where a fast response generally provides improved outcomes from the process. Processing can, in some embodiments, use the full spectrum data set, or, in other embodiments, use a subsection of the data set. In embodiments using a subsection of the data set, this can reduce processing time, and can provide lower axial resolution, which may be useful for a variety of feedback purposes. Homodyne/heterodyne filtering can also have applications in general image processing in the Fourier domain variants of Optical Coherence Tomography where the large number of post-processing and/or real-time calculations (including interpolation, digital dispersion compensation, spectral shaping etc.) may encumber the computational efficiency of the system. Though not limited to this case, such embodiments may be useful in situations where imaging is targeting a subsection of the full depth of field.

In some embodiments, it is beneficial to obtain the homodyne waveform(s) by measuring a real interferogram when an interface is at specific depth(s) in the image. The complex homodyne waveform(s) may be obtained by shifting the interface optomechanically by moving the interface, optically with phase shifting optics and/or through digital processing, which may use Hilbert transforms and other methods. Additional shaping steps (which may include denoising, averaging, envelope shaping) may then be applied to further optimize these waveforms. In some embodiments, the spectral profile is shaped through digital, optical (including, but not limited to mechanical blocking, polarization adjustment, neutral density filtering, interference filtering, Fabry-Perot elements) or other methods to change the effective point spread function of the algorithm to be more optimal for feedback use. For example, in one embodiment, a non-Gaussian spectral profile may be applied digitally to the homo/heterodyne waveform to create additional lobes in the point spread function. These lobes may be engineered to provide "early warning" signals or structured local/global minima and maxima for the feedback algorithm to settle in.

In embodiments where the sample is transparent or semitransparent material, the space originally occupied by the sample bulk can be filled with air as material is removed by a modification laser. In embodiments where the sample has an optical index of refraction that is greater than air, as material is removed, the optical path length to any subsurface reflectors may be reduced. This has the effect of changing apparent depth of said reflectors (in some embodiments, closer to and, in other embodiments, further from, the zero optical path length difference point) at a rate that is generally related to the linear removal rate of material and the optical index. In embodiments using an M-mode image ("motion-mode", shown in later examples), the superficial interface and the subsurface interface trend towards each other with continuing material removal until their eventual meeting at the point of perforation. Sensing the separation of the two interfaces and using such separation as an input into a feedback method or algorithm may be used to represent a surgical margin to be preserved/monitored. In the Fourier domain, these two interfaces may appear as two separate frequencies that are approaching each other. Apparatus and systems implementing methods and algorithms that sense the change in frequency difference between the two signals can communicate such information to a process controller and/or user that can control the cut.

The same technique may be applied to any material processing system where multiple interfaces indicate specific features of the sample, and it is desired to control the material processing based in part on depth measurements to those features.

Measuring the relative slopes can measure the effective optical index of refraction of the material being removed. This can be an indicator of the material's composition which can be useful information to feed back. In some embodiments, it may be possible to detect when the modification laser has perforated one material and started on the next by tracking a change in the relative slope.

These same principles may also be applied to situations where the material that fills the hole is water and/or materials other than air.

In some embodiments, a circulator is added to the interferometer between the source and the fiber splitter. In some embodiments, a balanced photodetector (in addition to or instead of the spectrometer) is used to detect the interference fringes that are created as the interface arrives at the zero optical path length difference point of the interferometer. In such embodiments, the balanced photodetector may have higher measurement rates than an array of detectors or the sweep rate of a Fourier Domain Mode Locked laser (or other swept source), and improve feedback response. This can provide fast, simple and inexpensive feedback to detect the arrival of an interface at a certain depth. In some embodiments, this can be used to detect when material is present at a certain distance away from the system optics. It is known to those skilled in the art that the effectiveness of a focused laser beam may depend on the distance between the focus and the material to be modified. This embodiment could be used to provide feedback to the material processing system with picosecond accuracy. In some embodiments, this feedback may be used to permit emission of modification energy only when material is present in a selected depth zone (SDZ) that may, in some embodiments, be related to the focal zone of the modification laser. The SDZ position and thickness may be tuned through control of the imaging light source spectrum and the reference arm length. This tuning may be factory set and/or may be dynamically set by the operator. In some embodiments, the imaging and modification beams may be coupled to a handpiece and the SDZ configured to be co-located with the focus of the modification beam some distance away from the distal end of the handpiece. In this way, the handpiece acts as an optical analogue to the traditional surgical scalpel. The SDZ would be analogous to the edge of the tip of the scalpel blade and may be used to incise material that is located at the SDZ.

This may have a number of advantages including, but not limited to providing a tactile interface that is familiar to surgeons, reducing total laser energy use, reducing total laser exposure to the material and/or patient. It is known to those skilled in the art that some kinds of laser modification of materials may generate plasma above the material that scatters and/or absorbs laser energy. While such plasma is present, further applied energy may not have the desired modification effect and may contribute to larger heat affected zones. In some embodiments, the plasma may block imaging light, thus preventing reflections from the material from triggering the feedback system until said plasma has dissipated. This provides the advantage of limiting modification application energy from being applied unless the plasma conditions near the sample are favourable.

In some embodiments, the feedback control may be used in conjunction with an operator switch (such as a foot pedal) such that the operator can indicate his/her consent to emit modification energy when the optoelectronic feedback conditions are met.

In some embodiments, the feedback control may be effected on the modification energy source by way of optical pulse picker, digital seed pulse control, pump modulation, shutter, electro-optic modulator, Pockles cell and/or acousto-optic modulator.

A specific example is depicted in FIG. 6 which shows optical circulator 350 and balanced photodetector 352. The output of the balanced photodetector 352 goes to feedback controller 354 which controls the modification beam source.

A two channel version is depicted in FIG. 7. The path length down the sample arm of one channel is approximately the same as that of the reference arm, but very different from their counterparts in channel 2 (and further channels if present) to avoid cross talk in the interference signal.

The embodiments of FIGS. 6 and 7 are examples of systems that can be used to detect when material is present at a specific depth. (10a). Reflections of imaging light emanating from the sample and captured by the system optics will generate an interference signal at the (balanced) photodetector when the reference and sample optical path lengths are matched.

Optical dispersion induced by a sample being measured can have an adverse effect on the axial resolution of coherent images. In some embodiments, the sample can induce a wavelength dependent phase shift on the interference pattern that may be dependent on the depth that the light has propagated in the sample. A homodyne/heterodyne algorithm, for example, as described above, can be used to compensate for these effects. The dispersion coefficients of the materials in the sample can, in some embodiments, be calculated a priori or, in other embodiments, be determined iteratively. One may begin by assuming that the phase shifts induced by the sample increase linearly with increasing penetration into the sample. In this way, each color (i.e. pixel measurement) on the detector may have a certain phase shift dictated by which color it is and what depth in the sample the signal is returning from. If the color measured by each pixel and the depth associated with each hetero/homodyne waveform can both be known a priori, this distortion can be estimated and calculated a priori and may be incorporated into the heterodyne/homodyne waveforms that are multiplied against the signal that is measured by the detector(s). Alternatively, measurement of the optical signal propagating through the system may also provide dispersion mismatch information used for compensation. A hetero/homodyne waveform lookup table can be prepared before the imaging session. In such embodiments, the dispersion correction can be applied with zero additional real-time computing load.

Interferogram Correlation Thresholding Apparatus

Figure 8:
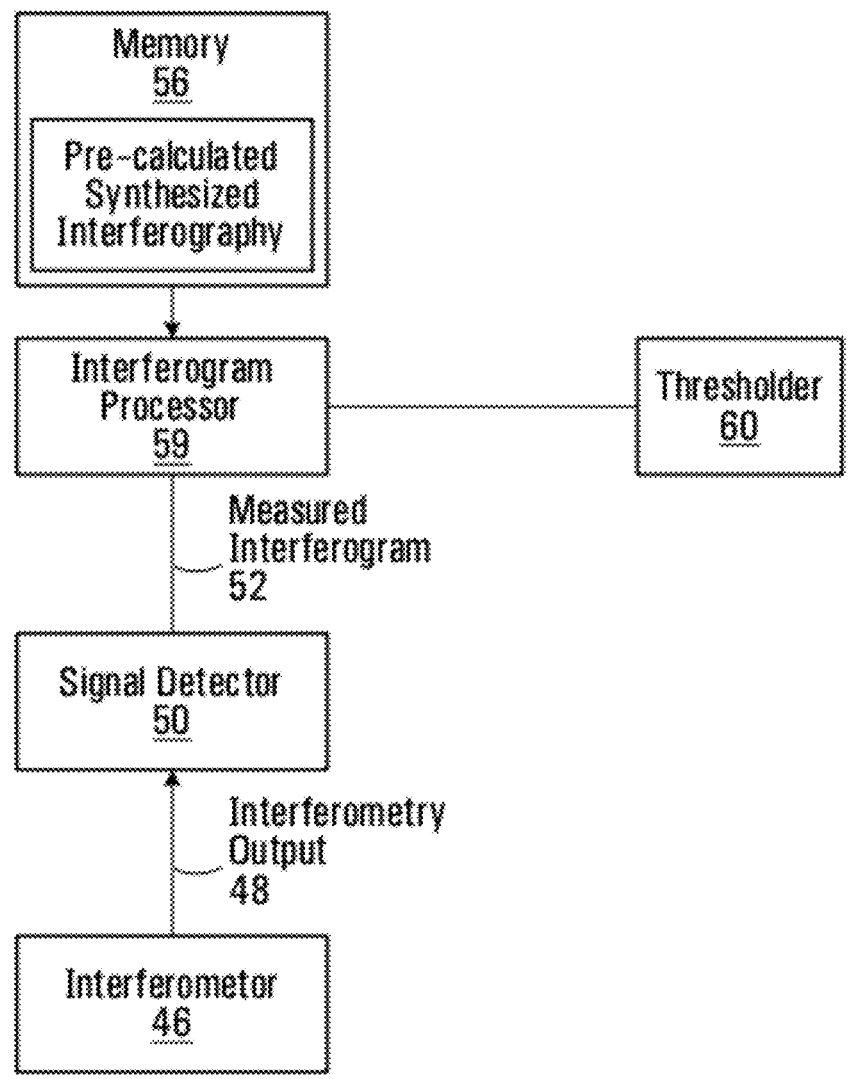
FIG. 8 is a block diagram of an apparatus for processing an interferometry output using a pre-calculated synthesized interferogram.

Referring now to FIG. 8, shown is an interferogram correlation thresholding apparatus provided by an embodiment of the application. Shown is an interferometer 46 that produces an interferometry output 48. There is a signal detector 50 that receives the interferometry output 48 and generates a measured interferogram 52. An interferogram processor 54 receives the measured interferogram. A memory 56 is provided in which is stored a pre-calculated synthesized interferogram. The interferogram processor 54 processes the measured interferogram together with the pre-calculated synthesized interferogram to produce a correlation result 58. A thresholder 60 is configured to determine when the correlation result satisfies a threshold.

The pre-calculated synthesized interferogram for a target result is pre-calculated such that it is immediately available for correlation with the measured interferogram. It is synthesized in the sense that it is determined from calculations alone; no optical signals are involved in its generation. Details of how this interferogram can be adjusted a priori to perform various compensations have been provided above.

In some embodiments, there is a respective pre-calculated synthesized interferogram for each of a plurality of target results. The interferogram processor 54 processes the measured interferogram together with each of the pre-calculated synthesized interferogram to produce a respective correlation result. The thresholder 60 determines when each correlation result meets a respective threshold.

In some embodiments, the pre-calculated synthesized interferogram is an interferogram that is an estimate of what is expected when the target result is achieved by a material modification beam at a sample location, and the measured interferogram is in respect of a sample location. The interferogram processor produces the correlation result by multiplying the measured interferogram by the pre-calculated synthesized interferogram on a per wavelength basis and then summing.

In some embodiments, at least one of the pre-calculated synthesized interferogram and the measured interferogram is shaped to compensate for at least one of:
  spectrometer alignment;
  spectrometer grating angle nonlinearity;
  imaging distortion from imaging optics in the spectrometer;
  wavelength to wave number/frequency re-sampling;
  finite size of detector active area;
  spectral envelope shape;
  dispersion mismatch; and
  another non-ideality contained in the interferogram that degrades image quality.

Some embodiments feature an interferogram synthesizer that calculates the pre-calculated synthesized interferogram.

In some embodiments, the target result is a specified depth reached by the material modification beam.

In some embodiments, the apparatus has a feedback controller that controls a material modification source to turn off the material modification beam when the correlation result meets a threshold.

In some embodiments, the apparatus has a feedback controller that controls a material modification source to turn on the material modification beam when the correlation result meets a threshold.

In some embodiments, the apparatus has an interferogram synthesizer that synthesizes the pre-calculated synthesized interferogram.

Automatic Guidance of Laser Cutting of Hard Tissue with Inline Coherent Imaging

In some embodiments, one or more of the systems and methods described above, and related software stored on computer storage media are configured for automatically and/or manually guiding the removal of hard tissue by laser irradiation.

In some embodiments, the basis of the imaging technology is spectral domain optical coherence tomography, but in other embodiments, other variants (swept source OCT, optical frequency domain imaging, time domain OCT etc.) are employed. It is noted that the motion artifacts generated in SDOCT are favourable and SDOCT usually has acceptable rejection of the intense machining light.

In some embodiments, coherent imaging is used to rapidly measure depth and reflectivity information from a sample that is being machined with a laser. The imaging beam is often able to see through the ejecta, plasma, intense imaging light and beyond the modification zone. This allows the identification and tracking of subsurface geometry that, in some embodiments, is then used as a reference to spare thin layers of tissue.

The combination of imaging and machining light is accomplished, for example, with a dichroic mirror, but may also be achieved with polarization and other techniques known to those skilled in the art. Virtually any modification laser (250-10600 nm spectra, CW, µs, ns, ps, fs durations) can be used in this way. This may permit the tailoring of the machining laser to the application or the use of existing infrastructure/FDA approvals.

Other useful applications of the imaging system when integrated into a machining platform are autofocus, permanent therapeutic records and (with the addition of scanning optics) pre-treatment planning and post-treatment confirmation.

Some embodiments employ a streamlined image processing algorithm that uses a lookup table for hetero/homodyning in lieu of more complex operations that require interpolation, digital dispersion compensation, fast Fourier transforms etc.

Other embodiments feature the inclusion of one or more of scanning mirrors, more complicated machining sources, gas assisted cutting, more performant spectrometer designs, etc.

Coaxial imaging of laser machining processes with SDOCT provides useful information for measuring critical parameters for process development, such as etch rate and morphology relaxation, in industrial materials. In cutting tissue such as bone, SDOCT has similar benefits. To demonstrate, an SDOCT system based on a 100 fs mode locked Ti:AlO$_3$ oscillator @ 805 nm (Coherent Mira 900) broadened in single mode optical fiber was used. With a high speed CMOS spectrometer and fiber based Michelson interferometer, the imaging system provides <5 µm axial resolution (in air) and >100 dB sensitivity measured at 150 µm with a 1.5 µs (measured) integration time at a maximum line rate of 312 kHz. Images were processed in LabVIEW on 4 cores of a PC (and/or other software environments) using background spectrum subtraction, Gaussian spectral shaping, cubic spline interpolation, FFT and noise floor equalization. Other processing techniques and methods (mentioned in this description) have also been applied.

For machining in these experiments, a 100-200 ns (FWHM) pulsed fiber laser was used (IPG YLP-100-30-30-HC) with an average power at the sample of 23 W at 1070 nm and repetition rates from 30-80 kHz. The machining and imaging beams were aligned via a dichroic mirror and focused together via a single 50 mm achromatic lens. Fiber collimators were chosen such that both imaging and machining focal diameters were approximately 20 μm ($1/e^2$) with depths of focus of 500 and 340 μm respectively. Having the same imaging and machining spot sizes reduced sidewall signals (discussed later) and simplified the images. The imaging and machining light are were delivered coaxially through a 500 μm diameter gas nozzle orifice (nozzle to sample surface separation 1 mm) that delivered $N_2$ gas (in other cases, other gases and blends were delivered as well) at 2 bar to provide cooling, protection of the optics and suppression of combustion.

Figure 9:
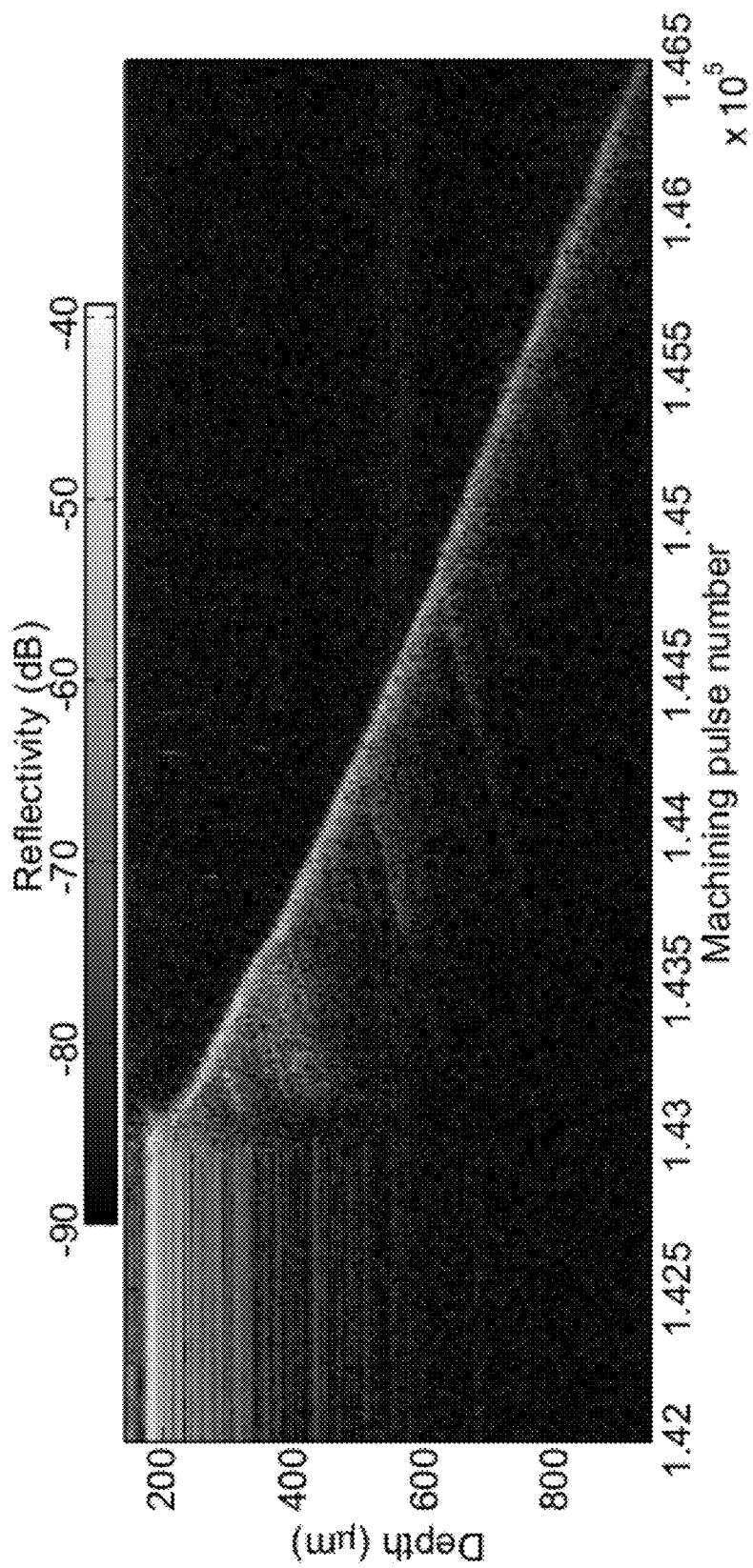
FIG. 9 shows an example of M-mode OCT imaging of laser cutting of bovine rib bone in which subsurface structure appears static during exposure to the initial $1.43 \times 10^5$ pulses, followed by a sudden onset of machining with an approximately linear etch rate.

Washed and desiccated transverse sections of bovine ribs served as convenient samples of thick, compact bone. The imaging system and machining pulse trains were asynchronously triggered as holes were percussion drilled into the samples in a direction transverse to the marrow axis. The M-mode images ("motion-mode"-reflectivity as a function of depth and time) showed that the cutting behavior was characterized by initial periods of little to no material modification followed by a rapid change in the sample and the sudden onset of cutting at ~10 mm/s. While this behaviour is common to this particular modification source, it has been seen to be substantially different using other sources. In FIG. 9, an example section of an M-scan shows this sudden onset after 143,000 machining pulses and the approximately linear progression of the hole thereafter.

The number of machining pulses required to initiate cutting varied from $10^2$ to $10^6$ on the same bone sample. This is attributed to the large degree of inhomogeneity in the tissue sample. While this behaviour is common to this particular modification source, it has been seen to be substantially different using other sources. Small variations in absorption and thermal resistance in the bone (from the presence of blood vessels, etc.) may create thermal "nucleation" sites where initially slow changes in residual moisture or carbonization lead to runaway increases in optical absorption and cutting. The variability in onset would likely be reduced for an ablation light source producing a centre wavelength with a short absorption depth in the tissue. In any case, in situ monitoring of the area of the sample exposed to machining light provided a direct readout of the onset of ablation.

Once cutting is initiated, material removal was approximately linear with pulse number. Several subsurface interfaces appeared to rise and meet the primary machining front. OCT measures optical path length and is thus affected by the index of refraction of the medium. Material removal above an interface reduces the optical path length to the stationary subsurface features. The ratio of the slopes (Equation below, 1-apparent depth of subsurface feature, x-hole depth) gave a direct measure of the effective index of the material being removed (n). Here n was found to be 1.5 in close agreement with past reports of 1.530 for similar tissue. These features can provide useful information for guided cutting as discussed below.

$$\frac{dl}{dt} = (1-n)\frac{dx}{dt}$$

Due to the stochastic nature of the onset of ablation, measuring per pulse or per fluence cut rates using conventional ex situ methods would be very difficult. Nevertheless, these parameters are important information for engineering surgical equipment and procedures. With inline coherent imaging, these measurements are straightforward and the information is available immediately after (and, in fact, during) the process, requiring no further modification of the samples. As a demonstration, 23 holes were drilled into ribs at four different repetition rates keeping average power constant (23 W). FIG. 10 shows the material etch rate and removal efficiency in bovine rib bone due to exposure from ns-duration fibre laser (constant average power 23 W). Error bars indicate the standard deviation of the results. Simple inspection of the M-mode data yields the resulting cut rates (FIG. 10 with error bars indicating 95% standard deviation confidence intervals). Though ablation is achieved through thermal processes, material removal is not simply dependent on average power. For example, in FIG. 10 (left), etch rate increases by only ~50% when pulse energy is almost tripled. Another way of showing this result is to consider the efficiency of material removal per unit incident light. Often it is desirable to reduce the light exposure without sacrificing cutting speed. Increased material removal efficiency is observed by increasing the repetition rate of the ablation laser source. Explained in simple terms, pulses with half the energy but twice the repetition rate are more effective at ablation than pulses with twice the energy but half the repetition rate. This suggests that intrapulse effects such as shielding from plasma generation/ejecta is reducing material removal and greater efficiency could be obtained from further increasing the repetition rate.

To demonstrate the versatility of the technique in guiding cutting, a portable ICI system based on a fiber-coupled superluminescent diode pair (1320±35 nm) and reflective grating spectrometer with InGaAs photodiode array was used. Use of this spectral band permits deeper imaging in bone, at the expense of speed and detector cost. Once integrated into the micromachining platform, the system has a 14 μm axial resolution, 30 μm transverse spotsize ($1/e^2$) in air. The large imaging beam width is used to collect morphology information from both the bottom of the incision as well as the surrounding tissue as discussed below. This system had a 98 dB sensitivity measured at 300 μm with 10 μs integration time and 7 mW incident on sample. The axial line rate is detector limited at 47 kHz. In this implementation, images were processed in LabVIEW on 4 cores of a PC using background spectrum subtraction, linear interpolation, FFT and noise floor equalization.

The machining source used here is a 100 W (maximum average power) fiber laser (IPG YLR-100-SM) at 1070 nm focused to 23 μm ($1/e^2$) that is pulsed via TTL command to emit 300 ns FWHM (measured) duration, 230 μJ pulses incident on the sample at a repetition rate of 47 kHz. Though the pulse FWHM is measured to be 300 ns, the shape is highly asymmetric with a total duration of approximately 3 μs. Longer duration pulses that correspond to a simpler pulse shape were also explored but resulted in degraded cut quality and reduced reproducibility.

Both imaging and cutting beams were coaxially aligned via a dichroic mirror and focused together via a single 50 mm achromatic lens. Imaging was electronically controlled to trigger asynchronously with laser exposure to provide the maximum delay between laser exposure and imaging. Though the tissue had not relaxed to equilibrium between pulses, the delay improves imaging contrast by minimizing fringe washout from fast changing interfaces.

The tested sample was cortical bone extracted from the spinous processes of the bovine lumbar vertebrae. To create thin sections of bone suitable for this proof of concept, a 1 mm diameter water cooled drill bit was used to hollow out small sections of the sample leaving approximately 600 um of bone sitting above a ~1 mm air gap. The bone/air interface provided an ideal target interface for machining.

Figures 11A, 11B:
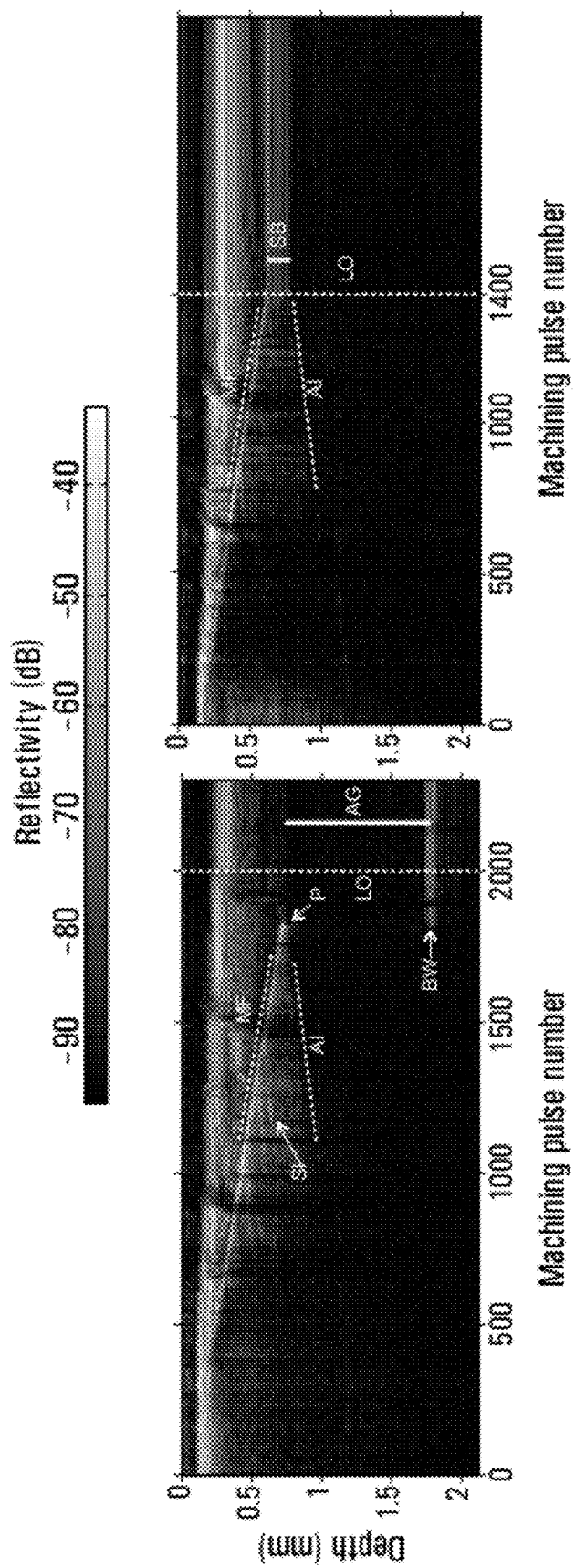
FIG. 11 is an example of M-mode OCT imaging of laser cutting of a multilayer sample.

M-mode imaging of the bone during laser exposure shows the progress of the machining front as a function of machining pulse. FIG. 11 shows machining where the laser exposure is controlled to achieve perforation into the air gap (left) and to stop the incision before perforation (right). The left part of FIG. 11 shows two groups of 1000 pulses causes perforation into air layer, showing next bone layer (depth 1.7 mm). The right part of FIG. 11 shows the application of 7 groups of 200 pulses results in cutting stopped 150 micron before penetration. Imaging (47 kHz) continued after cutting to show material relaxation after drilling. Annotations (intended as guides to the eye): MF—Machining Front; SI—Subsurface interface; AI—Air interface; BW—Back wall; P—Point of perforation; LO—Machining laser off; AG—Air gap; SB—Spared bone. The onset of material removal proved to be highly variable, e.g., taking 400 pulses in FIG. 11 left, and only 50 in FIG. 11 right, likely due to the nonuniformity of the top bone layer, as well as the nondeterministic nature of the onset of damage in CW machining. Once machining was initiated, it progressed with a well defined rate until perforation (FIG. 11 left), and the secondary bone layer became visible. Some obstruction of the imaging beam causes shadowing of subsurface structure, but tissue striations are clearly visible, with the most pronounced discontinuity due to the bone/air interface. As described earlier, the striations below the machining front appear to move upwards during material removal.

Scattering from above the machining front is observed in all images. This comes from scattering from the sidewalls of the hole. An imaging beam width larger than the machining beam was used to allow monitoring of sidewall modifications, thus achieving some degree of transverse information without lateral scanning. Lateral scanning is also done in situ (see below) but at the expense of reduced imaging rate. After laser exposure is terminated (pulse 2000 in FIG. 11 left, pulse 1400 in FIG. 11 right), the sample relaxes and sidewall and subsurface features become static. Variation in scattered light during machining arises due to changes in surface morphology as well as fringe washout for fast moving interfaces. Note that in SDOCT interfaces that move more than half the wavelength of light during the camera integration time will suffer reduced contrast. This motion-induced artifact is preferable over time-domain or swept-source variations of OCT where other fast moving interfaces will appear at incorrect depths, thus making tracking the incision more difficult.

Figure 12:
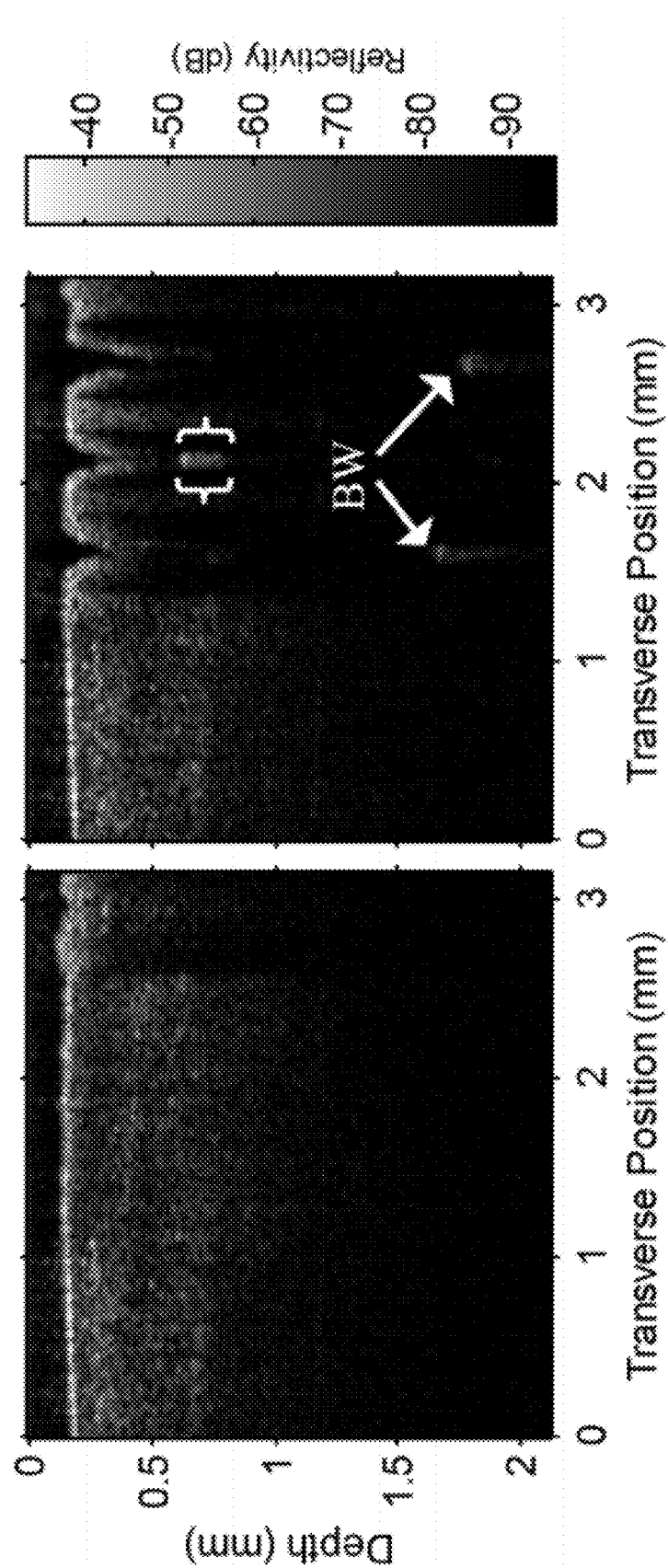
FIG. 12 is an example of in situ B-mode OCT image of bone before (left) and after (right) drilling.

By translating the sample, B-mode images of the drilling site before and after processing were obtained. Since in situ imaging is automatically aligned with the hole axis, deep imaging in high aspect ratio (>20) holes was straightforward. FIG. 12 shows in situ B-mode OCT image of bore before (left) and after (right) drilling. The two clear holes show the lower bone interface, while the middle hole (corresponding to FIG. 12 right) was drilled to stop 150 μm before the air gap. The spared bone thickness is highlighted with brace brackets. Back walls seen through holes corresponding to those in FIG. 12 (left) are labelled BW. The middle hole clearly shows the spared bone (brace brackets in FIG. 12 right) above the air gap. The other two holes are through holes, showing the air gap and scattering from the lower bone layer. Increased scattering from the sidewalls of the holes caused by tissue modification in the thermal cutting process does reduce the penetration depth of the imaging light, sometimes obscuring deeper features. This can be minimized by selecting a laser modification process that causes little or no carbonization of the modification site.

Applying these forward looking coherent imaging capabilities may, in some instances, result in tracking of machining in hard tissue over millimeter length scales with several orders of magnitude greater temporal resolution than has previously been reported. It is demonstrated that real-time imaging permits accurate cutting in tissues in which little a priori information is available and which may have a highly stochastic response to machining energy. This development is an important step towards fine control in hard tissue surgical procedures, particularly in the vicinity of sensitive organs such as the nervous system.

Spectral Domain Optical Coherence Tomography

Embodiments described herein use spectral domain optical coherence tomography and variants. Spectral domain optical coherence tomography (SDOCT) has been described as the optical analogue of ultrasound imaging. The measurement uses a white light, optical fiber interferometer to obtain the optical path length (OPL) of an object relative to a fixed reference length. In the spectral domain, the relative OPL of the sample reflection is encoded in the spacing of the spectral interference fringes in the output from the interferometer. Specifically, consider a set of p reflectors in the sample arm, each with an OPL difference from the reference length of $z_i$. The resulting spectral interferogram intensity is approximately:

$$I(k) = A(k) \sum_{i=1}^{p} \left[ \frac{I_{ref}}{2p} + \frac{I_i}{2} + \sqrt{I_{ref} I_i} \cos(2kz_i) \right]$$

$A(k)$ is the spectral envelope of the imaging light source and k is wavenumber. The first term is known a priori and can be subtracted as a background signal. The second term is typically very small and can be neglected. In the third term, the weak sample reflection ($I_i$) has its intensity multiplied by the strong reference signal and appears as a sinusoidal interference fringe whose spacing (i.e., frequency) depends on its depth ($z_i$). Since each depth corresponds to a different fringe frequency, the signals are orthogonal and can be monitored independently with no moving parts. Acquisition speed and signal-to-noise are therefore limited by the detector and the intensity of the imaging light. It should be emphasized that ICI can work coaxially with the machining beam, enabling depth sensing with hole aspect ratios much higher than would be possible with triangulation methods.

To extract depth information, the spectral interferogram (measured with a spectrometer) may be resampled to units of constant wavenumber by interpolation and may be transformed to I(z) via FFT. The resulting function (known as an A-scan or A-line) is a depth-reflectivity profile of the sample (shown in logarithmic units relative to the noise floor) with each reflecting interface in the sample appearing as a point spread function (PSF) centered about its depth. The PSF full width at half maximum (FWHM) is usually referred to as the axial resolution of the system, and for Gaussian A(k) as:

$$\delta z = \frac{2\ln 2}{\pi} \frac{\lambda^2}{\Delta\lambda}$$

Thus a short center wavelength (λ) of the light source and broad spectrum (Δλ) are desired for high resolution imaging. Typical axial resolutions in biological imaging on the order 5-10 μm are achieved with quasi Gaussian spectra of 830±30 nm FWHM (ophthalmology) or 1310±35 nm FWHM (scattering tissue).

One important imaging artifact may arise due to the ambiguity between positive and negative OPL ($z_i$ and $-z_i$ yield the same interferogram). Since the spectral interferogram is purely real, the depth-reflected profile has complex conjugate symmetry about zero. Half of the image is usually discarded leaving only positive OPLs. However, if a reflecting interface is located on the negative side of the reference point, its signature wraps back into the image as an artifact. Thus, some embodiments are designed with an adequate depth field of view (FOV) and care is taken to ensure that all reflecting interfaces are located on only one side of the zero optical path length difference point.

Figure 13:
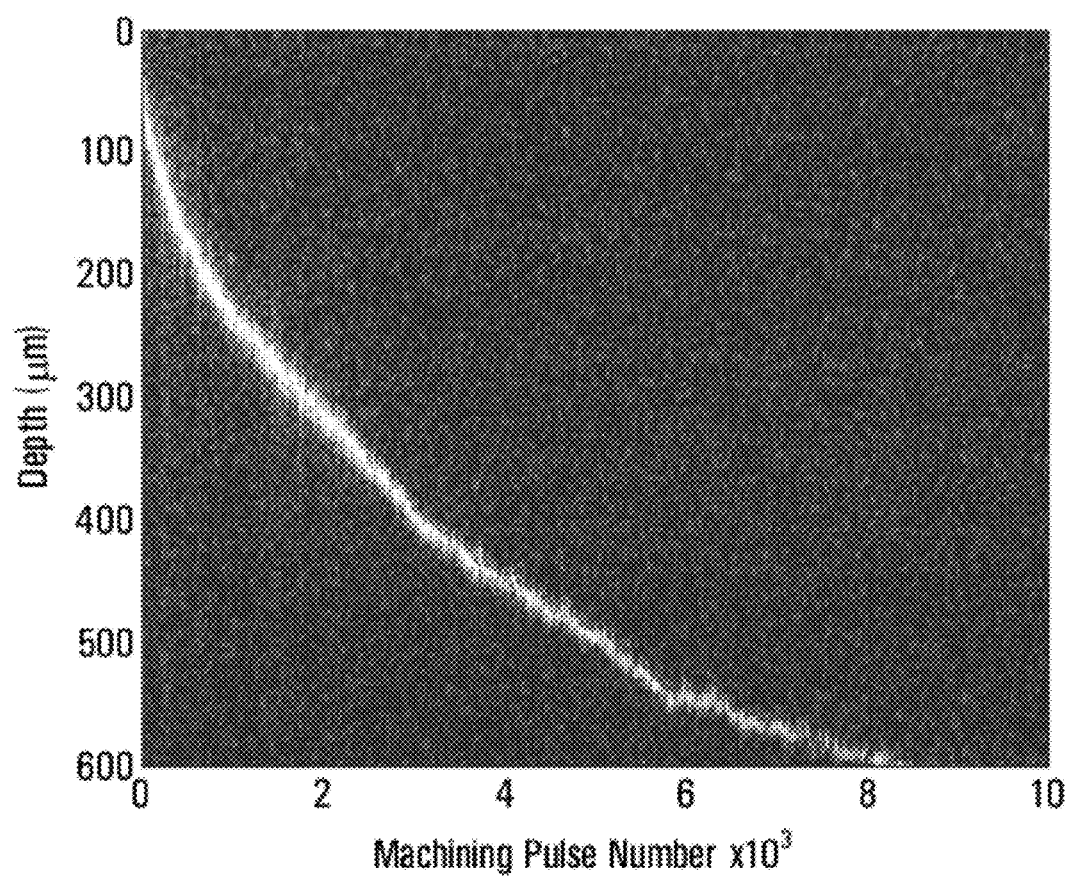
FIG. 13 is an example of a real-time M-mode image of percussion drilling in steel.

To create an image, many spectral interferograms may be acquired serially by the spectrometer, processed into A-lines ("axial-line"-reflectivity as a function of depth) and then displayed as a 3D dataset of reflectivity vs. depth vs. A-line number. In biological imaging, the A-line number corresponds to transverse position as the imaging beam is raster scanned. This produces an image of reflectivity as a function of two spatial dimensions known as a B-mode image (B=brightness). Alternatively, if the beam is static, the A-line number corresponds to time and the resulting image is called an M-mode image (M=motion). This type of image is useful for observing fast changes in the depth-reflectivity profile of the sample. For example, coaxial imaging during the percussion drilling of 304 stainless steel with a 1070 nm center wavelength, 100 ns duration fiber laser (IPG YLP-1/100/30/30-HC) gives the M-mode image in FIG. 13. The machining front (bright white curve) is seen descending ~600 μm into the bulk of the sample. The complete etch depth vs. pulse number relationship was obtained from drilling a single hole and required no post-cut material processing.

760 μJ pulses were incident onto a 20 μm $e^{-2}$ intensity diameter spot at 30 kHz. A coaxial oxygen assist gas jet at 8.3 bar was used. Imaging rate is 300 kHz. Graph brightness corresponds to sample reflectivity in logarithmic scale. The dynamic range shown is ~60 dB.

With acquisition rates of even a few tens of kilohertz, M-mode images are not only able to directly measure etch rates but also melt pool flow and other dynamics of laser drilling/welding processes. Since sensing below the machining front is possible, M-mode data may also be used in conjunction with appropriate feedback hardware to guide blind hole cutting in a variety of semitransparent materials including biological tissue even when the exact sample geometry is not known a priori.

Figure 14:
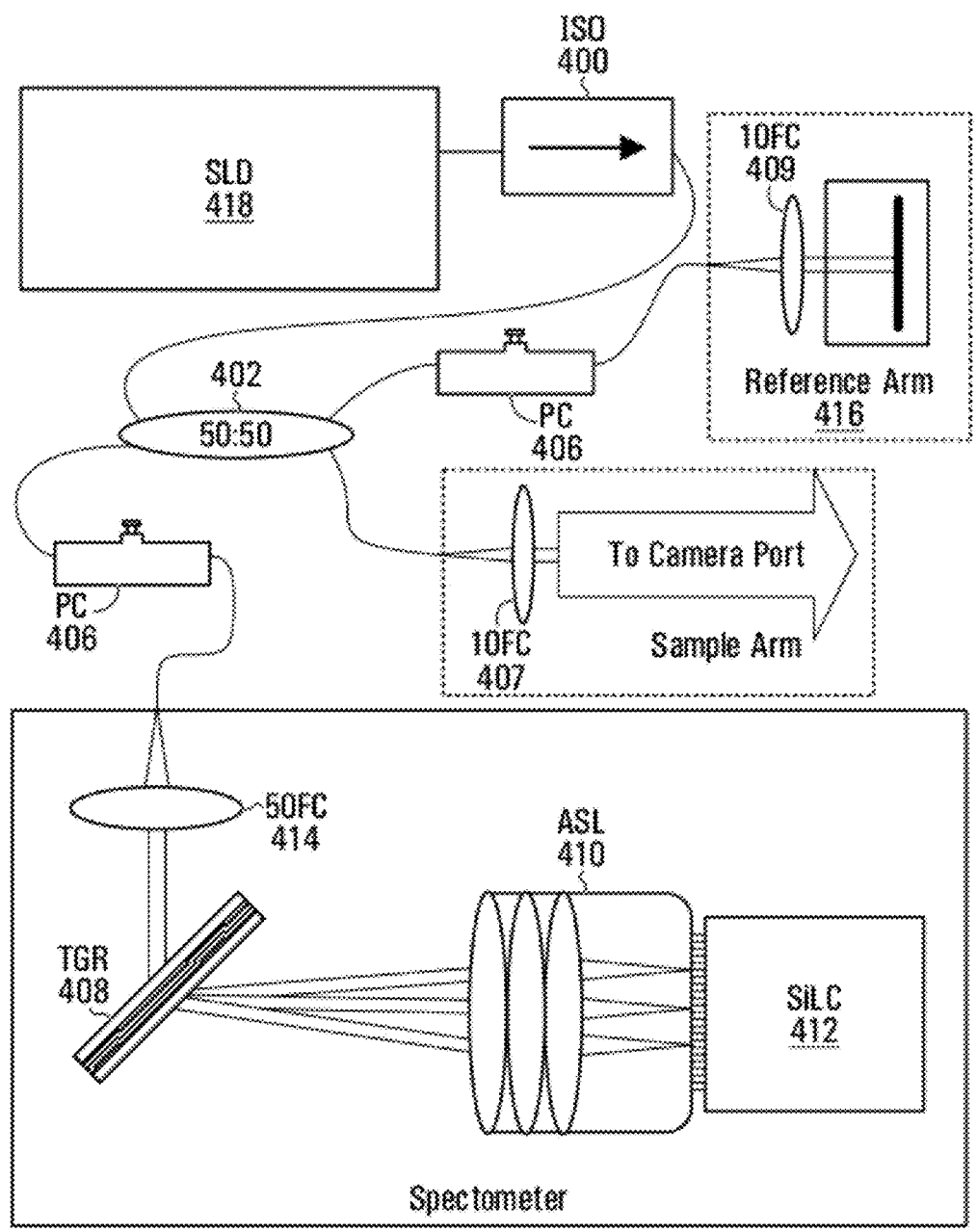
FIG. 14 is a block diagram of another example imaging system provided by an embodiment of the invention.

FIG. 14 is a schematic diagram of another imaging system provided by an embodiment of the invention that will be used as an example for homodyne mixing. However, homodyne mixing can be used with any of the systems described herein. Labels: ISO—Fiber Coupled Optical Isolator 400; 50:50—Mode coupler 402; PC—polarization controller 406; TGR—transmission grating 408; ASL—Air spaced lens 410; SiLC—Silicon CMOS line camera 412; 50FC—50 mm fiber collimator 414; 10FC—10 mm fiber collimator 407, 409. There is a fiber-coupled superluminescent diode (SLD) 418, a custom spectrometer, and fiber optic Michelson interferometer that can be interfaced to a laser machining head through a camera port (more generally an optical access port). Imaging light from the SLD first passes through an optical isolator and/or circulator, which protects the SLD from back-reflection. The light continues into an evanescent mode coupler (beam splitter or beam combiner) where it is split into the sample and reference arms, then coupled out of the fiber and into free space. Some light is retroreflected in both interferometer arms and the signals are recombined and interfere at the mode coupler. Polarization controllers correct for mismatches between the two interferometer arms arising from polarization effects in single mode fiber and also to optimize diffraction grating efficiency. Polarization maintaining fiber may also be used together with or instead of polarization controllers. A transmission grating is used in the spectrometer for ease of alignment. Finally, the camera measures the spectral interferogram and transmits data via IEEE-1394 to a desktop computer (or other processing platform, not shown) for processing.

The following is an example measurement of the performance of the system of FIG. 14.

TABLE 1

Calculated System Performance Characteristics

| | |
|---|---|
| Axial Resolution (μm) | 12 |
| Depth of Field (mm) | 5.9 |
| Maximum Line Rate (kHz) | 27 |
| Duty Cycle (IEEE-1394 interface limited) | 0.73 |
| Sensitivity (dB)*† (35 μs integration) | 98 |
| Sensitivity (dB)*† (1 μs integration) | 82 |
| Sensitivity (dB)*† (100 ns integration) | 67 |
| Max. Dynamic Range (dB)* | 66 |

*Based on noise specifications available for camera operating at low speed. Actual value is expected to be lower at full speed.
†Assumes sample arm optics have ~80% efficiency Some embodiments may have different speed, sensitivity, resolution and/or dynamic range depending on the choice of components.

In some embodiments, a complete system would also include custom interfacing with machining heads for specific applications. This can generally be accomplished by modifying a camera port and choosing the correct dichroic optic to combine the imaging and machining light. Additionally, an appropriate focused beam diameter for the imaging beam may be chosen. In some implementations, the imaging and machining light will be focused by the same objective (though this is not necessary) whose focal length is predetermined by existing machining process demands. Here, the choice and alignment of the sample arm collimator can be used to give the desired focal characteristics for imaging. Collimator alignment can also be used to compensate for focal length variation of the objective between imaging and machining light.

As an example application, a machining laser head with a 100 mm focusing lens is considered. To maintain uniform imaging over the depth of field, the collimator's focal length should be chosen so that the focused imaging beam's Rayleigh range is approximately half the system's depth of field. For the setup described above, we choose a 10 mm collimating lens and hence, expect a beam waist of 27 μm ($1/e^2$ intensity radius) and a Rayleigh range of 2.8 mm. Note that to achieve maximum axial resolution, proper compensation of dispersion mismatch between the sample and reference arms may be of use.

The design is flexible and can be modified to improve imaging rate (with an upgraded camera) or axial resolution. The latter is achieved by selecting a broader spectrum SLD (or other light source) and a grating with a reduced line density. This would provide significant resolution improvement with the drawback of reduced depth of field but little to no additional monetary cost. For instance, substituting the current components with an 840±25 nm FWHM light source (Exalos EXS8410-F413) paired with a 1200 lines/mm grating (Edmund Optics NT48-589) could provide 6.2 μm resolution over a maximum range of 3 mm. Note that with higher spectral bandwidths, proper dispersion mismatch compensation is important to achieve maximum resolution.

Note that in coherent imaging techniques such as this, if an interface moves by ~λ/4 or greater during the integration time of the detector, the fringe contrast will be significantly degraded ("washed out"), causing the signal from that interface to vanish. This corresponds to an upper limit to the interface speed that can be tracked. However, it also has the benefit of rejecting certain high-speed interfaces (e.g. ejecta) that would produce reflections that complicate the images and make automatic feedback more difficult. The maximum interface speed depends on the integration time of the detector, which in turn affects sensitivity. For an integration time of 35 μs, the system can track interfaces moving at speeds up to 0.006 m/s. For faster moving interfaces, integration time can be reduced (at the expense of sensitivity) to 1 μs or 100 ns to give maximum speeds of 0.21 m/s or 2.1 m/s, respectively. Since this is faster than typical etch rates in industrial processes, it is expected that this design will be adequate for a wide range of applications. The use of line cameras with shorter integration times, balanced photodetectors and/or swept sources may allow even faster moving interfaces to be resolved.

Homodyne Depth Filtering

To use ICI as an automatic feedback method, processing is preferably able to run at least as fast as data acquisition. In biological imaging, the interpolation and FFT operations are necessary to calculate the reflected intensity from all the depths within the FOV to form an image. By contrast, in feedback systems, the imaging output is used to trigger a change in the material modification process as a function of the imaging output (e.g. terminate emission), for example once a certain depth has been reached. In this case, calculating the reflectivity from all the depths may be excessive. An efficient method for determining when drilling has penetrated a prescribed depth is provided.

Starting with a desired depth, z, and using Equation for I(k) presented above with calibration data from the spectrometer, a synthetic interferogram is pre-calculated, expressed in units of constant camera pixel number (or the basis that corresponds to the detection system). This calculation can be completed a priori and does not contribute to the real-time computing load. Multiple such pre-calculated synthetic interferograms may be generated and drawn (individually or otherwise) from a memory table to be used for different target results, for example, achieving one of several possible depths, tracking the approach to a desired depth through a series of intermediate steps, removal of material from a specified depth, achieving more material at one depth compared to another depth, or optimizing change in backscatter from a target depth.

Figure 20:
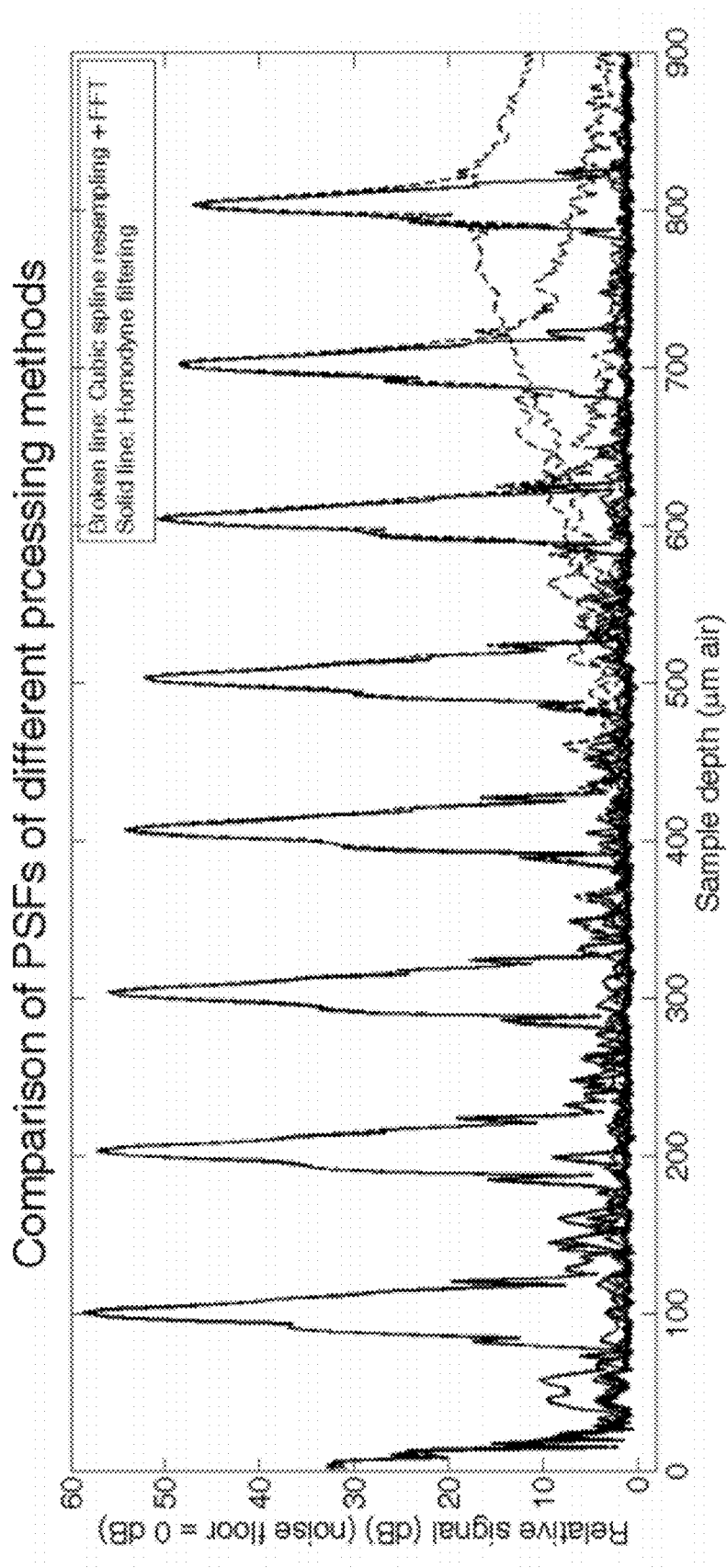
FIG. 20 is a plot comparing Homodyne filtering to standard (cubic spline resampling, FFT) processing.

By homodyne mixing the synthetic interferogram with the raw data from the camera, the signal from the desired depth is extracted which may have significantly lower spurious sidelobe signal (from interpolation errors) when compared to other methods known to those skilled in the art as shown in FIG. 20. F. For each imaging output from the camera, the raw data from the camera is multiplied by the synthetic interferogram pixel by pixel and then summed. When the desired depth is reached, the summed result will have a peak.

Where it is desirable to combine the signal with multiple synthetic interferograms, a matrix multiplication approach may be taken.

If data elements are transferred from the detector serially or quasi-serially (i.e. through multiple camera taps) then the receiving electronics in some embodiments may begin calculations on the individual elements as soon as they become available in order to preserve processing resources such as memory and/or gates (such as on a field programmable gate array, FPGA) and to reduce the overall feedback latency.

Figure 15:
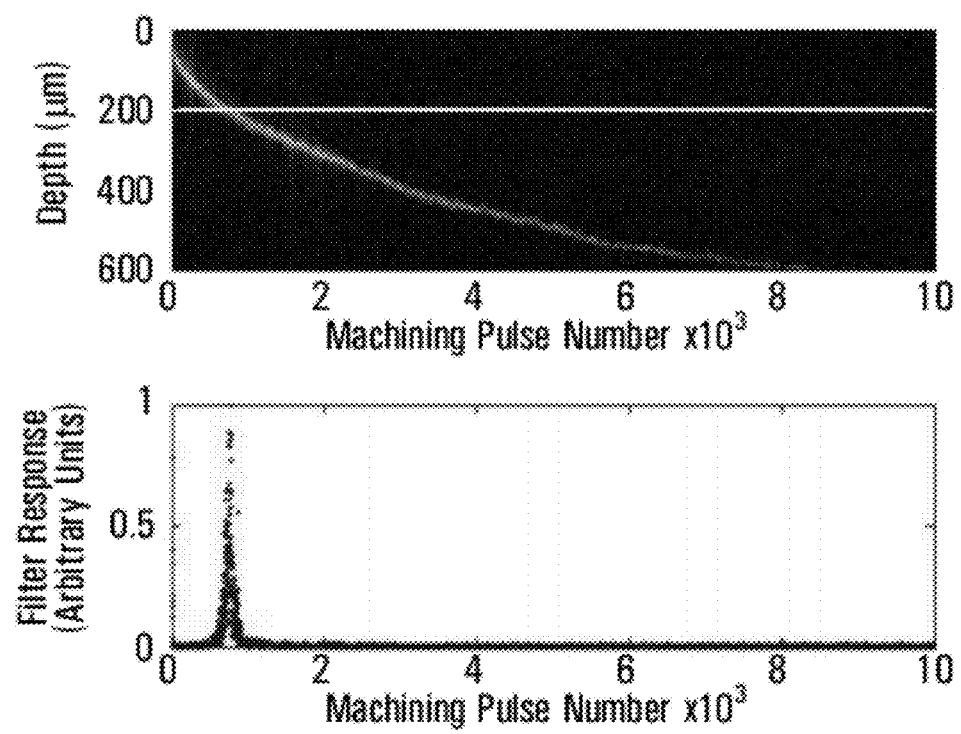
FIG. 15 is a depiction of a fully processed M-mode image from the system of FIG. 14 with a line superimposed at the selected filter depth (top), and showing the response from the homodyne filter exhibiting a sharp peak as the machining front crosses the selected depth (bottom)

To demonstrate, this filter technique is applied to the spectrometer data used in FIG. 15, choosing a 200 μm target depth (indicated by a line 100 in FIG. 15). The filter response shows a clear, high SNR response at the moment the machining front passes through the depth (Figure B bottom).

Figure 16:
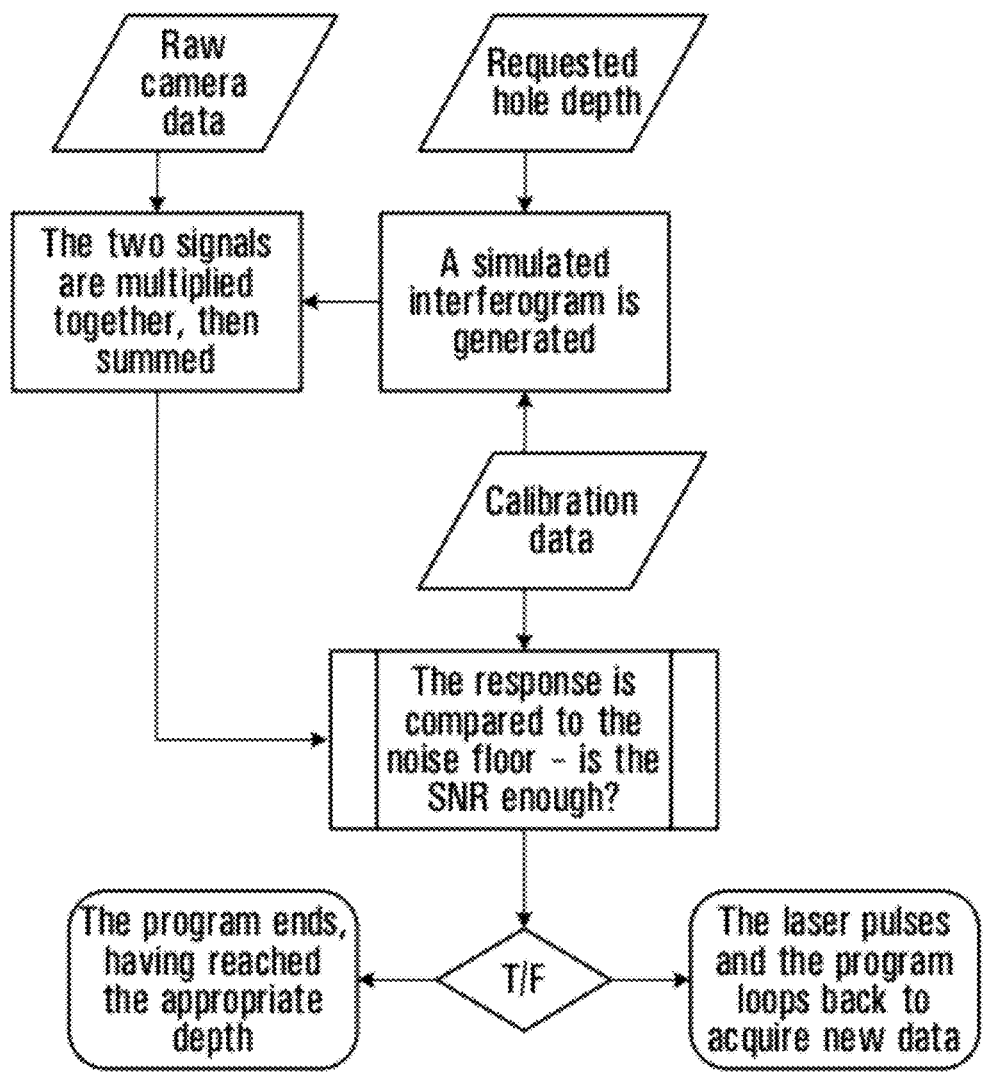
FIG. 16 is a flowchart of a method of feedback control using the homodyne filter-based approach.

The filter response is used to trigger a feedback response to stop drilling, or to make some other change to a parameter of a material modification process. FIG. 16 is a flowchart of a method of automatic feedback control, which can, for example be used to stop drilling, based upon when a prescribed depth is reached. More complicated control systems with feedback from multiple depths and control of other parameters of the process are also possible. In some embodiments, a look-up-table is employed to rapidly and dynamically change the depth(s) of interest (by selecting different pre-calculated synthetic interferograms).

Depth filtering may achieve computational savings versus standard processing. The time required to process multiple blocks of 576 element lines of previously acquired, raw experimental data with both our standard biological imaging code (background subtraction, cubic spline interpolation, FFT, noise floor equalization) and with the homodyne filter is compared in Table 2. Processing was conducted with a single thread running MATLAB on a quad-core Intel desktop CPU in a Microsoft Windows 7 64-bit environment. The results in Table 2 are expressed in terms of $10^3$ lines per second (klps) and the relative speed increase factor obtained by using the homodyne filter.

TABLE 2

Comparison of processing speed for $4 \times 10^5$ image lines

| Block size (A-lines) | Interpolation + FFT (IF) speed (klps) | Homodyne filter (HF) speed (klps) | Relative speed (HF/IF) |
|---|---|---|---|
| $2 \times 10^5$ | 0.77 | 451.2 | 588 |
| $2 \times 10^4$ | 5.096 | 522.2 | 102 |
| $2 \times 10^3$ | 4.596 | 555.6 | 121 |
| 200 | 1.861 | 794.0 | 427 |
| 20 | 0.241 | 746.0 | 3097 |

For very small and very large block sizes, the FFT method is very slow. This is a result of limitations specific to the hardware and software environment and not the computational complexity of the code. As a result, the best theoretical comparison between the two methods is the mid-size blocks. Here, even when the FFT produces its best results, the homodyne filter still outperforms it by two orders of magnitude.

While the line period limits the raw throughput rate, it is only a minimum value for the total feedback latency. Interrupt latency and other delays inherent to desktop hardware and operating systems are additive and may ultimately be the dominant terms. For this reason, the full capabilities of ICI-based feedback potentially will not be realized without the use of dedicated processing hardware in the form of a field programmable gate arrays (FPGAs) or application-specific integrated circuits (ASICs). These components already exist in many modern cameras, including the one specified here. The ease of implementation of the homodyne filter algorithm described here onboard a camera circumvents the desktop PC bottleneck and allows the camera itself to discipline the machining system.

Imaging Below Surface

Figure 17:
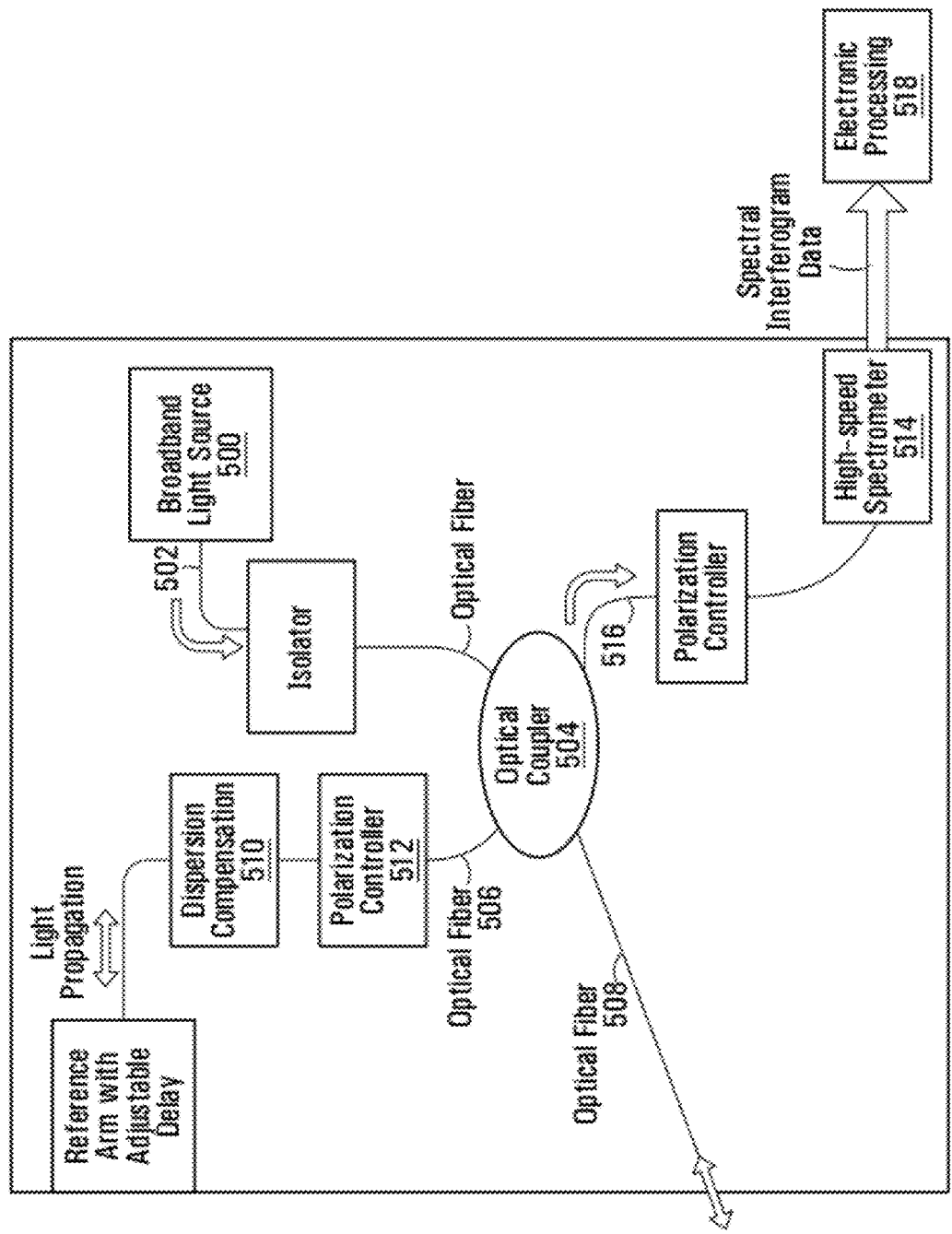
FIG. 17 is a block diagram of another inline coherent imaging system.

FIG. 17 is another example of a system featuring inline coherent imaging. This implementation features an optical fiber implementation of ICI. A broadband light source 500 injects light into the optical fiber 502. An isolator blocks back reflections from reaching the light source. Optical coupler 504 splits the light into reference arm (top) 506 and sample arm 508 (bottom, to laser processing system). The ratio of splitting depends on the applications needs. An example would be 50:50 (50% to the reference arm, 50% to the sample). The reference light travels along the reference arm and is back reflected. The path length of the reference arm can be set in coarse divisions, using various lengths of optical fiber, and fine divisions using a mirror mounted on a translation stage with micrometer control. Usually the reference arm length is set to match the optical path length to the workpiece in the laser processing system, less approximately two hundred micrometers. Often it is convenient to put a focussing objective identical to the one used in the laser processing platform before the reference mirror (not shown) in order to match dispersion and control reflected reference arm power. The reference arm contains optics 510,512 that allow dispersion and polarization control. Dispersion control is done so both reference and sample arm are close to dispersion matched. Polarization control is usually set so the reference and back reflection from the sample arm have similar polarization states (for maximum interference). The reference arm also may include a controllable intensity attenuator (not shown) to control detector saturation and imaging dynamic range. This can be accomplished by a variable neutral density filter, misalignment of a fiber coupler, or translation of the focussing objective relative to the end reference mirror (all not shown). The sample arm fiber exits the inline coherent imaging system and is connected to an external laser processing platform. Light backscatters off the workpiece and travels back along the same fiber. The back-reflected reference light splits at the optical coupler 504 so part of it is injected into the fiber connected to the high-speed spectrometer 514 (amount depending on the coupler splitting ratio). The backscattered sample light splits at the optical coupler so part of it is injected into the fiber connected to the high-speed spectrometer (amount depending on the coupler splitting ratio). The sample and reference light interfere in the optical fiber 516. The light is dispersed according to its wavelength in the spectrometer. The detector may be a spectrometer that measures intensity as function of wavelength. The position of the constructive and destructive peaks contains information about the relative path length of the sample arm compared to the reference arm. If light is backscattered simultaneously from more than one depth in the sample arm (e.g., sides of a laser keyhole), the strength and relative positions of all the depths is encoded in the interferogram. The spectral interferogram (intensity as a function of wavelength) is converted into an electronic signal by the detector and transmitted to control electronics 518 for processing. The electronic processing system controls the spectrometer (e.g., triggering) and processes the raw detector data. One processing technique (so-called standard OCT processing) is back subtraction, cubic spline interpolation for conversion from camera pixel number to constant frequency step, fast Fourier transform to yield a graph of backscatter as a function of depth. If there is only one highly reflecting interface in the sample arm, the resulting graph will have one strong peak with its width set by the axial resolution of the system. Axial resolution is inversely proportional to wavelength bandwidth measured by the spectrometer (thus the need for a broadband source to achieve high resolution). Alternatively, the homodyne filtering approach described above may be used for faster processing times and improved image quality. In some embodiments, a feedback controller (part of or separate from electronic processing 518) generates feedback to control one or more processing parameters of the material modification process. Examples have been provided above in the context of other embodiments.

Figure 18:
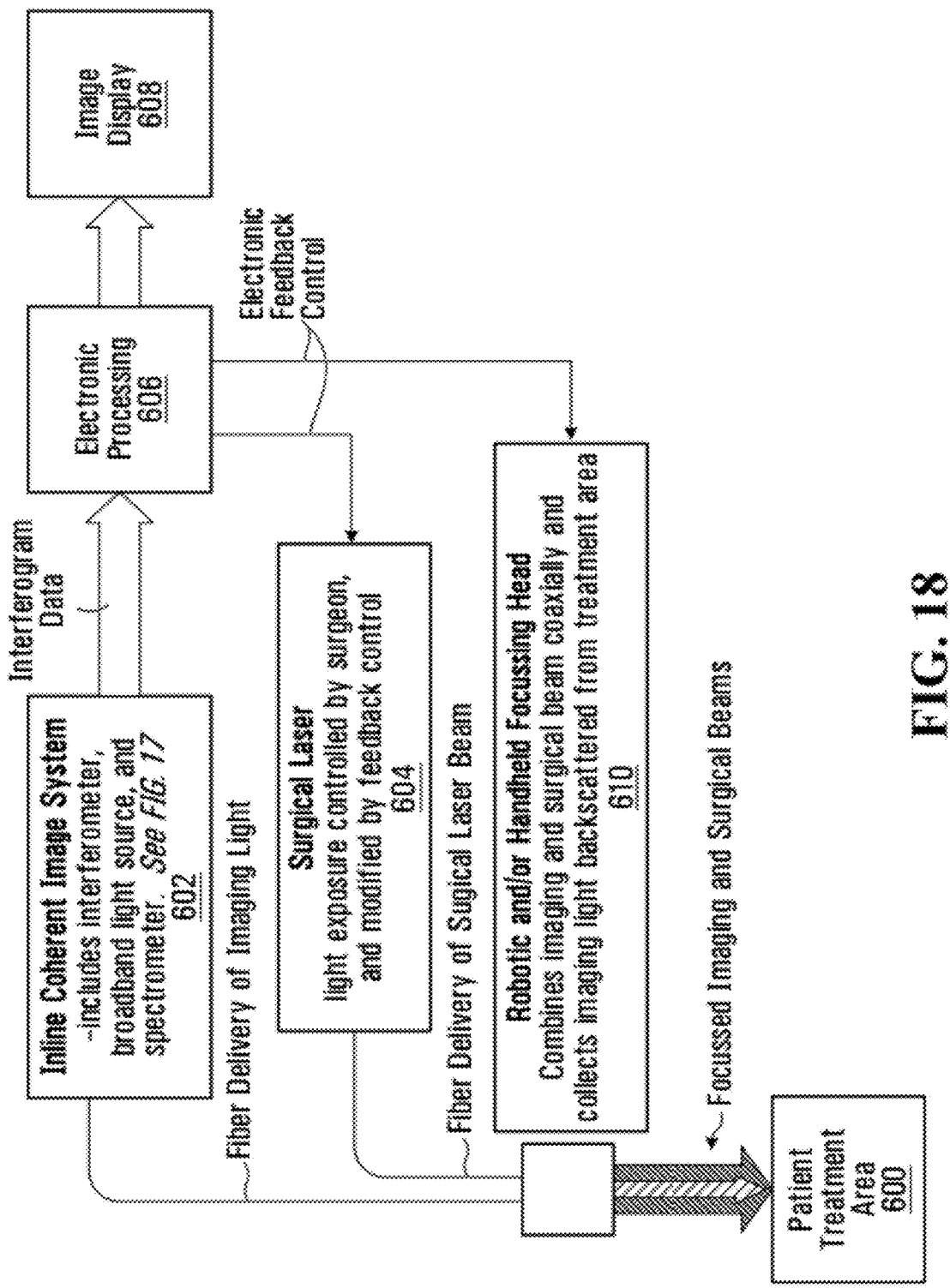
FIG. 18 is a block diagram of a laser surgery system featuring the ICI system of FIG. 17.

FIG. 18 is a block diagram of an application of the ICI to forward-viewing guided laser surgery. Lasers are useful for tissue ablation because the light can be focused very tightly, allowing the surgeon to remove tissue in small volumes. While the light can be delivered with high precision in the transverse dimensions, it is difficult to control the final depth of the laser incision. Tissue can be highly heterogeneous with a large variation in removal rate, making total energy delivered not a good predictor of incision depth. FIG. 18 shows a patient treatment area 600 that contains a volume of hard or soft tissue that would usually be removed by mechanical methods (e.g., drill). The ICI system measures incision depth as tissue is ablated, and terminates laser exposure at a predetermined depth. More importantly, when ICI is implemented using infrared light (~1300 nm), imaging into the tissue (beyond the ablation front) is possible. This allows exposure to be terminated before an interface is penetrated (and before the intense surgical laser can damage delicate subsurface tissue).

An inline coherent imaging system 602 is provided; this includes an interferometer, broadband light source and spectrometer, and an example implementation is depicted in FIG. 17. The patent treatment area is indicated at 600. There is a surgical laser 604 which generates exposure controlled by a surgeon, and modified by feedback control. There is a robotic controlled focussing head 610 (but may be handheld in some other embodiments) which combines imaging and surgical beam coaxially and collects imaging light backscattered from the treatment area. In some embodiments, imaging and surgical laser light may be combined earlier in the propagation path of the surgical laser such that imaging and surgical light arrive pre-combined at the focussing head. The spectral interferogram data from the ICI system 602 is passed to electronic processing 606 which generates the electronic feedback control for the surgical laser and robotic controlled focussing head. In addition, an output is generated for an image display 608.

The beam from the sample arm of the ICI interferometer is set to be coaxial with the surgical laser 604. This can be done in free space with an appropriate dichroic mirror. This guarantees imaging is along the same line as the surgical beam direction. The reference arm length is set so sample arm and reference arm are closely matched. The surgeon can use the image display to image the target area (and below) before he/she starts the surgical laser. The imaging system can also be used to fine tune the position of the surgical laser using co-registration with other imaging modalities (such as prerecorded MRI or CT). This would allow the surgeon to look at a small volume of the treatment area in real-time using the ICI in the context of larger anatomical features. The electronic processing would do this co-registration. In addition, the surgeon could have selected margins to be removed using the prerecorded imaging modalities.

Once the surgeon is certain that the surgical laser will target the right treatment area consistent with the treatment plan, he/she starts the ablation process. The system can be programmed to terminate exposure after a certain depth is cut, or to remain within a certain preset margin, or to terminate exposure when ablation reaches a certain distance to a selected interface. The ICI system can be used to provide a permanent record of the treatment procedure, useful for post-operative analysis.

Figure 19:
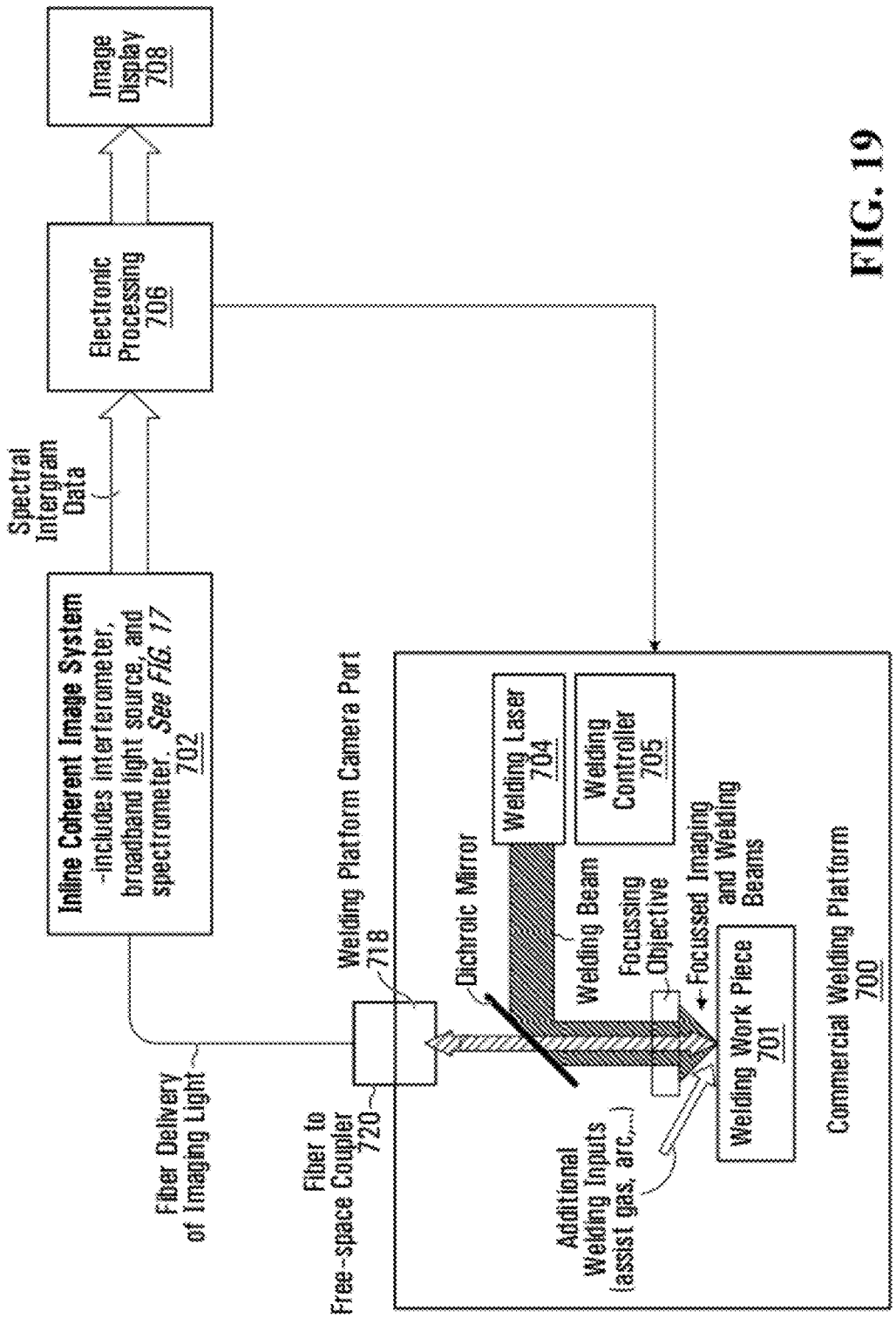
FIG. 19 is a block diagram of a welding system featuring the ICI system of FIG. 17.

FIG. 19 is a block diagram of an application of the ICI for in situ metrology for laser welding. Laser welding provides narrow and deep welds, well suited to automated and high volume manufacturing. The diverse applications for laser welding have in common a process of controlled heating by a laser to create a phase change localized to the bond region. Controlling this phase change region (PCR) can be used to control the quality of the weld and the overall productivity of the welding system. The high spatial coherence of laser light allows superb transverse control of the welding energy. Axial control (depth of the PCR) and subsequent thermal diffusion are more problematic particularly in thick materials. In these applications, the depth of the PCR is extended deep into the material (~mm) using a technique widely known as "keyhole welding". Here, the beam intensity is sufficient to melt the surface to open a small vapor channel (also known as a capillary or "the keyhole") which allows the optical beam to penetrate deep into the material. Depending on the specific application, the keyhole is narrow (<mm) but several millimeters deep and sustained with the application of as much as $\sim 10^4$ W of optical power.

In FIG. 19, an inline coherent imaging system 702 is provided; this includes an interferometer, broadband light source and spectrometer, and an example implementation is depicted in FIG. 17. The welding platform is indicated at 700. There is a welding laser 704 which generates a welding beam controlled by a welding controller 705, taking into account feedback control. A focussing objective 703 combines imaging and welding beam for delivery to a welding work piece 701 and collects imaging light backscattered from the welding area. There may be additional welding inputs such as assist gas, an electrical arc, additive material etc. The spectral interferogram data from the ICI system 702 is passed to electronic processing 706 which generates the electronic feedback control for the welding controller 704. In addition, an output is generated for an image display 708. In this case, the ICI system 702 is connected to a welding platform camera port 718 through a fiber to free-space coupler 720.

To measure keyhole formation in real time, the sample arm of the ICI imaging system 702 is set to be coaxial and/or near coaxial with the welding laser beam, to be focussed in the PCR. This can be done by collimating the image beam and directing it into the welding platform camera port. The ICI system is used to monitor the depth of the keyhole formed, ensuring that it is appropriate depth for welding all the workpieces. In pulsed laser welding, the ICI system can be run at a multiple of the repetition rate of the welding laser, providing images from before, during and after laser exposure. This provides direct information on the creation of the vapour channel, and its subsequent refilling. With continuous-wave welding sources, the ICI system can monitor keyhole stability directly. Feedback from this information can be used to optimise welding parameters (such as laser intensity, feed rate, and assist gas), to increase keyhole stability.

The image display 708 shows the operator real time information about keyhole penetration and stability as welding is in process, and provides a permanent record of the weld creation, situated to the exact region on the workpiece. This can be important for later quality assurance.

Another embodiment of the invention provides a fiber-based ICI in which a common dielectric objective is used to combine the imaging light and the laser light. Such an embodiment, optionally, includes a feedback controller, for example as defined in any of the other embodiments described previously.

Other embodiments combining, mixing or interchanging the fundamental design elements described herein can be possible and will be evident to persons skilled in the art. These include, but are not limited to, imaging from other directions (i.e. not in-line with the modification beam) including the underside of the material being modified.

Engineering the Sensitivity Vs. Depth to Manage Dynamic Range

ICI differs from other forms of coherent imaging (such as OCT) in the way information from the intensity of the reflected light is used. In OCT imaging applications, it may be desirable to have a very flat sensitivity vs. depth relationship in order to maintain even contrast and visibility over the entire image. In ICI, one is primarily interested in locating optically reflective (e.g. metallic) surface(s) and so even contrast over the entire image is not as important as in OCT.

In some embodiments, steps are taken to engineer the sensitivity vs. depth function of the imaging system to attenuate bright reflections relative to the weaker ones and extend the overall dynamic range. ICI may benefit from such an extended dynamic range due to the highly variable reflectivity of materials in different orientations. Reflections may be strongly generated from an interface, or they may be weakly generated. There may be multiple surface and internal reflections, at varying heights. It is possible to configure the operation of an ICI based system to be more sensitive in regions of interest where it is expected that reflections may be weaker.

For example, when using an ICI system such as the one shown in FIG. 5, the periphery of a machined feature may naturally reflect more light into the imaging system than the bottom of a hole. Therefore stronger signals may be anticipated from shallower depths. If the imaging system is configured for maximum sensitivity (in order to optimize its ability to detect the bottom of the hole), then there may be a risk of saturating the detector with the much stronger signals originating at the top of the hole.

Figure 21:
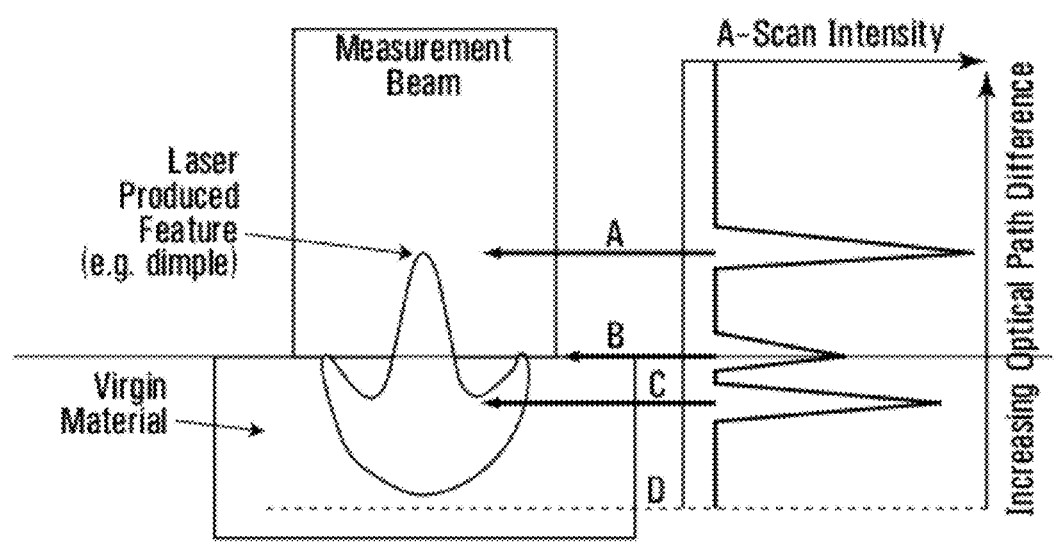
FIG. 21 shows an imaging beam and a laser produced feature, the imaging beam having a larger diameter than the laser produced feature, and in which the zero optical path length difference point is selected to be at a depth located inside the material being measured.
Figure 23:
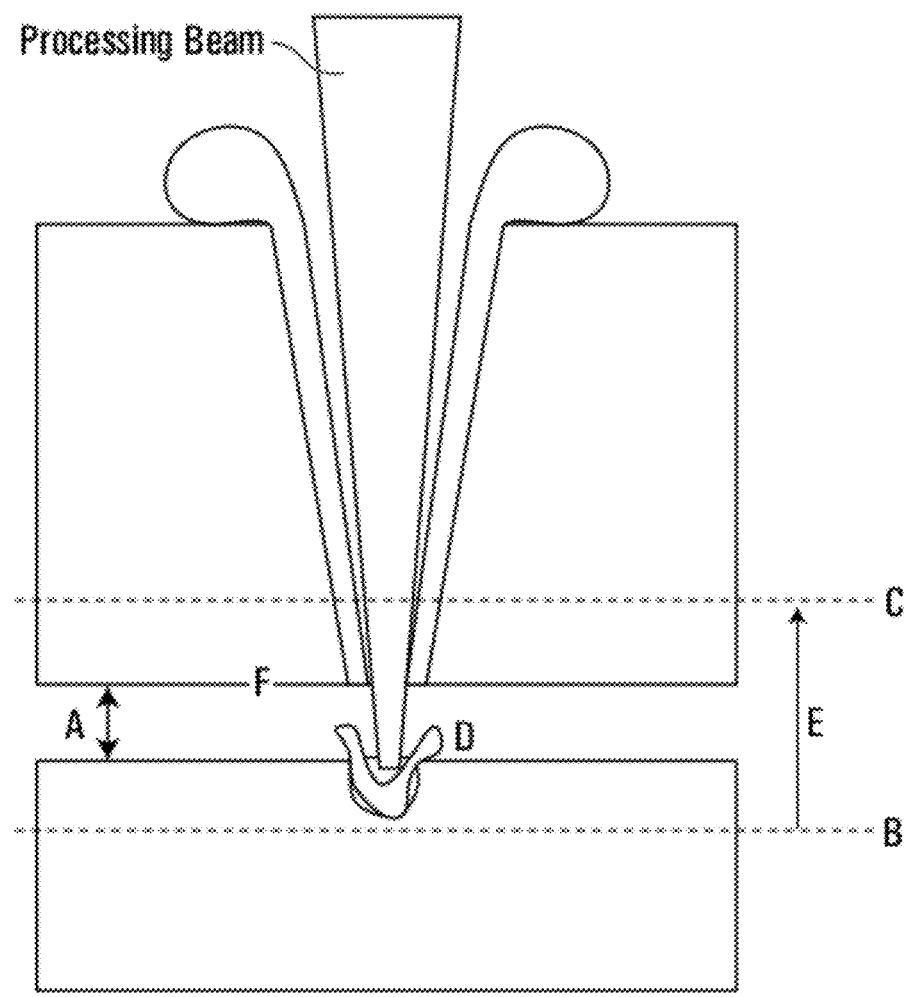
FIG. 23 is a schematic diagram showing how ICI can be used to assess fit-up and gap in laser lap welding.

In some embodiments, the sensitivity vs. depth is managed by locating the zero optical path length difference point below the area of interest in the sample instead of above it. This can be accomplished by increasing the length of the reference arm and updating the output of the imaging system to reflect the fact that shallower depths are now indicated by increasing fringe frequencies. The location of the zero optical path length difference point inside the material is demonstrated pictorially in FIGS. 21 and 23. In FIG. 21, the zero optical path length difference point D is set to be below the sample, and in particular below reflectors at A, B and C. Similarly, in FIG. 23, the zero optical path length difference point B is below the weld pool. In other implementations the zero optical path length difference point is configured to be located at a depth that is below the material being measured.

This approach utilizes the natural sensitivity vs. depth behaviour of the system (which, due to finite spectral resolution in the detector, tends to decrease with increasing path length difference) to counteract the natural sample reflectivity (which tends to decrease with depth). In this way, deeper structures in the sample (which tend to reflect less) are detected with greater sensitivity relative to superficial structures (which tend to reflect more). An additional advantage of this practice is that smoke, plasma, debris and other sources of light scattering proximal to the imaging system appear deeper in the image, are attenuated and do not wrap into the region of interest due to complex conjugate ambiguity. This differs from the teachings of art in the medical imaging field (e.g. optical coherence tomography) where complex conjugate ambiguity makes it undesirable to place the zero optical path length difference point inside or in some instances below, the sample.

In some embodiments, the zero optical path length difference point is located above the area of interest.

In some embodiments, the sensitivity vs. depth is managed by using Talbot band techniques to tailor the sensitivity vs. depth curve, for example, as demonstrated by Woods and Podoleanu. See Daniel Woods and Adrian Podoleanu, "Controlling the shape of Talbot bands' visibility," Opt. Express 16, 9654-9670 (2008); Adrian Gh. Podoleanu, "Unique interpretation of Talbot Bands and Fourier domain white light interferometry," Opt. Express 15, 9867-9876 (2007); Adrian Podoleanu and Daniel Woods, "Power-efficient Fourier domain optical coherence tomography setup for selection in the optical path difference sign using Talbot bands," Opt. Lett. 32, 2300-2302 (2007) all hereby incorporated by reference in their entirety. This approach allows for strong, adjustable attenuation of superficial reflectors and can be used to diminish bright surface reflections that may saturate the detector.

In some embodiments, the sensitivity vs. depth is managed by using nonlinear time gating, for example, as demonstrated by Muller et al (Matthew S. Muller, Paul J. L. Webster, and James M. Fraser, Optics Letters 32, 3336 (2007)) hereby incorporated by reference in its entirety. This approach utilizes nonlinear sum frequency generation to define a depth window of high sensitivity with reduced sensitivity outside it. With the window placed near sites of weak reflections, superficial reflections are diminished and prevented from saturating the detector.

In some embodiments, the sensitivity vs. depth is managed by accessing the analog fringe signal before final digitization, for example in a swept source imaging system, and then using direct hardware demodulation and/or filtering to attenuate certain fringe frequencies that correspond to depths where high reflectivity is expected while retaining sensitivity at depths where the signal is weaker. This can be accomplished by adding digital and/or analog filter elements to the signalling line between the detector and the image processor.

Four specific approaches to managing the sensitivity vs. depth have been described. In some embodiments, a combination of two, three or all four of the approaches are implemented. In addition, while described in the context of the embodiment of FIG. 5, it should be understood that any one or any combination of two or more of these approaches may be applied in conjunction with any of the other embodiments described or claimed herein.

Observation and Process Development of Laser Welding

In some embodiments, an apparatus such as the one shown in FIG. 14 is interfaced via the camera port or some other suitable optical access to the beam line inside a laser welding beam delivery system. The imaging and welding laser beams are combined with a dichroic mirror and focused through a common objective.

In some embodiments, this apparatus is applied to observe laser welding processes, such as keyhole welding processes, in some embodiments with feedback to the welding processes, and in some embodiments without any feedback to the welding processes.

In any of the embodiments of ICI described herein featuring feedback, the operation of closed loop feedback may be achieved using a feedback control law, or a selected one of a plurality of feedback control laws.

In any of the embodiments of ICI described herein featuring feedback, the material modification process may be configured to be able to operate using a selected one of a plurality of control laws, at least some of which are feedback control laws, and at least one of which is an open loop control law. In some embodiments, a hybrid control law is used that is open loop some of the time, and closed loop some of the time. Open loop mode may, for example, be achieved by selecting a control law which stipulates zero feedback data. It may be desired by an operator to not effect closed loop control for a variety of reasons. It is understood in the art that a control law for effecting a desired outcome can vary significantly dependant upon the goals of the operation. For example, it may be desired to measure using ICI the extent to which uncontrolled laser welding causes weld defects. By selecting a control law which stipulates zero feedback data, the system would be forced to operate as if there were no control. Thus ICI could be used to characterize and measure the performance of a standard laser welding system where, in a standard system, ICI based control would otherwise not be available. In other embodiments, it may be desired to effect a control law whereby the weld depth was modulated between a deeper penetration level, and a shallower penetration level. In other embodiments, it may be desired to effect a control law whereby only the worst case bounds of weld depth penetration were limited, allowing for open loop operation at times, and depth controlled operation only when penetration depth approached the limits of the control range.

By measuring the location reflectivity from the bottom of the keyhole (or other welding outcome) produced by the welding beam, a measure of the depth of the laser keyhole (or other welding outcome) can be produced. In some implementations, this might be achieved at rates up to and exceeding 300 kHz. This is a close approximation of the full depth of the laser weld. Pulsed laser welding experiments were performed while observing with an inline coherent imaging system like the one shown in FIG. 5, but with the feedback controller deactivated. It was found that the depth indicated by the ICI system during the process closely matches the depth of the weld seam that is revealed by cross sectioning, polishing and etching (the analysis procedures that are used by those of skill in the art). ICI data could therefore reduce or eliminate the need for this costly and destructive analysis step. Furthermore, such ICI data could also accelerate process development and provide 100% weld inspection and a permanent diagnostic record of the weld by storing the imaging data on a storage medium such as a hard disk drive or solid state disk. Feedback from ICI can lead to more productive welding equipment and enable laser welding where it was not possible or economical before.

This is because real time feedback provided by the imaging system may be used to change process variables in a way that compensates for variations in feedstock (e.g. poor fit up) and instabilities (e.g. variable weld depth) in the process as it is accelerated to higher speeds and/or pushed to greater depths. This may extend the usability of laser welding systems to include lower cost input feedstock, higher processing speeds and/or deeper penetration while maintaining acceptable quality.

The transient effects during the start or finish of a welding procedure may have a negative effect on the outcome of a weld (e.g. inconsistent seam depth, e.g. underfill). In one embodiment, feedback provided by the imaging system may be used to reduce these defects by controlling one or more process parameters to compensate for the transient behaviour of the weld at its start, at its finish or both. In a specific example, the system described in FIG. 5 measures the depth of the welding keyhole throughout a lap weld of two plates of steel. At the beginning of the weld, the imaging data indicates that the keyhole has not penetrated to the selected welding depth. This data is processed by the feedback controller with a result of slowing the material feed rate relative to the processing beam. This has the effect of allowing the keyhole to penetrate closer to the selected depth than it would have if no adjustment to the speed had been made.

Multiplexing the Imaging System

In some embodiments, a single machining laser (more generally a single processing beam source) is used to process multiple samples in multiple processing locations, and the machining laser may be paired with one or more ICI systems. This may make better use of the relatively expensive machining laser, and makes better use of the ICI system's capabilities. In these situations, the sampled data from the set of samples is coordinated with the directivity of the machining laser, such that sampled data may be associated with a specific sample.

Figure 25A:
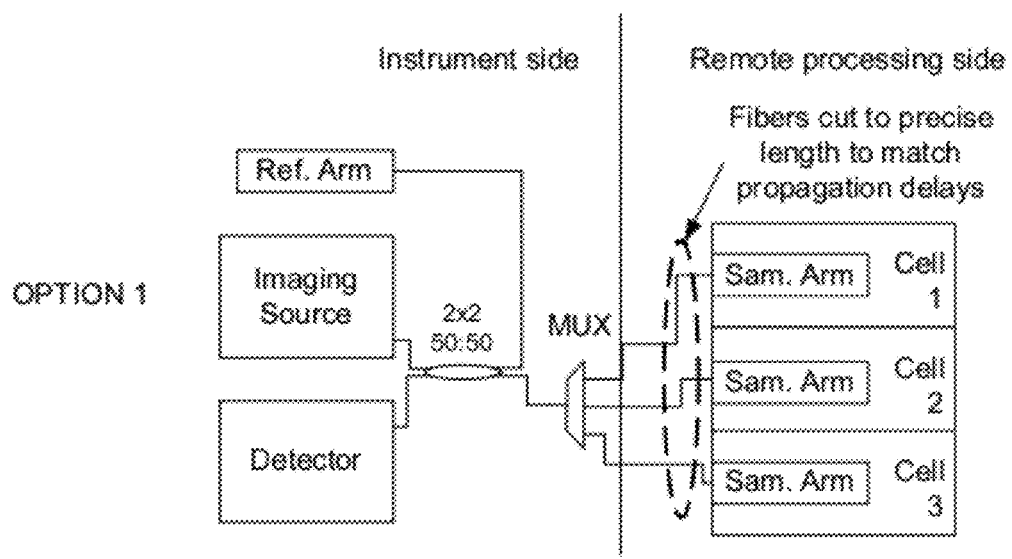
FIG. 25 depicts various options for using the same ICI system with multiple sample locations.

In some embodiments, a single reference arm, and a respective sample arm is used with a precisely matched propagation delay. An example of this is depicted in FIG. 25A. A unique challenge however, from the perspective of multiplexed ICI functionality, is the ability to match the overall propagation delay between the set of processing locations such that a single fixed reference arm could be used. This challenge stems from the fact that runs of optical fibre may be long and the multiplexor may add a different (e.g. variable) delay for each multiplexed channel.

Figure 25B:
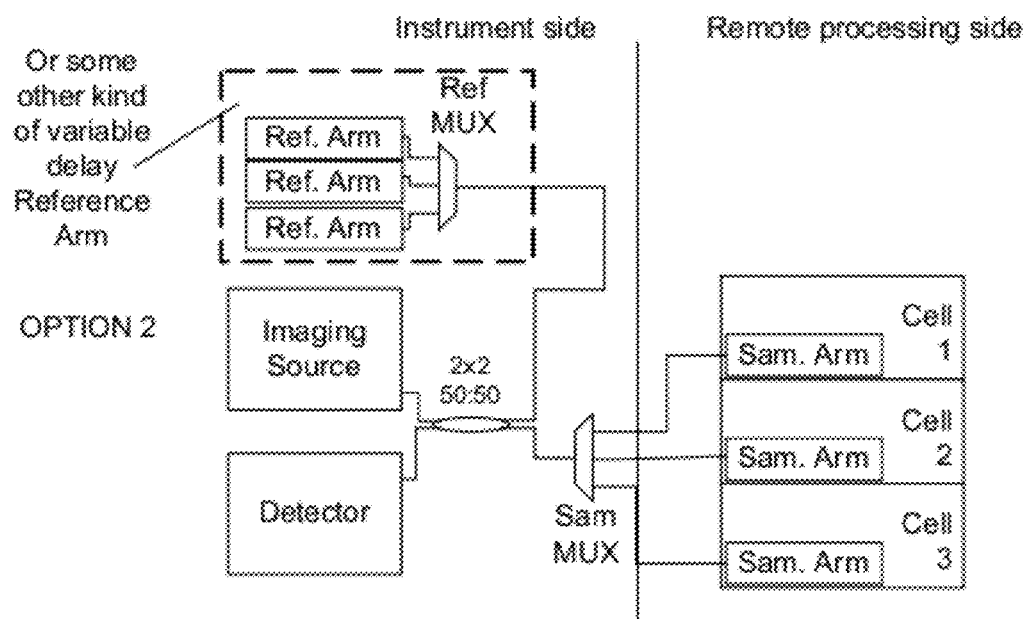
Figure 25C:
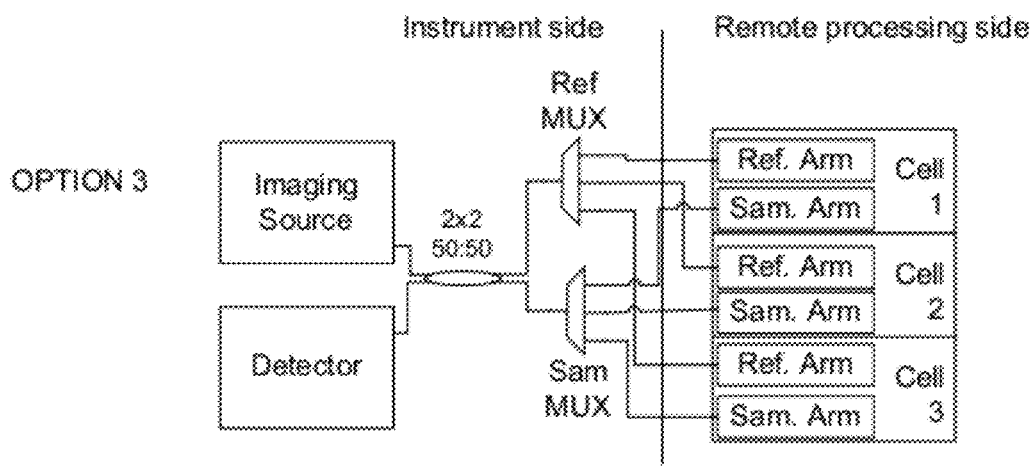

In some embodiments, rather than using matched sample arm paths, a dynamic optical path switch in the reference path is made at the same time as the main processing beam path is switched. This approach allows for an optimized reference path for each sample and the freedom to locate the reference arms away from any vibrations at the processing location (e.g. on the robot). An example of this is depicted in FIG. 25B. Here, the reference multiplexer is used to switch between various fixed reference arms. Alternatively some other kind of variable reference arm may be employed. In some embodiments, separate reference arms are provided at each processing location. Sample and reference arms are connected to one side of a 2×2 evanescent mode coupler and the connections from the other side are multiplexed (ie switch or selector) from each processing location to the common illumination and detection channels. These channels are not sensitive to optical path length in most practical cases. This approach also minimizes optical losses. Optical shutters may also be used in the sample and reference arms as an alternative or in addition to an optical switch, selector or multiplexer, The operation of all dynamic elements are coordinated with the timing of the main processing beam directivity to properly isolate any undesired optical reflection signals. An example of this approach is depicted in FIG. 25C.

Figure 25D:
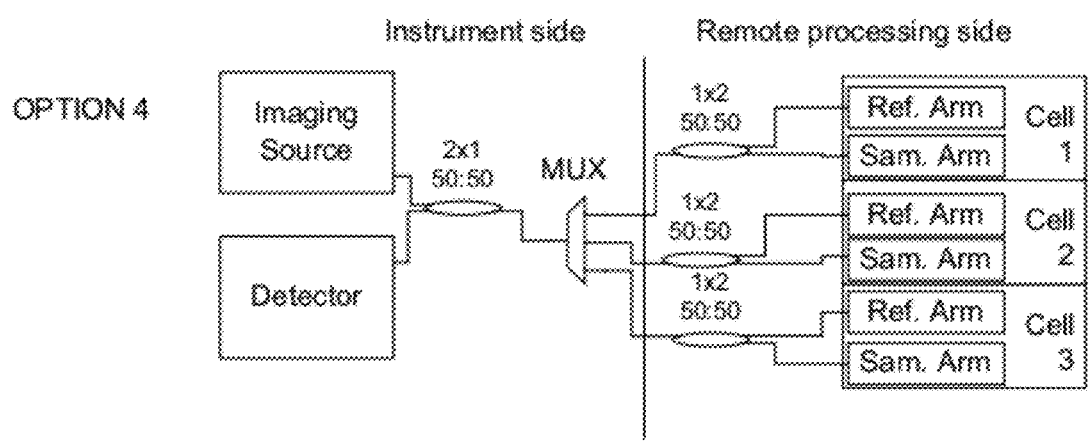

In some embodiments, the illumination and detection channels are connected to one side of a 2×1 evanescent mode coupler, the output of which is multiplexed to the different processing locations where it is connected to one side of a 1×2 evanescent mode coupler whose two outputs are connected to a separate reference arm and the sample arm. This approach eliminates the complexity and expense of needing two optical multiplexers. Optical shutters may also be used in the sample and reference arms as an alternative or in addition to an optical switch, selector or multiplexer The operation of all dynamic elements is coordinated with the timing of the main processing beam directivity to properly isolate any undesired optical reflection signals. An example of this approach is depicted in FIG. 25D.

In FIGS. 25A, 25B, 25C and 25D, each cell is a different laser processing location. "Laser Cell" is a common term in the industry that describes an enclosed area in which material is processed. 50:50 splitters are depicted here, but other splitting ratios may be used to adjust the dynamic range and sensitivity of the system.

In some embodiments of the invention, the reference arm is configured such that the path length of the reference arm is adjustable, in some cases during operation of the system, or alternatively while the system is not operating. An adjustable reference arm allows for simpler operation of the system as the reference arm path length could be tuned as needed. Correspondingly, in some embodiments, adjustability of the path length on the primary path is provided. An adjustable reference arm may be used, for example, for one or more of:

compensate for motion in the sample;

adjust the area of interest in the sample to a higher or lower area;

measure multiple samples in a switched or multi arm ICI system;

easily and quickly configure the ICI system in a surgical context.

An adjustable optical reference arm may be achieved by using a stretchable optical media, using motorized free space reflector and coupling apparatus, or using multi-reflection mirror mechanism to name a few specific examples.

Manual or automatic adjustment of adjustable optical path length elements may be performed during operation of the ICI system. Such adjustment would be beneficial in order to allow an ability to adjust how ICI images are captured during run time of the system.

In some embodiments, the ICI system is used to track a location of an internal reflective interface, or some other point of interest that may change over time. Then, optical path length in the reference or sample arm are adjusted such that the location of the internal reflective interface (or some other point of interest) becomes the zero optical path length difference point, such that the zero optical path length difference point is dynamically determined. Alternatively, the zero optical path length difference point can be selected to have a desired relative position to the location of the internal reflective interface (or other point of interest).

Imaging Breakthrough/Refill after Breakthrough

Lasers are commonly used to perforate metals, polymers, tissue and ceramic and other materials in processes like percussion drilling and trepan drilling. In some embodiments, ICI systems are used to perform one or a combination of:

a) tracking the bottom of a hole during drilling;

b) controlling the speed of perforation;

c) observing the point when the material is perforated;

d) anticipating the point in time at which the laser will perforate the material;

e) adjusting the laser process to avoid damage to surfaces below the new hole; and f) confirming that the hole is not refilled after the laser is turned off;

g) Controlling drilling, cutting or welding to a selected depth; and h) Controlling drilling, cutting or welding to a selected depth relative to a selected material interface; and i) generating an indication of impending breakthrough in a process of laser drilling, laser cutting or laser welding.

Advantageously, ICI systems are able to perform these functions without physical access to the distal side of the part being perforated. This is a considerable advantage over many existing breakthrough detection techniques.

Figure 22:
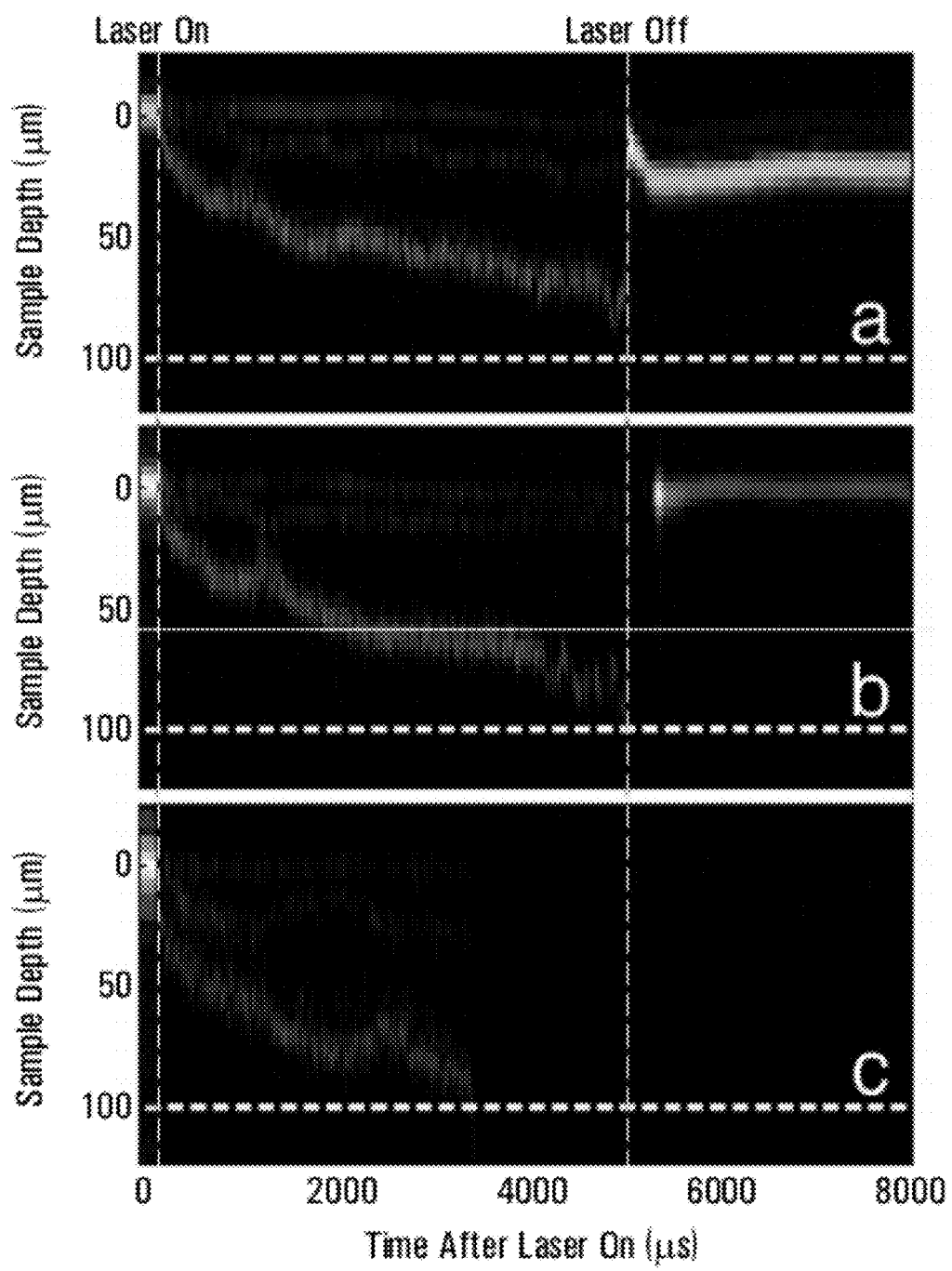
FIG. 22 shows ICI generated images from single pulse (5 ms duration indicated by vertical lines) oxygen assisted percussion drilling in stainless steel foils.

By way of example, the ICI system shown in FIG. 14 can be interfaced to a laser drilling system via a camera port or other suitable optical access to the beam line where it is combined with the processing beam by way of a dichroic mirror. To demonstrate its ability to track the bottom of the hole during drilling and observe breakthrough, individual 5 ms pulses of 1070 nm light were applied to steel foils with thickness of 102 micrometers. The imaging and drilling foci were previously aligned using a CMOS detector array. Perforation could be controlled with the applied pulse energy and oxygen assist gas pressure. M-mode images from three example experiments are shown in FIG. 22. FIG. 22 shows ICI images from single pulse (5 ms duration indicated by vertical red lines) oxygen assisted percussion drilling in stainless steel foils. The horizontal dashed line indicates the thickness of the foil. In tile "a" of the FIG. 22, a 77 mJ pulse fails to perforate the foil, but the foil is nearly perforated (within approximately 15 um) before the drilling pulse ends and the hole refills with melt. In tile "b", a 77 mJ pulse briefly perforates the foil very close to the end of the drilling pulse. At this point, assist gas begins to clear the hole leaving several hundred microseconds after the pulse where little signal is registered by the ICI system. After this period, the hole does refill as indicated by the signature of a single interface at or near the original surface depth. In tile "c", a stronger drilling pulse is used causing the hole to be perforated in a few milliseconds. More specifically, increasing the pulse energy to 100 mJ creates a hole in ~3.5 ms that remains open after the pulse. Since the drilling pulse has held the hole open long enough for the assist gas to clear the peripheral melt, the hole does not refill and this is indicated by the ICI image, confirming that a successful perforation has been made. These interpretations are confirmed by measurements of optical power transmitted through the foil and detected with a high speed photodiode. The presence of a signal originating from the depth of the distal wall of the material being perforated after the drilling has finished could indicate the presence of dross and or that the exit hole diameter is comparable to that of the imaging beam focus.

With the use of a feedback processor such as the one detailed in FIG. 5, an ICI system can control the rate of perforation by signalling a change in process parameters (e.g. pulse energy) based on the processed interferometry signals it measures. Similarly, upon detection of breakthrough, the feedback processor can signal for the drilling laser to stop, optionally after a selected overdrilling period. This has an important feature of being able to reduce the probability of "back wall strike"-type damage to materials present on the distal side of the material being perforated. This capability is a considerable advantage provided by ICI systems in application areas such as the fabrication of cooling holes in gas turbines.

This signature of breakthrough is different in different materials. In metal, it may be observed that immediately before perforation, an apparent acceleration in the penetration rate of the drilling laser occurs.

This can be used as a signature to indicate imminent perforation and allow preparations to be made to halt or otherwise change the process near the point of perforation. If the process is halted immediately before perforation, chemical (e.g. light acid etch) or other procedure may be used to complete the hole. Furthermore, flow of liquid and subsequent obstruction of the hole after fusion can be observed. ICI systems may be used to generate a record of these events, and/or to generate an alarm, annunciation, warning and/or to requisition additional processing to clear the hole.

In another embodiment, an ICI system is used to control laser drilling of printed circuit board vias and/or trench cutting in printed circuit boards. One skilled in the art will know that these structures are often formed through penetration of one or more layers of conductive and/or insulating material. ICI image processors are capable of determining how deeply the materials have been penetrated by the process and the proximity of the process to the various layers of material. Specifically, in the imaging data subsurface layers may be identified during drilling by their tendency to appear to rise in the image as noted by label AI in FIG. 11B. Simultaneously, the bottom of the hole appears to fall (MF). The subsurface layer is perforated when these two signatures meet as demonstrated in FIG. 11A at point P. This feature (which we refer to here as a "scissor feature") and its precursors (such as the features highlighted by MF and AI in FIG. 11B) have substantial utility for feedback control in many applications which, in various embodiments include, but are not limited to, cutting, drilling, laser surgery and any other material removal technique in semi- and/or fully-transparent media. Detecting scissor features and their precursors allows the image processor and/or the feedback controller to start, stop, slow and/or accelerate the drilling process by effecting changes to one or more process variables and/or guide the material modification process to locations relative to subsurface features in the material being modified, even if such features were not characterized prior to the commencement of processing. These capabilities are advantageous because they allow for faster and/or more accurate overall processing of a material. In some embodiments, ICI imaging data provides guidance to selected surgical margins about tissue(s) that are sensitive to laser damage, thus it enables safer laser surgical procedures that could not be easily performed without its benefits.

In another embodiment, an ICI system is used to detect breakthrough of a welding beam and the gap between the two materials in real time during a welding process. This information is interpreted by the electronics. In some embodiments, a signal output is generated for receipt by an operator and/or additional process control electronics. For example, the ICI system shown in FIG. 14 can be interfaced with the beam delivery subsystem (via a camera port/other optical access and a dichroic mirror) of a laser keyhole welding machine applied for lap welding two sheets of metal together (see FIG. 22). In this example process, it is desired to determine when the weld penetrates the first material (F), the fit up of the two surfaces (A) at the point of penetration and the further penetration of the weld into the second material (D). By adjusting the length of the reference arm (416), the zero optical path length difference point B is located slightly below (a sufficient distance below such that complex conjugate ambiguity artifacts in the image do not occur) the expected maximum penetration depth of the weld. This is useful to enhance deeper signals from within the material because deeper features naturally reflect less light into the imaging system and the system is more sensitive at shorter optical path differences.

The imaging system has a single sided field of view range represented by "E". As the material is penetrated, a signal begins to be registered as the proximal material is penetrated to depth C and enters the field of view. As the process reaches depth F, the imaging system may register an acceleration of penetration as the distal wall of the proximal material loses its mechanical strength and deforms. As the distal wall is penetrated at depth F, its signal is attenuated or it vanishes completely indicating breakthrough. At this point, the imaging system registers a reflection from the proximal wall of the distal material. The difference in axial position from these two reflections indicates the welding gap/fit up of the two pieces (A) of material which is an output that can be displayed, stored and/or relayed to a feedback controller. As the process beam continues to penetrate into the distal material, depth may be imaged as before and so the final depth of the weld inside the distal material can also be measured, displayed, recorded on a storage medium and/or relayed to a feedback controller.

In addition, while described in the context of the embodiment of FIG. 14, it should be understood that any one or any combination of two or more of these approaches may be applied in conjunction with any of the other embodiments described or claimed herein. This approach can be applied to embodiments with or without feedback.

Intentionally Defocused/Large Imaging Beam to Determine Lowest or Highest Depth within a Region In some embodiments, the ICI system is configured such that the imaging beam illuminates an area or volume of the sample that encompasses multiple reflective features of the sample that are at different axial heights, or different transverse displacements relative to the center axis of the imaging beam, or any combination thereof. In some instances, the reflective features of the sample may be entirely on the surface of the sample. In other instances, the reflective features may be related to internal structures, interfaces, objects or other reflective elements of the sample. This allows for the simultaneous detection of multiple feature heights within the illuminated area or volume of the imaging beam which may be measured without the need for transverse scanning or an additional QA step after processing. In some embodiments of the invention, significant efficiency may be obtained when the imaging beam is delivered coaxially with an optional sample processing beam.

As a specific example, in one embodiment, an ICI system such as the one depicted in FIG. 14 is connected to an optical access port on the laser beam delivery system for a device that produces dimples in metals. In this embodiment, the sample arm collimator's (407 in FIG. 14) focal length is chosen to be short in order to produce a small imaging beam diameter inside the delivery head before it reaches the focusing objective (not shown). The imaging and processing beams are combined by way of a dichroic mirror. In this example, the processing beam may, for example, be a carbon dioxide laser, a Nd:YAG laser, a fibre laser or any other laser capable of producing dimples in metals. For this example, it is assumed that the sample arm has a sample arm collimator lens and a sample arm objective (that also functions as the objective for the modification laser) such as depicted in the embodiment of FIG. 5 (see elements 351 and 314). At the sample, the imaging beam has an approximate diameter equal to the product of the mode field diameter of the imaging fiber (the fiber between elements 402 and fiber collimator 409 of the reference arm 416)) and the ratio of the sample objective lens:sample arm collimator lens focal lengths (lens 314,353 of FIG. 5). For a typical mode field diameter of 5 um and a sample objective focal length of 100 mm, a sample arm collimator focal length of 5 mm would produce a 100 um diameter spot on the sample. Additionally, the sample spot diameter can be further modified by varying the distance between the sample arm collimator lens and the fiber tip, but this may not result in optimal light collection efficiency. When the imaging beam reaches the sample, portions of the beam are back-reflected from a plurality of depths. These reflections are received by the imaging system and create an interferometry output based on their optical path length. This output is detected and electronically processed by a signal processor device by way of algorithms such as the homodyne filter algorithm, or some combination of Fourier transforms with spectral reshaping as necessary, interpolative resampling as necessary, Kaiser-Bessel filtering (e.g. Vergnole et al.—see Sébastien Vergnole, Daniel Lévesque, and Guy Lamouche, Optics Express 18, 10446-61 (2010), hereby incorporated by reference in its entirety) and generate a representation of the reflectivity of the sample as a function of one or more depths. This measurement can be acquired at rates in excess of 300 kHz using available detector technology. Image processing rates in excess of 600 kHz have been achieved by processing the image data on graphics processor units. In some embodiments, this technique is applied to real-time process control.

In the specific example of laser created dimples, these structures are utilized to create a gap between two plates that are later lap welded together. The height of the dimple above the original surface is an important indicator of the gap that is to be expected during the subsequent welding process. Dimples are often created in groups of 2 or more. In some embodiments, using in-situ measurement of the final dimple geometry, detected inadequacies in dimple heights are fed from the image processing system to a feedback controller (such as in FIG. 5) to cause a change in the dimple formation process parameters.

FIG. 21 shows an example of an imaging beam that is applied to the sample such that its diameter is larger than a feature of interest. Reflections are measured from several depths in the sample (A-C). These depths may be simultaneously measured in a single optical acquisition (axial scan also called A-scan). When the imaging beam is delivered coaxially with the beam used to process these features, it can rapidly measure the height and depth of the features without the need for an additional measurement step. The representation of the reflectivity of the sample as a function of one or more depths is shown schematically on the right hand side of FIG. 21. It can be seen that there is a respective peak in the A-scan intensity that represent each of A: height of dimple tip, B: height of virgin surface, and C: height of dimple trough. The above-discussed height of the dimple is represented by A-B. Other surfaces at other heights in the feature may generate a signature in the A-scan, but these have been omitted in FIG. 21 for clarity.

In addition, while described in the context of the embodiment of FIG. 14, it should be understood that any one or any combination of two or more of these approaches may be applied in conjunction with any of the other embodiments described or claimed herein. This approach can be applied to embodiments with or without feedback control.

In FIG. 21, the previously introduced practice of placing the zero optical path length difference point (D) inside the material being measured is also demonstrated. If the reflection from depth A is much brighter than depth C, then this configuration improves image quality since spectral domain coherent imaging systems typically register reflections from larger optical path differences with less sensitivity thereby shifting the dynamic range of the imaging system and reducing potential saturation.

Figure 26:
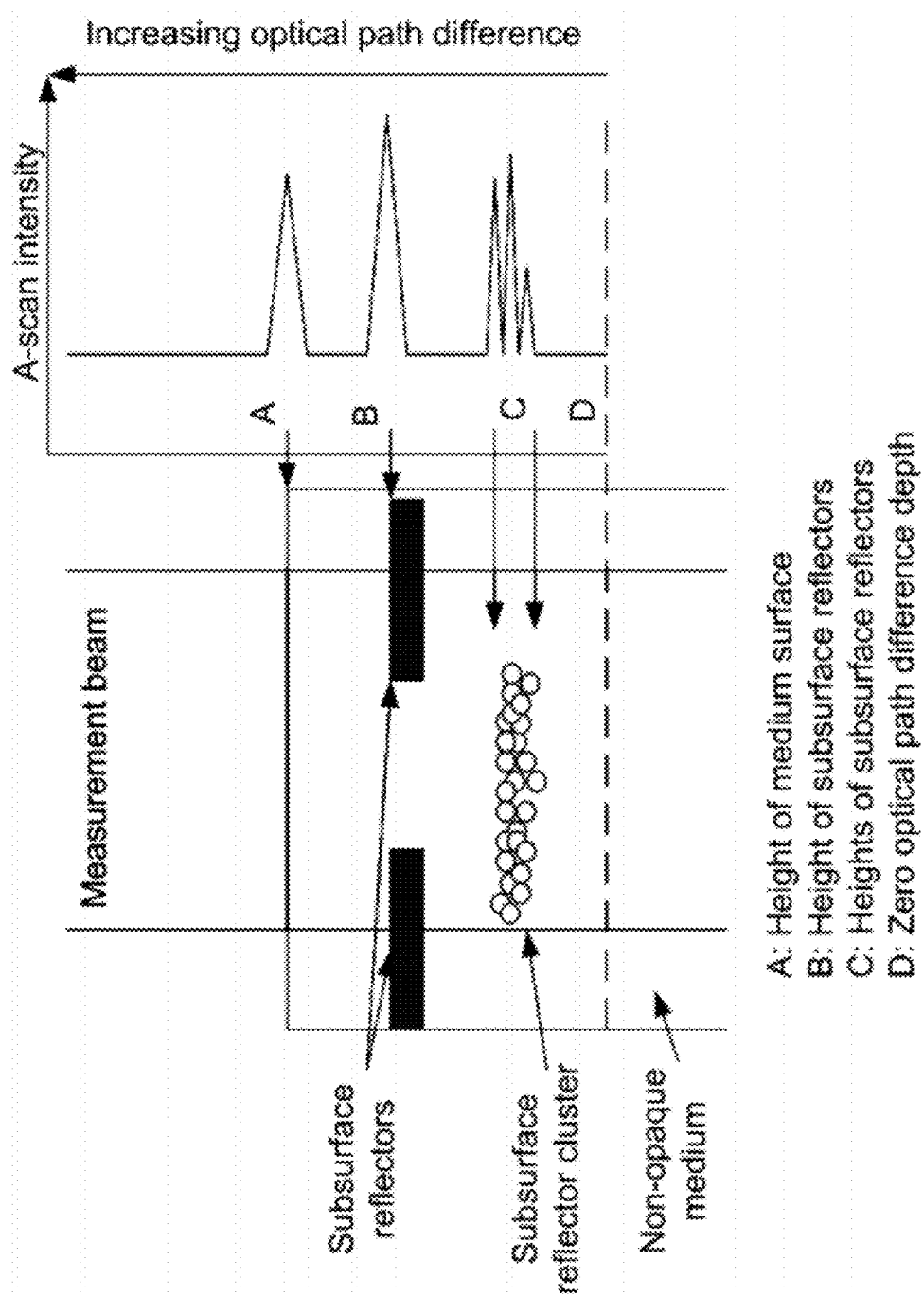
FIG. 26 depicts the use of an ICI system to measure heights of features below the surface of the sample.

The methods described herein to measure surface feature heights on a sample may also be used to measure heights of features below the surface of the sample, as shown by way of example in FIG. 26. In some embodiments, this can be an effective way to characterize material in the immediate region of the processing beam. In some embodiments, this method may be used to align a processing beam.

Implementation Example Showing Verification of Drilling Control

Using the fully automatic depth control provided by the Inline Coherent Imaging system shown in FIG. 5, 14 holes were drilled at depths that vary steadily by 30 micrometer from hole to hole. The homodyne filter algorithm running on a PC (one embodiment of image processing electronics, 332) was used to efficiently process the raw imaging data from the silicon line camera (330) and make a determination as to whether further machining laser exposure was required to achieve the desired depth. A user programmed the desired depth(s) for the series of holes into the PC. The PC read this programming and synthesized the appropriate homodyne waveforms to mix with the raw imaging data to obtain the sample reflectivity at the target depth. Through the course of drilling the hole, when a selected threshold was met from the homodyne output (in this case, 5 times the RMS intensity of the noise floor), the PC signals the feedback controller (334) to cease the process. In this embodiment, the feedback controller consisted of a digital output subsystem of the PC (National Instruments PCI-6229) and a function generator (Tektronix AFG3022B). This feedback controller directed a modulated CW fiber laser (320) to emit pulses (duration on the order of 100 microseconds) that drill the sample. This system is capable of producing an open loop feedback response time better than 300 microseconds.

Figure 24:
FIG. 24 depicts a scan by a separate scanning optical coherence tomography system to verify the accuracy of ICI controlled laser drilling.

To confirm the result, a separate scanning optical coherence tomography system was used to measure the topology of the processed sample. Aligned to scan within the plane in which the holes were drilled, the system measures the depth of the drilled holes. The resulting image is depicted in FIG. 24, and shows 14 holes with depths that vary steadily by 30 micrometers from hole to hole.

Scanner Correction

In some embodiments, the imaging and processing beams may be directed towards the sample by way of active scanning optics and a lens. As one of normal skill in the art would appreciate, scanning the processing beam allows for fast and precise movement of the optical focus which is desirable for many material processing applications (e.g. automotive welding). The inclusion of scanners in the material processor subsystems of ICI augments scanned material processing with some or all of the many advantages of ICI systems described herein. The scanning optics/lens combination may cause modulations in the optical path length to the material as the beams are scanned from one place to another that, in one example, cause a flat surface to appear curved. Managing these modulations optically may relax design requirements for depth field of view and/or for more computationally efficient feedback calculations within the ICI system. In some applications, modulations can be managed digitally by applying a depth offset (e.g. within the image and/or feedback processors) that is correlated with the scan optic position.

In one embodiment, the path length modulations are substantially compensated for by adjusting the reference arm length by an amount equal to or approximating the expected and/or measured modulation generated by scan position. Such an adjustment could be by way of a motorized translation stage, a piezoelectric element, stretching the sample or reference fiber, an electromagnetic solenoid or voice coil and/or by including several reference mirrors that can be introduced or removed from the reference arm beam path. Additional adjustment can be included in the image processing step by adding a digital offset to the reported depth measurement equal to the desired correction. In some embodiments, the path length modulations present are directly measured for the entire area and/or path to be processed on the sample by the imaging components of ICI. This may be accomplished by, for example, placing virgin feedstock in the processing system and recording ICI data as the optics are scanned through the motion paths that are to be used when processing the material. The difference between the surface topology indicated and/or tracked in this data and the known surface topology of the sample may be used as a correction function for optical and/or digital management of the scan-induced optical path length modulations.

The imaging system collects data during this program noting the location of the virgin surface. It may be advantageous to use the path length adjusting hardware in the sample and/or reference arms to follow the virgin surface if its path length changes by more than the total axial field of view of the system. Iterative adjustment of the correction can be made until the level of the virgin surface appears sufficiently flat for use of image processing algorithms while the scan program executes.

The transverse scan position of a focused beam through a scan lens approximates the product of the lens effective focal length and the scan angle expressed in radians. The chromatic aberration (i.e. focal length changes as a function of wavelength) of the lens may cause a transverse spatial walkoff between the imaging and processing beams as they are scanned across the material if both beams are introduced into the lens at the same scan angle. In some embodiments, the imaging beam's scan angle may be pre-corrected before being combined with the process beam by adding small angular deviations to the imaging beam using galvanometers or other active elements inserted into the imaging beam path between the sample collimator. These active elements would be controlled to be synchronized with the main scanning optics that scan the combined beams. Verification of this correction can be accomplished by focusing both beams onto a CCD or CMOS detector array or other beam profiling equipment such as a PRIMES FocusMonitor.

Low coherence interferometry can also be performed with a spectrally swept optical source (called "swept source", "optical frequency domain imaging" and/or sometimes "Fourier domain mode-locked") configurations instead, or in addition to spectrometer-based (called "spectral" or "Fourier domain") configurations. These approaches are distinguished and compared by Choma et al (Michael Choma, Marinko Sarunic, Changhuei Yang, and Joseph Izatt, Optics Express 11, 2183-9 (2003) hereby incorporated by reference in its entirety). It is understood that either or both of these approaches may be used with any of the inline coherent imaging systems described and claimed herein. Persons of normal skill will further appreciate that these two approaches (when used together or separately) respond differently to motion present in the sample as discussed by Yun et al (S. H. Yun, G. J. Tearney, J. F. de Boer, and B. E. Bouma, Optics Express 12, 2977-2998 (2008). hereby incorporated by reference in its entirety). The use of one or a combination of these techniques in ICI embodiments is selected based the speed of the moving objects (see Yun et al), the need for isolation of the imaging sensors from optical emissions from the process (spectrometer detection is advantageous here), the imaging rate (currently, swept sources may image more rapidly than spectrometers as discussed by Wieser et al Wolfgang Wieser, Benjamin R Biedermann, Thomas Klein, Christoph M Eigenwillig, and Robert Huber, Optics Express 18, 14685-704 (2010). hereby incorporated by reference in its entirety), and the overall cost and complexity of the device (currently, swept sources are relatively complex and expensive and the cost of using both techniques is additive).

Figure 27:
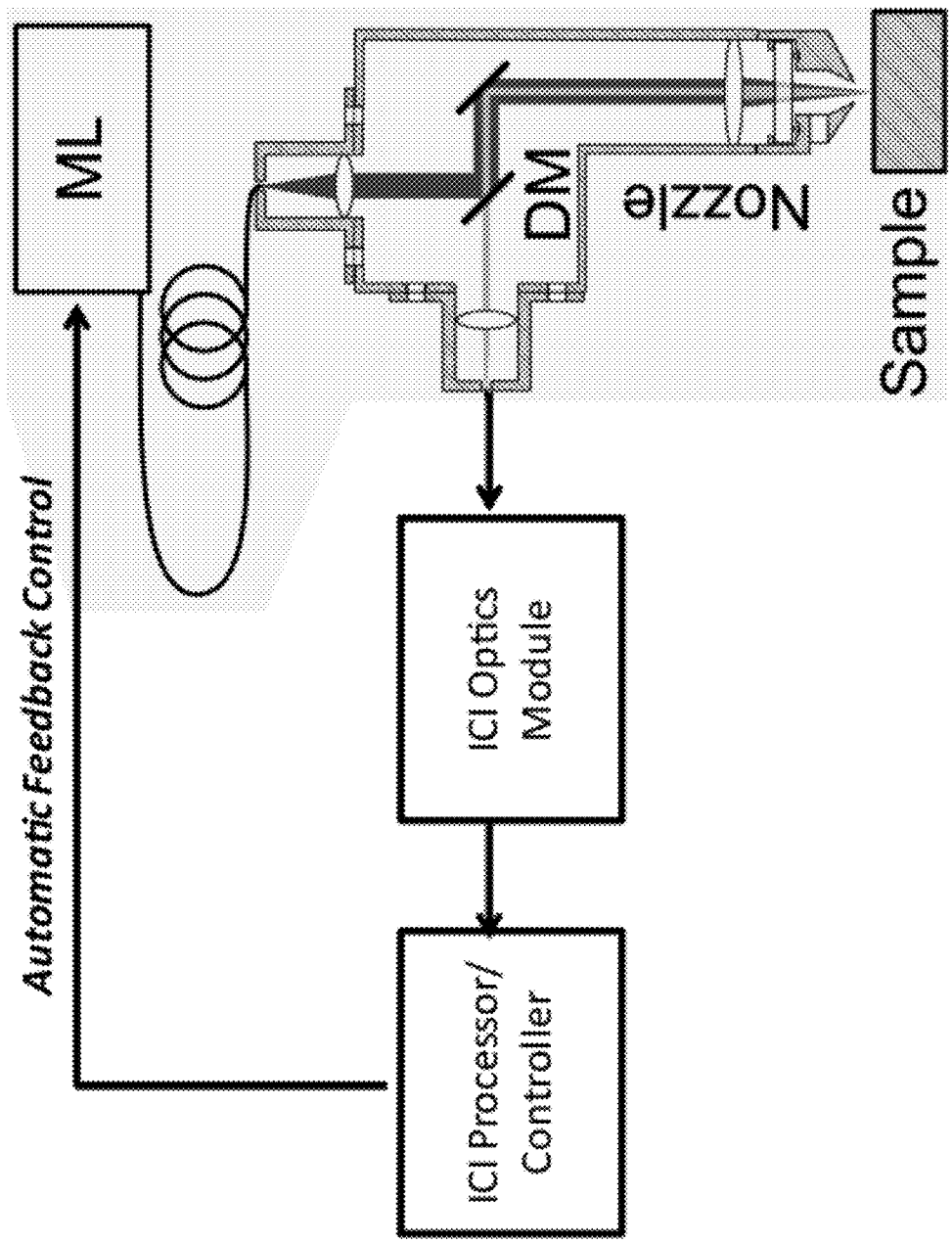
FIG. 27 is a block diagram of another embodiment wherein the ICI system directly controls the machining laser.

FIG. 27 is a schematic block diagram of another embodiment. Shown is a modification laser (ML) that generates a modification beam that passes through a fiber and lens on the way to a dichroic mirror (DM) where it is combined with an imaging beam from ICI optics module. The combined beams are now substantially co-axial. They are reflected by a mirror through a common objective lens in the nozzle to the sample. Imaging light reflected off the sample passes back to the ICI optics module. The ICI Optics module has an output to an ICI processor controller which generates an automatic feedback control for the ML, and which more generally generates a control signal to control at least one processing parameter.

In the embodiment of FIG. 27, the ICI system is comprised of two elements; an ICI optics module and an ICI processor/controller. The ICI optics module comprises the electro optical elements of the ICI system, and interfaces optically with the nozzle of a laser material processing system, and interfaces electrically with the ICI processor/controller. The ICI processor/controller is responsible for the processing of image data, and for generation of control signals for the operation of the machining laser. The ICI modules may be combined together, or may be combined with other elements of the system.

Figure 28:
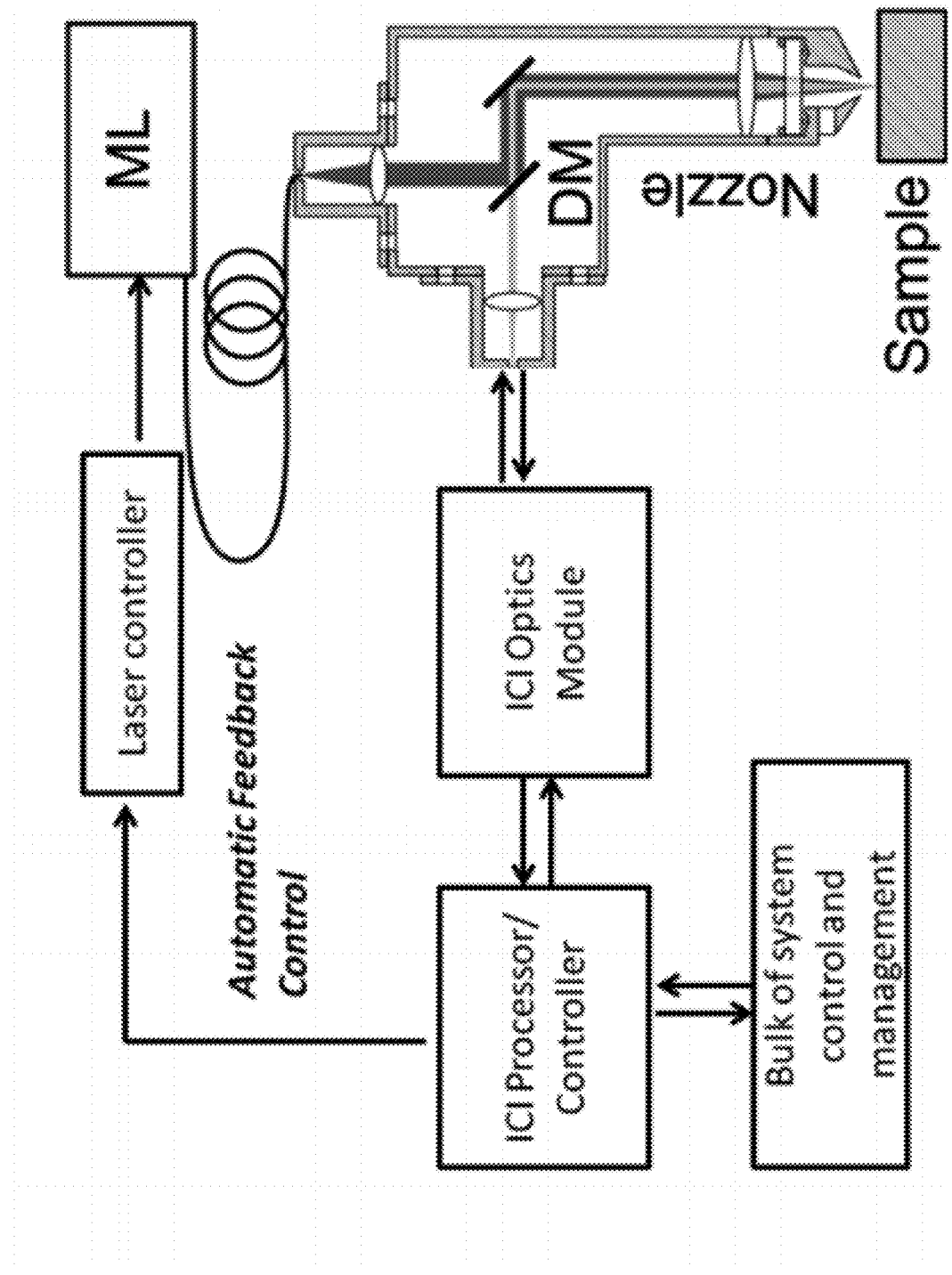
FIG. 28 is a block diagram of another embodiment wherein the ICI system interfaces indirectly controls the machining laser via a laser controller, and also interfaces other system control and/or management components (e.g. Robot motion control, material feed control, etc.).

In another embodiment of the invention, the ICI system may optionally be configured to interface with additional system elements, as is shown in FIG. 28. The ICI processor/controller may also interface electrically with a laser controller, and may provide control signals to the laser controller for the operation of the machining laser. The ICI processor/controller may interface with the other aspects of the overall laser material processing system, referred to as "bulk of system control and management". These additional system aspects may include material control, feed control, nozzle position control, gas flow control, and other aspects as may be required in an individual implementation.

Additional similar embodiments may be considered to incorporate operation with multiple samples and nozzles and/or different numbers of turning mirrors in the nozzle and/or different ordering of turning mirrors in the nozzle. These would be considered as equivalent to one of normal skill in the art.

To enable fully automatic feedback in pulsed laser machining, inline coherent imaging is used to output appropriate information to a specially designed image processor and feedback controller. For example, in some embodiments, the imaging window of the inline coherent imaging system is synchronized to a specific time delay relative to the beginning of the material modification optical pulse. The optimal delay depends on the kind of feedback that is desired as well as the objectives of the material modification process. Feeding back off the intrapulse (i.e., while the material modification source light is incident on the material) measurements yields a different result than after the material has relaxed. Intrapulse feedback may be used to control the total depth of penetration of the material modification process. In particular, intrapulse feedback benefits from very fast feedback response (response times on the order of 1-100 microseconds) for good accuracy because of the speed at which the processing beam may modify the material. Feedback from later times (i.e., when the material modification light source is not incident on the sample) is used to control the final morphology of the hole where the relaxed geometry of the sample (e.g. metal) is of concern.

In embodiments that use a quasicontinuous material modification light source, synchronization of the imaging system to the start of the material modification process is important for automatic feedback. In some embodiments, image acquisition of the sample before material modification begins is useful for allowing feedback relative to the virgin sample position and/or optical backscattering properties. For example, feedback to control modification relative to the top of the sample can be done on the fly. In addition, virgin optical backscattering properties can be used to adjust image processing parameters and/or feedback control algorithms to enable robust feedback for inhomogeneous materials.

In the inline coherent imaging optical unit, feedback for practical machining processes is significantly enabled by the use of a common focal objective to deliver both imaging and machining light to the sample. This makes integration with existing machining platforms and technology in the market significantly easier and less expensive than if one were to try and deliver imaging and machining light to the sample using separate focal objectives, and in some embodiments, an additional dichroic mirror between the sample and the objectives. In particular, delivery of process gas, damage to the dichroic mirror from process ejecta and dispersion compensation are all hindered by the latter approach. Inline coherent imaging systems avoid this problem by using a common focal objective to deliver both imaging and machining light to the sample. In some embodiments, integration into existing systems is considerably aided by operating the imaging light source in the spectral region between 400 and 950 nm as existing camera port hardware is often compatible with such wavelengths. Additionally, this spectral region allows for faster and/or more sensitive silicon based detector hardware to be used.

The image processor design and configuration in embodiments of inline coherent imaging differs from those taught in other applications of low coherence interferometry (such as optical coherence tomography). In ICI imaging systems, it is not suitable to buffer several thousand spectral acquisitions before processing as is commonly the practice in OCT. In some embodiments, the ICI systems acquire spectra in sets of 1 to 100 to reduce feedback latency time. Specialized image processing algorithms, online interface detection and a feedback controller are required, as well as appropriate algorithms to reduce the unprocessed imaging information to one or few output parameters by identifying selected interfaces in the sample that indicate process conditions such as depth of material removed, depth of material remaining, change in material height, change in material optical properties, change in material thickness.

When processing opaque materials, the bottom of the machined feature can often be positively identified by tracking algorithms as the first signal with intensity above a selected threshold as the algorithm traverses from deepest depth to shallowest. In some cases, multiply scattered photons will be collected by the imaging system in sufficient quantity as to falsely trigger this condition. Under these circumstances, the bottom of the hole may be positively identified by tracking algorithms as the first peak above a selected threshold as the algorithm traverses from deepest depth to shallowest. In some embodiments, image processing algorithms may average the results of one or more acquisitions to enhance the signal to noise ratio. A subsequent step in processing ICI images for feedback is the application of algorithms to reduce the unprocessed imaging information to one or few output parameters by identifying selected interfaces in the sample that indicate process conditions such as depth of material removed, depth of material remaining, change in material height, change in material optical properties, change in material thickness. Depending on the desired feedback one or more of these measurements are transmitted to a feedback controller that may adjust process parameters based on these measurements. In some embodiments, this algorithm uses proportional-integral-derivative feedback methods. One or more than one output parameters may be interfaced to the machining light source and/or other subsystems within the material modification platform.

The control parameters within the material modification platform that are controlled may include, for example, but are not limited to sample position; material modification beam steering and/or focussing; material modification light source pulse duration, intensity, pulse energy, pulse fluence, and/or light frequency; gas assist pressure and/or gas type.

In some embodiments, the image processor may store the data present at one or more points in the processing chain for troubleshooting and quality assurance use.

The high reflectivity of some materials may cause the detector to saturate, or elevate distant features of the system point spread function (sometimes referred to as "shoulders") above the noise floor. Either of these can reduce image quality and hinder automatic feedback processing. Some embodiments of ICI detectors and/or image processors are capable of detecting these adverse conditions and taking corrective measures on the fly. For example, detector saturation on the constructively interfering fringes of the interferogram tends to clip the top of the fringes which creates additional frequency component power that would be spread across multiple depths resulting in an imaging artifact. In this example, some embodiments of ICI controllers may detect that one or more pixels on the detector are at a saturated level and switch to a different processing algorithm that is suited for saturation. Even with the clipped spectrum, the majority of the signal power is still delivered at the fundamental frequency and so, in some embodiments, a maximum seek procedure may be used to locate the depth of the bright reflector. Some embodiments of the invention may dynamically or statically adjust the detector gain, adjust detector sensitivity, adjust detector integration time, modulate the reference arm power, and/or modulate the illumination intensity as other methods of managing saturation. In cases where the detector has not saturated, but point spread function shoulders have been substantially elevated above the noise floor, some embodiments of the invention will employ digital dynamic range compression to diminish the shoulder intensity to below acceptable levels (usually below the noise floor).

In some embodiments, one or more of the outputs of the feedback controller are interfaced to the inline coherent imaging unit or the image processor unit, to allow on-the-fly adjustment of parameters within these units to achieve robust feedback control. Examples of such parameters include but are not limited to, reference arm power, reference arm length, image beam polarization, reference or sample obstruction (i.e., beam blocking), image acquisition time (integration time and number of images to average), detector gain and/or dynamic range.

More advanced feedback techniques that may be employed in some embodiments include:
Select a window of ~10 depths around the primary machining front and track the front within those depths.
Select another window of ~10 depths some distance (this depends on how much advanced notice of breakthrough is desired) below the primary machining front depth and search for interface signals within that depth.
When subsurface interface is found, check signature against known features to ensure that it is the target interface of choice.
Report margin depth to feedback controller.
Feedback controller decides if process needs to be slowed or stopped and effects such control on the process equipment.

Some embodiments feature one or more of the following:
Optics configured to place the imaging focus as close as possible to target depth to maximize SNR. This may mean that the imaging and machining foci are displaced axially from each other.
Optics configured to avoid side-wall reflections that might confuse the image processing feedback system;
System timing to control when to fire the imaging system;
Streamlined image processing including the homodyne filter algorithm, processing reflection intensity from a reduced subset of sample depths. Additionally, this algorithm gives a higher quality point spread function than standard techniques (see FIG. 20);
using an FPGA or ASIC in the image processor in order to reduce processing latency, enabling an increase in processing speed;
Interface and/or signal trend tracking algorithms that may be run in real time.

The terms "feedback" and "feedback control", when used to describe the function of invention described herein, refer to automatic electronic and/or electro-optical feedback control, where the data generated by the ICI imaging subsystem are further processed by a controller to provide a control signal to a material processing subsystem.

It is noted that any of the embodiments described herein may be implemented with a common objective lens for the modification beam and the imaging beam.

In all embodiments of the invention, a sample arm optical path and a reference optical path are used. These paths may overlap and be shared at various points throughout the invention. Optical path length in this application refers to all space and matter traversed by the imaging light that contribute to optical path delay, including physical path length as well as optical dispersion and other optical frequency dependant phase variation, optical media with varied phase and/or group velocities.

Numerous modifications and variations of the present disclosure are possible in light of the above teachings. It is therefore to be understood that within the scope of the appended claims, the disclosure may be practiced otherwise than as specifically described herein.

We claim:
1. An apparatus that generates a record of a material modification process, the apparatus comprising:
a material processing beam source that produces a material processing beam that is applied to a sample location in the material modification process, wherein the material modification process is a welding process;
an imaging optical source that produces imaging light;
an optical interferometer that produces an interferometry output using at least a component of the imaging light that is delivered into a phase change region created in the material during the welding process, the interferometry output based on at least one optical path length to at least one point in the phase change region compared to another optical path length;
a detector that receives the interferometry output and produces a detector output that is indicative of a characteristic of the phase change region during the welding process; and
a record generator that generates at least one record based on the detector output at a plurality of times.

2. The apparatus of claim 1, further comprising:
a computer readable storage medium;
wherein the record generator stores the record on the computer readable storage medium.

3. The apparatus of claim 1, wherein the apparatus is configured to produce the material processing beam and the imaging light substantially co-axially when delivered into the phase change region.

4. The apparatus of claim 1, wherein the at least one record comprises at least one parameter selected from:
quality of the weld;
an element of a melt pool in the process of welding;
an indication of an impending break through;
an indication of keyhole stability; and
penetration depth.

5. The apparatus of claim 1, wherein the apparatus controls at least one processing parameter of the material modification process based on the at least one record.

6. The apparatus of claim 5, wherein the at least one processing parameter of the material modification process that is controlled comprises at least one of:
on/off state of the material processing beam;
average power of the material processing beam;
pulse duration of the material processing beam;
peak intensity of the material processing beam;
density of the material processing beam;
energy of the material processing beam;
particle species of the material processing beam;
wavelength of the material processing beam;
pulse repetition rate of the material processing beam;
pulse energy of the material processing beam;
pulse shape of the material processing beam;
scan speed of the material processing beam;
focal diameter of the material processing beam;
focal position of the material processing beam;
spatial pattern of the material processing beam on the sample;
material feed rate;
cooling media flow rate;
cover/assist gas flow rate;
cover/assist gas pressure;
cover/assist gas blend;
at least one arc welding process parameter selected from voltage, current, and wire feed rate; and
additive material feed rate.

7. A method of generating a record of a material modification process, the method comprising:
applying a material processing beam to a sample location as part of the material modification process, wherein the material modification process is a welding process;
generating imaging light with an imaging optical source;
producing an interferometry output using at least a component of the imaging light that is delivered into a phase change region created in the material during the welding process, the interferometry output based on at least one optical path length to at least one point in the phase change region compared to another optical path length;
detecting the interferometry output producing a detector output that is indicative of a characteristic of the phase change region during the welding process; and
generating at least one record based on the detector output at a plurality of times.

8. The method of claim 7, further comprising storing the at least one record.

9. The method of claim 7, wherein the material processing beam and the imaging light are substantially co-axial when delivered into the phase change region.

10. The method of claim 7, wherein the at least one record comprises a quality of the weld.

11. The method of claim 7, wherein the at least one record comprises an element of the melt pool in the process of welding.

12. The method of claim 7, wherein the at least one record comprises an indication of an impending: break through.

13. The method of claim 7, wherein a material interface on an interior of the sample is identified and used for controlling the material modification process.

14. The method of claim 7, wherein the at least one record comprises keyhole stability.

15. The method of claim 7, wherein the at least one record comprises penetration depth.

16. The method of claim 7, further comprising controlling at least one processing parameter of the material modification process based on the at least one record.

17. The method of claim 7, comprising generating at least two records.

18. The method of claim 17, further comprising controlling at least two processing parameters of the material modification process based on the at least two records.

19. The method of claim 16, wherein controlling at least one processing parameter of the material modification process based on the at least one record is performed in real-time to control the at least one processing parameter of the material modification process during said process.

20. The method of claim 16, comprising controlling at least one processing parameter selected from:
on/off state of the material processing beam;
average power of the material processing beam;
pulse duration of the material processing beam;
peak intensity of the material processing beam;
density of the material processing beam;
energy of the material processing beam;
particle species of the material processing beam;
wavelength of the material processing beam;
pulse repetition rate of the material processing beam;
pulse energy of the material processing beam;
pulse shape of the material processing beam;
scan speed of the material processing beam;
focal diameter of the material processing beam;
focal position of the material processing beam;
spatial pattern of the material processing beam on the sample;
material feed rate;
cooling media flow rate;
cover/assist gas flow rate;
cover/assist gas pressure;
cover/assist gas blend;
at least one arc welding process parameter selected from voltage, current, and wire feed rate; and
additive material feed rate.

21. The method of claim 7, further comprising
automatically controlling at least one processing parameter of the material modification process based on the at least one record.

22. The method of claim 7, wherein the material modification process comprises welding a metal, a plastic, or a polymer.

23. The method of claim 7, wherein the material comprises at least one of:
metal;
semiconductor;
dielectric;
hard biological tissue;
soft biological tissue;

polymer;
plastic; and
composite.

24. The method of claim 7, further comprising
analyzing the interferometry output to produce an indication of at least one of:
when the material processing beam has penetrated to a specified depth;
proximity of a region of the material currently being modified to other regions of the material;
remaining amount of material to be penetrated;
total depth that has been modified;
absolute final depth reached;
fluctuations of depth;
speed of depth change; and
remaining distance to a subsurface interface.

* * * * *